(12) United States Patent
Newman et al.

(10) Patent No.: US 12,295,714 B2
(45) Date of Patent: May 13, 2025

(54) NEEDLE ASSEMBLY INCLUDING AN ALIGNED MAGNETIC ELEMENT

(71) Applicant: C. R. Bard, Inc., Murray Hill, NJ (US)

(72) Inventors: Jon B. Newman, Centerville, UT (US);
Sarah L Creasy, Park City, UT (US);
Randi Cleverly, Bountiful, UT (US);
Michael S. Guthrie, Crestwood, KY (US); Joseph J. Stupak, Jr., Portland, OR (US); Glade H. Howell, Draper, UT (US); Eddie K. Burnside, Bountiful, UT (US); Bret Hamatake, Grantsville, UT (US); Chad A. Hadley, North Salt Lake, UT (US); Robert N. Golden, Kirkland, WA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 535 days.

(21) Appl. No.: 16/734,011

(22) Filed: Jan. 3, 2020

(65) Prior Publication Data

US 2020/0138332 A1     May 7, 2020

Related U.S. Application Data

(60) Division of application No. 14/040,205, filed on Sep. 27, 2013, now Pat. No. 10,524,691, which is a
(Continued)

(51) Int. Cl.
*A61B 34/20*     (2016.01)
*A61B 5/00*     (2006.01)
(Continued)

(52) U.S. Cl.
CPC ............ *A61B 5/062* (2013.01); *A61B 5/06* (2013.01); *A61B 5/150748* (2013.01);
(Continued)

(58) Field of Classification Search
CPC ..... A61B 5/062; A61B 5/06; A61B 5/150748; A61B 5/6852; A61B 8/0833; A61B 8/0841; A61B 34/20; A61B 2090/3954
See application file for complete search history.

(56) References Cited

U.S. PATENT DOCUMENTS

| | | |
|---|---|---|
| 4,445,501 A | 5/1984 | Bresler |
| 4,905,698 A | 3/1990 | Strohl, Jr. et al. |

(Continued)

FOREIGN PATENT DOCUMENTS

| | | |
|---|---|---|
| CA | 2420676 C | 7/2010 |
| EP | 1717601 A2 | 11/2006 |

(Continued)

*Primary Examiner* — Amal Aly Farag
(74) *Attorney, Agent, or Firm* — Rutan & Tucker LLP

(57) ABSTRACT

A method of attaching a magnetic element to a needle assembly. The needle assembly can include a cannula extending along a longitudinal axis. The method can include placing the magnetic element in a magnetic field such that a magnetic axis of the magnetic element substantially aligns with the magnetic field. The method can further include securing the magnetic element to a portion of the needle assembly while the magnetic element is substantially aligned with the magnetic field such that the magnetic axis of the magnetic element is secured in a desired predetermined orientation.

10 Claims, 46 Drawing Sheets

Related U.S. Application Data continuation-in-part of application No. 13/118,033, filed on May 27, 2011, now Pat. No. 9,554,716, said application No. 14/040,205 is a continuation-in-part of application No. 13/118,138, filed on May 27, 2011, now Pat. No. 9,456,766, said application No. 13/118,033 is a continuation-in-part of application No. 12/323,273, filed on Nov. 25, 2008, now Pat. No. 8,388,541.

(60) Provisional application No. 61/774,512, filed on Mar. 7, 2013, provisional application No. 61/709,877, filed on Oct. 4, 2012, provisional application No. 61/707,782, filed on Sep. 28, 2012, provisional application No. 61/349,771, filed on May 28, 2010, provisional application No. 61/095,921, filed on Sep. 10, 2008, provisional application No. 61/095,451, filed on Sep. 9, 2008, provisional application No. 61/091,233, filed on Aug. 22, 2008, provisional application No. 61/045,944, filed on Apr. 17, 2008, provisional application No. 60/990,242, filed on Nov. 26, 2007.

(51) Int. Cl.
*A61B 5/06* (2006.01)
*A61B 5/15* (2006.01)
*A61B 5/283* (2021.01)
*A61B 8/08* (2006.01)
*A61B 90/00* (2016.01)

(52) U.S. Cl.
CPC ............ *A61B 5/283* (2021.01); *A61B 5/6852* (2013.01); *A61B 8/0833* (2013.01); *A61B 8/0841* (2013.01); *A61B 34/20* (2016.02); *A61B 5/150992* (2013.01); *A61B 2034/2051* (2016.02); *A61B 2090/378* (2016.02); *A61B 2090/3954* (2016.02)

(56) References Cited

U.S. PATENT DOCUMENTS

| | | |
|---|---|---|
| 5,042,486 A | 8/1991 | Pfeiler et al. |
| 5,211,165 A | 5/1993 | Dumoulin et al. |
| 5,255,680 A | 10/1993 | Darrow et al. |
| 5,265,610 A | 11/1993 | Darrow et al. |
| 5,377,678 A | 1/1995 | Dumoulin et al. |
| 5,398,691 A | 3/1995 | Martin et al. |
| 5,437,277 A | 8/1995 | Dumoulin et al. |
| 5,445,150 A | 8/1995 | Dumoulin et al. |
| 5,592,939 A | 1/1997 | Martinelli |
| 5,638,819 A | 6/1997 | Manwaring et al. |
| 5,645,065 A | 7/1997 | Shapiro et al. |
| 5,682,890 A | 11/1997 | Kormos et al. |
| 5,711,299 A | 1/1998 | Manwaring et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,748,767 A | 5/1998 | Raab |
| 5,752,513 A | 5/1998 | Acker et al. |
| 5,762,064 A | 6/1998 | Polvani |
| 5,769,843 A | 6/1998 | Abela et al. |
| 5,776,064 A | 7/1998 | Kalfas et al. |
| 5,833,608 A | 11/1998 | Acker |
| 5,843,076 A | 12/1998 | Webster, Jr. et al. |
| 5,899,860 A | 5/1999 | Pfeiffer et al. |
| 5,902,238 A | 5/1999 | Golden et al. |
| 5,944,022 A | 8/1999 | Nardella et al. |
| 5,944,023 A | 8/1999 | Johnson et al. |
| 5,983,126 A | 11/1999 | Wittkampf |
| 5,997,473 A | 12/1999 | Taniguchi et al. |
| 6,052,610 A | 4/2000 | Koch |
| 6,073,043 A | 6/2000 | Schneider |
| 6,082,366 A | 7/2000 | Andra et al. |
| 6,211,666 B1 | 4/2001 | Acker |
| 6,226,547 B1 | 5/2001 | Lockhart et al. |
| 6,248,074 B1 | 6/2001 | Ohno et al. |
| 6,266,552 B1 | 7/2001 | Slettenmark |
| 6,275,724 B1 | 8/2001 | Dickinson et al. |
| 6,298,261 B1 | 10/2001 | Rex |
| 6,370,411 B1 | 4/2002 | Osadchy et al. |
| 6,373,240 B1 | 4/2002 | Govari |
| 6,427,079 B1 | 7/2002 | Schneider et al. |
| 6,466,815 B1 | 10/2002 | Saito et al. |
| 6,474,341 B1 | 11/2002 | Hunter et al. |
| 6,484,118 B1 | 11/2002 | Govari |
| 6,493,573 B1 | 12/2002 | Martinelli et al. |
| 6,507,751 B2 | 1/2003 | Blume et al. |
| 6,522,909 B1 | 2/2003 | Garibaldi et al. |
| 6,528,991 B2 | 3/2003 | Ashe |
| 6,529,761 B2 | 3/2003 | Creighton, IV et al. |
| 6,542,766 B2 | 4/2003 | Hall et al. |
| 6,611,141 B1 | 8/2003 | Schulz et al. |
| 6,615,155 B2 | 9/2003 | Gilboa |
| 6,662,034 B2 | 12/2003 | Segner et al. |
| 6,701,179 B1 | 3/2004 | Martinelli et al. |
| 6,757,557 B1 | 6/2004 | Bladen et al. |
| 6,772,001 B2 | 8/2004 | Maschke |
| 6,856,823 B2 | 2/2005 | Ashe |
| 6,911,026 B1 | 6/2005 | Hall et al. |
| 6,934,575 B2 | 8/2005 | Ferre et al. |
| 6,947,788 B2 | 9/2005 | Gilboa et al. |
| 6,968,846 B2 | 11/2005 | Viswanathan |
| 6,980,843 B2 | 12/2005 | Eng et al. |
| 7,020,512 B2 | 3/2006 | Ritter et al. |
| 7,096,148 B2 | 8/2006 | Anderson et al. |
| 7,167,738 B2 | 1/2007 | Schweikard et al. |
| 7,174,201 B2 | 2/2007 | Govari et al. |
| 7,321,228 B2 | 1/2008 | Govari |
| 7,366,563 B2 | 4/2008 | Kleen et al. |
| 7,543,239 B2 | 6/2009 | Viswanathan et al. |
| 7,668,583 B2 | 2/2010 | Fegert et al. |
| 7,729,743 B2 | 6/2010 | Sabczynski et al. |
| 7,774,051 B2 | 8/2010 | Voth |
| 7,822,464 B2 | 10/2010 | Maschke et al. |
| 7,831,294 B2 | 11/2010 | Viswanathan |
| 8,055,327 B2 | 11/2011 | Strommer et al. |
| 8,200,313 B1 | 6/2012 | Rambod et al. |
| 8,255,035 B2 | 8/2012 | Cao et al. |
| 8,346,343 B2 | 1/2013 | Kimura et al. |
| 8,391,956 B2 | 3/2013 | Zellers et al. |
| 8,401,616 B2 | 3/2013 | Verard et al. |
| 8,442,621 B2 | 5/2013 | Gorek et al. |
| 8,447,384 B2 | 5/2013 | Xu et al. |
| 8,538,509 B2 | 9/2013 | Harlev et al. |
| 8,556,815 B2 | 10/2013 | Pelissier et al. |
| 8,690,776 B2 | 4/2014 | Razzaque et al. |
| 8,721,655 B2 | 5/2014 | Viswanathan et al. |
| 8,734,440 B2 | 5/2014 | Wu |
| 8,942,784 B2 | 1/2015 | Neidert et al. |
| 8,965,490 B2 | 2/2015 | Lee et al. |
| 9,014,794 B2 | 4/2015 | Brodnick et al. |
| 9,179,860 B2 | 11/2015 | Markowitz et al. |
| 2002/0156363 A1 | 10/2002 | Hunter et al. |
| 2003/0036696 A1 | 2/2003 | Willis et al. |
| 2003/0073901 A1 | 4/2003 | Simon et al. |
| 2003/0120150 A1 | 6/2003 | Govari |
| 2003/0163142 A1 | 8/2003 | Paltieli et al. |
| 2003/0236445 A1 | 12/2003 | Couvillon, Jr. |
| 2004/0059217 A1 | 3/2004 | Kessman et al. |
| 2004/0097803 A1 | 5/2004 | Panescu |
| 2004/0097804 A1 | 5/2004 | Sobe |
| 2004/0147837 A1 | 7/2004 | Macaulay et al. |
| 2004/0162487 A1 | 8/2004 | Klingenbeck-Regn et al. |
| 2005/0004450 A1 | 1/2005 | Ben-Haim et al. |
| 2005/0049486 A1 | 3/2005 | Urquhart et al. |
| 2005/0075561 A1 | 4/2005 | Golden |
| 2005/0085715 A1* | 4/2005 | Dukesherer ............ A61B 5/062 128/899 |

(56) References Cited

U.S. PATENT DOCUMENTS

| | | | |
|---|---|---|---|
| 2005/0245811 A1* | 11/2005 | Scheffler | G01R 33/287 600/410 |
| 2005/0288586 A1 | 12/2005 | Ferek-Petric | |
| 2006/0149134 A1 | 7/2006 | Soper et al. | |
| 2006/0241397 A1 | 10/2006 | Govari et al. | |
| 2006/0253029 A1 | 11/2006 | Altmann et al. | |
| 2006/0258895 A1 | 11/2006 | Maschke | |
| 2006/0287595 A1 | 12/2006 | Maschke | |
| 2007/0013540 A1 | 1/2007 | Altmann et al. | |
| 2007/0016013 A1 | 1/2007 | Camus | |
| 2007/0049817 A1 | 3/2007 | Preiss et al. | |
| 2007/0055141 A1 | 3/2007 | Kruger et al. | |
| 2007/0066888 A1 | 3/2007 | Maschke | |
| 2007/0135886 A1 | 6/2007 | Maschke | |
| 2007/0167743 A1 | 7/2007 | Honda et al. | |
| 2007/0197905 A1 | 8/2007 | Timinger et al. | |
| 2007/0225589 A1 | 9/2007 | Viswanathan | |
| 2007/0232882 A1 | 10/2007 | Glossop et al. | |
| 2007/0232896 A1 | 10/2007 | Gilboa et al. | |
| 2007/0238984 A1 | 10/2007 | Maschke et al. | |
| 2007/0249911 A1 | 10/2007 | Simon | |
| 2007/0265526 A1 | 11/2007 | Govari et al. | |
| 2007/0282197 A1 | 12/2007 | Bill et al. | |
| 2007/0299352 A1 | 12/2007 | Harlev et al. | |
| 2008/0033282 A1 | 2/2008 | Bar-Tal et al. | |
| 2008/0171934 A1 | 7/2008 | Greenan et al. | |
| 2008/0190438 A1 | 8/2008 | Harlev et al. | |
| 2008/0255446 A1 | 10/2008 | Akins | |
| 2008/0262338 A1 | 10/2008 | Paitel et al. | |
| 2009/0115406 A1 | 5/2009 | Anderson et al. | |
| 2009/0182224 A1 | 7/2009 | Shmarak et al. | |
| 2010/0036238 A1 | 2/2010 | Neidert et al. | |
| 2010/0057157 A1 | 3/2010 | Govari et al. | |
| 2010/0060472 A1 | 3/2010 | Kimura et al. | |
| 2010/0106011 A1 | 4/2010 | Byrd et al. | |
| 2010/0160772 A1 | 6/2010 | Gardeski et al. | |
| 2010/0168557 A1 | 7/2010 | Deno et al. | |
| 2010/0198048 A1* | 8/2010 | Togawa | A61B 8/445 600/424 |
| 2010/0234724 A1* | 9/2010 | Jacobsen | A61B 34/20 600/424 |
| 2010/0274150 A1 | 10/2010 | Harlev et al. | |
| 2012/0016316 A1* | 1/2012 | Zhuang | A61B 34/20 604/528 |
| 2012/0035539 A1 | 2/2012 | Tegg | |
| 2013/0006100 A1 | 1/2013 | Shachar et al. | |
| 2013/0079628 A1 | 3/2013 | Groszmann et al. | |
| 2013/0131503 A1 | 5/2013 | Schneider et al. | |
| 2013/0169272 A1 | 7/2013 | Eichler et al. | |
| 2013/0223702 A1 | 8/2013 | Holsing et al. | |
| 2013/0296691 A1 | 11/2013 | Ashe | |
| 2013/0303896 A1 | 11/2013 | Kalpin et al. | |
| 2013/0303945 A1 | 11/2013 | Blumenkranz et al. | |
| 2014/0094768 A1 | 4/2014 | Stangenes et al. | |
| 2014/0180074 A1 | 6/2014 | Green et al. | |
| 2014/0187917 A1 | 7/2014 | Clark et al. | |
| 2014/0249428 A1 | 9/2014 | Ingold, Jr. et al. | |
| 2014/0253270 A1 | 9/2014 | Nicholls et al. | |
| 2014/0257080 A1 | 9/2014 | Dunbar et al. | |
| 2014/0275957 A1 | 9/2014 | Lupotti | |
| 2014/0275990 A1 | 9/2014 | Hagy et al. | |
| 2014/0276010 A1 | 9/2014 | Anderson | |
| 2015/0025365 A1 | 1/2015 | Esguerra Wilczynski et al. | |
| 2015/0173723 A1 | 6/2015 | Bates et al. | |
| 2015/0223775 A1 | 8/2015 | Hamilton, Jr. | |
| 2015/0282734 A1 | 10/2015 | Schweikert et al. | |
| 2017/0086782 A1 | 3/2017 | Hagy et al. | |
| 2017/0151022 A1 | 6/2017 | Jascob et al. | |
| 2018/0116723 A1 | 5/2018 | Hettrick et al. | |
| 2018/0145443 A1 | 5/2018 | Andreason et al. | |

FOREIGN PATENT DOCUMENTS

| | | |
|---|---|---|
| EP | 2170162 B1 | 8/2017 |
| JP | 2001514533 A | 9/2001 |
| JP | 2002529133 A | 9/2002 |
| RU | 2009101949 A | 7/2010 |
| WO | 2006074509 A1 | 7/2006 |
| WO | 2006074510 A1 | 7/2006 |
| WO | 2006078677 A2 | 7/2006 |
| WO | 2013034175 A1 | 3/2013 |

* cited by examiner

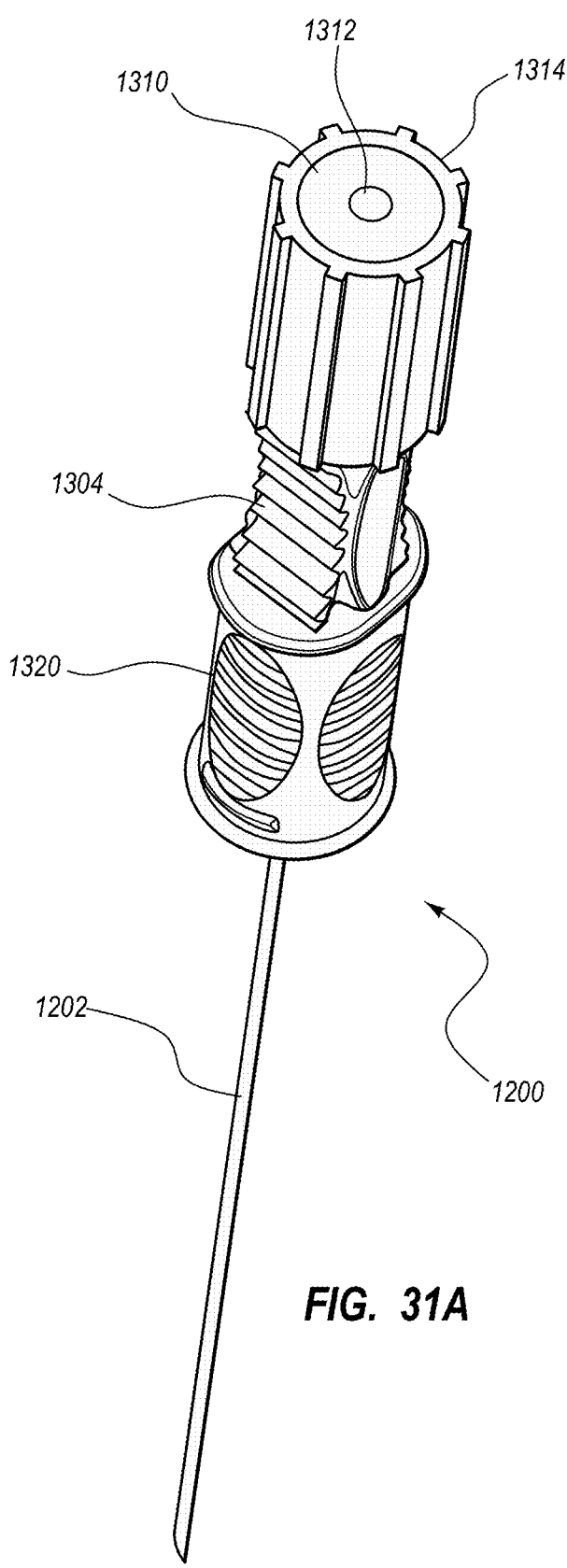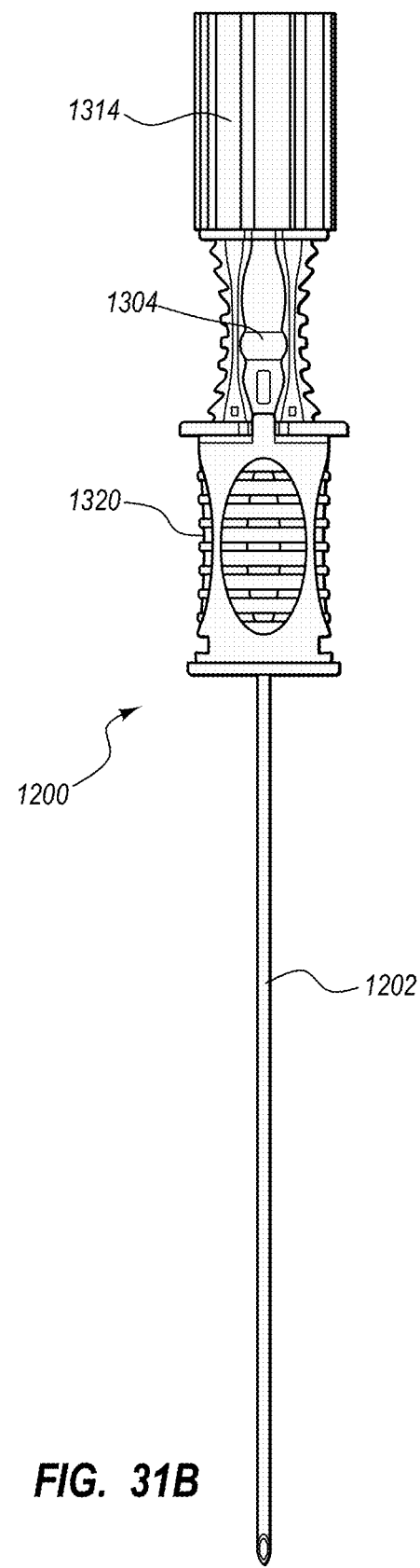
FIG. 31A
FIG. 31B

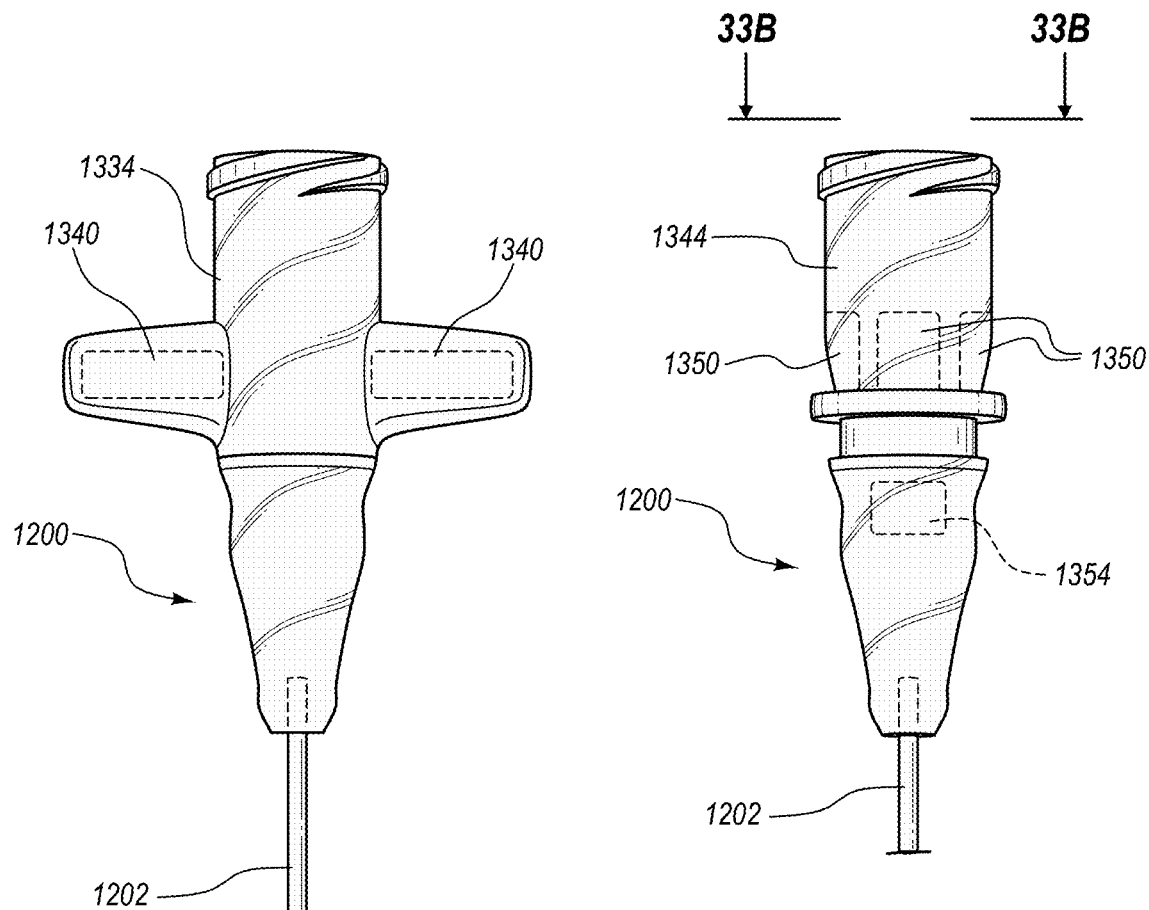
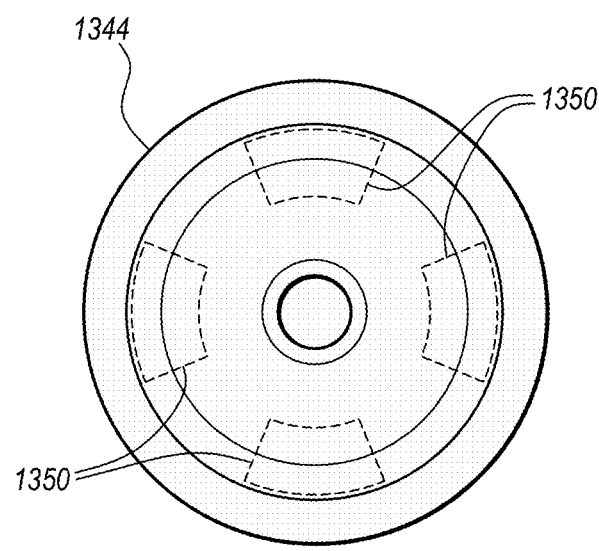
FIG. 32
FIG. 33A
FIG. 33B

NEEDLE ASSEMBLY INCLUDING AN ALIGNED MAGNETIC ELEMENT

CROSS-REFERENCE TO RELATED APPLICATIONS

This application is a division of U.S. patent application Ser. No. 14/040,205, filed Sep. 27, 2013, now U.S. Pat. No. 10,524,691, which claims the benefit of U.S. Provisional Patent Application Nos: 1) 61/707,782, filed Sep. 28, 2012; 2) 61/709,877, filed Oct. 4, 2012; and 3) 61/774,512, filed Mar. 7, 2013, and which is a continuation-in-part of U.S. patent application Ser. No. 13/118,138, filed May 27, 2011, now U.S. Pat. No. 9,456,766, which claims the benefit of U.S. Provisional Patent Application No. 61/349,771, filed May 28, 2010, and which is a continuation-in-part of U.S. patent application Ser. No. 13/118,033, filed May 27, 2011, now U.S. Pat. No. 9,554,716, which also claims the benefit of U.S. Provisional Patent Application No. 61/349,771, filed May 28, 2010, and which is a continuation-in-part of U.S. patent application Ser. No. 12/323,273, filed Nov. 25, 2008, now U.S. Pat. No. 8,388,541, which claims the benefit of U.S. Provisional Patent Application Nos: 1) 61/095,921, filed Sep. 10, 2008; 2) 61/095,451, filed Sep. 9, 2008; 3) 61/091,233, filed Aug. 22, 2008; 4) 61/045,944, filed Apr. 17, 2008; and 5) 60/990,242, filed Nov. 26, 2007. Each of the aforementioned applications is incorporated herein by reference in its entirety.

BRIEF SUMMARY

Briefly summarized, embodiments of the present invention are directed to an integrated catheter placement system configured for accurately placing a catheter within the vasculature of a patient. The integrated system employs at least two modalities for improving catheter placement accuracy: 1) ultrasound-assisted guidance for introducing the catheter into the patient's vasculature; and 2) a tip location system ("TLS"), or magnetically-based (e.g., via permanent magnet(s) or electromagnet(s)) tracking of the catheter tip during its advancement through the vasculature to detect and facilitate correction of any tip malposition during such advancement.

In one embodiment, the integrated system comprises a system console including a control processor, a tip location sensor for temporary placement on a portion of a body of the patient, and an ultrasound probe. The tip location sensor senses a magnetic field of a stylet disposed in a lumen of the catheter when the catheter is disposed in the vasculature. The ultrasound probe ultrasonically images a portion of the vasculature prior to introduction of the catheter into the vasculature. In addition, the ultrasound probe includes user input controls for controlling use of the ultrasound probe in an ultrasound mode and use of the tip location sensor in a tip location mode.

In another embodiment, a third modality, i.e., ECG signal-based catheter tip guidance, is included in the system to enable guidance of the catheter tip to a desired position with respect to a node of the patient's heart from which the ECG signals originate.

In addition, embodiments of the present disclosure are also directed to a guidance system for assisting with the insertion of a needle or other medical component into the body of a patient. The guidance system utilizes ultrasound imaging or other suitable imaging technology.

In one embodiment, the guidance system comprises an imaging device including a probe for producing an image of an internal body portion target, such as a subcutaneous vessel, for instance. One or more sensors are included with the probe. The sensors sense a detectable characteristic related to the needle, such as a magnetic field of a magnet included with the needle.

The system includes a processor that uses data relating to the detectable characteristic sensed by the sensors to determine a position and/or orientation of the needle in three spatial dimensions. The system includes a display for depicting the position and/or orientation of the needle together with the image of the target.

In addition to magnet-based detection, other modalities for detecting the medical component are disclosed, including optically-based and electromagnetic signal-based systems.

In one embodiment, a stylet including one or more magnetic elements is removably inserted into the needle to enable tracking of the needle via detection of the magnetic elements by a sensor included with the ultrasound probe. In one embodiment, the sensor is a ring sensor disposed about a portion of the ultrasound probe. In another embodiment, the stylet can additionally include a strain sensor that detects bending of the needle during insertion into the patient. Feedback from the strain sensor can be input into the system and accounted for in order to more accurately depict needle location on the display.

In yet another embodiment, the magnetic element is configured as a donut-shaped passive magnet defining a hole through which the cannula of the needle passes. In yet another embodiment, a needle assembly including a hub, cannula, and magnetic element is also disclosed, wherein a magnetic axis of the magnetic element is configured to be coaxially aligned with the needle cannula. Fixtures and devices for aligning such a magnetic element are also disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 31A-31D are various views of a needle and associated components for use with a needle guidance system, according to one embodiment;

FIG. 32 is a side view of a needle for use with a needle guidance system, according to one embodiment;

FIGS. 33A and 33B are various views of a needle for use with a needle guidance system, according to one embodiment;

DETAILED DESCRIPTION OF SELECTED EMBODIMENTS

Figure 1:
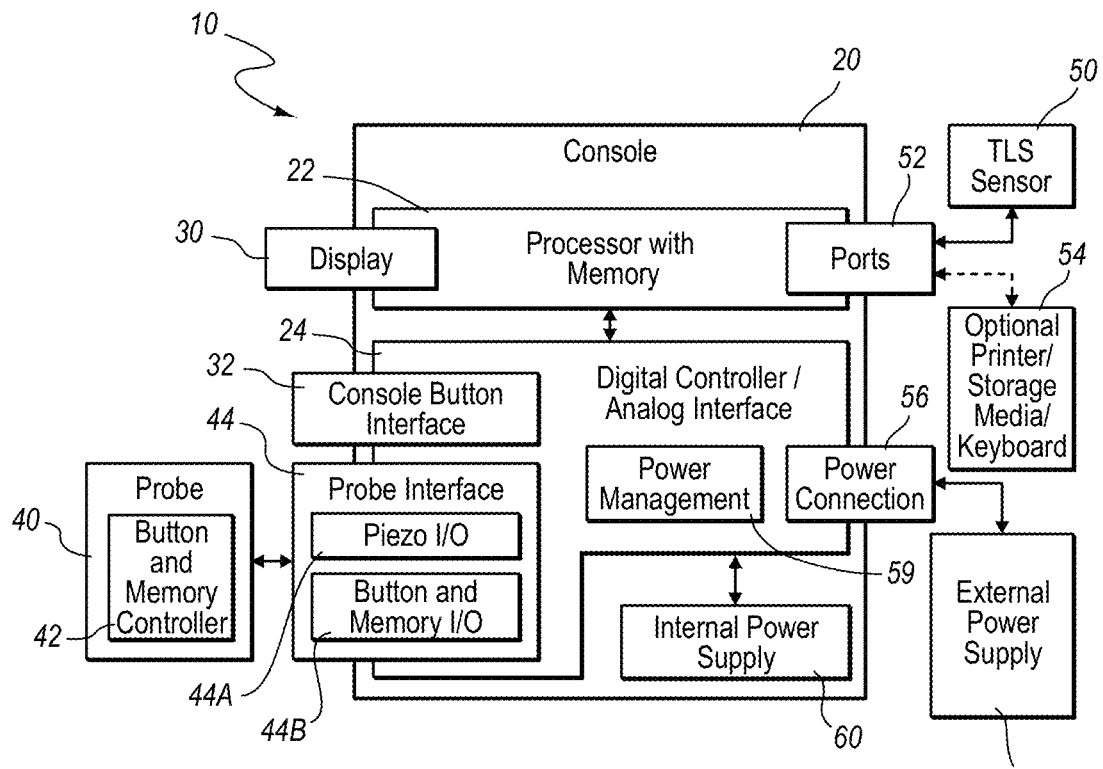
FIG. 1 is a block diagram depicting various elements of an integrated system for intravascular placement of a catheter, according to one example embodiment of the present invention.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

I. Assisted Catheter Placement

Embodiments of the present invention are generally directed to a catheter placement system configured for accurately placing a catheter within the vasculature of a patient. In one embodiment, the catheter placement system employs at least two modalities for improving catheter placement accuracy: 1) ultrasound-assisted guidance for introducing the catheter into the patient's vasculature; and 2) a tip location/navigation system ("TLS"), or magnetically-based tracking of the catheter tip during its advancement through the tortuous vasculature path to detect and facilitate correction of any tip malposition during such advancement. The ultrasound guidance and tip location features of the present system according to one embodiment are integrated into a single device for use by a clinician placing the catheter. Integration of these two modalities into a single device simplifies the catheter placement process and results in relatively faster catheter placements. For instance, the integrated catheter placement system enables ultrasound and TLS activities to be viewed from a single display of the integrated system. Also, controls located on an ultrasound probe of the integrated device, which probe is maintained within the sterile field of the patient during catheter placement, can be used to control functionality of the system, thus precluding the need for a clinician to reach out of the sterile field in order to control the system.

In another embodiment, a third modality, i.e., ECG signal-based catheter tip guidance, is included in the integrated system to enable guidance of the catheter tip to a desired position with respect to a node of the patient's heart from which the ECG signals originate. Such ECG-based positional assistance is also referred to herein as "tip confirmation."

Combination of the three modalities above according to one embodiment enables the catheter placement system to facilitate catheter placement within the patient's vasculature with a relatively high level of accuracy, i.e., placement of the distal tip of the catheter in a predetermined and desired position. Moreover, because of the ECG-based guidance of the catheter tip, correct tip placement may be confirmed without the need for a confirmatory X-ray. This, in turn, reduces the patient's exposure to potentially harmful x-rays, the cost and time involved in transporting the patient to and from the x-ray department, costly and inconvenient catheter repositioning procedures, etc.

Figure 2:
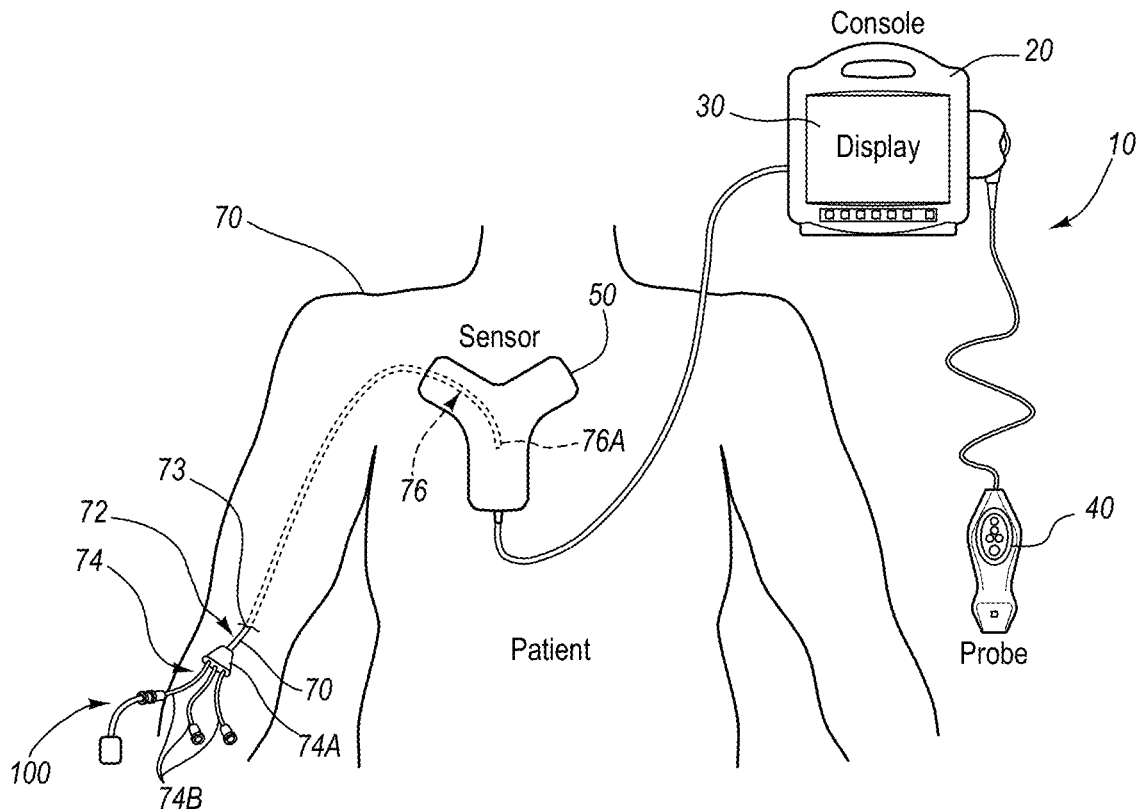
FIG. 2 is a simplified view of a patient and a catheter being inserted therein with assistance of the integrated system of FIG. 1.

Reference is first made to FIGS. 1 and 2 which depict various components of a catheter placement system ("system"), generally designated at 10, configured in accordance with one example embodiment of the present invention. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal potion 76 that resides within the patient vasculature after placement is complete. The system 10 is employed to ultimately position a distal tip 76A of the catheter 72 in a desired position within the patient vasculature. In one embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

Figure 8A:
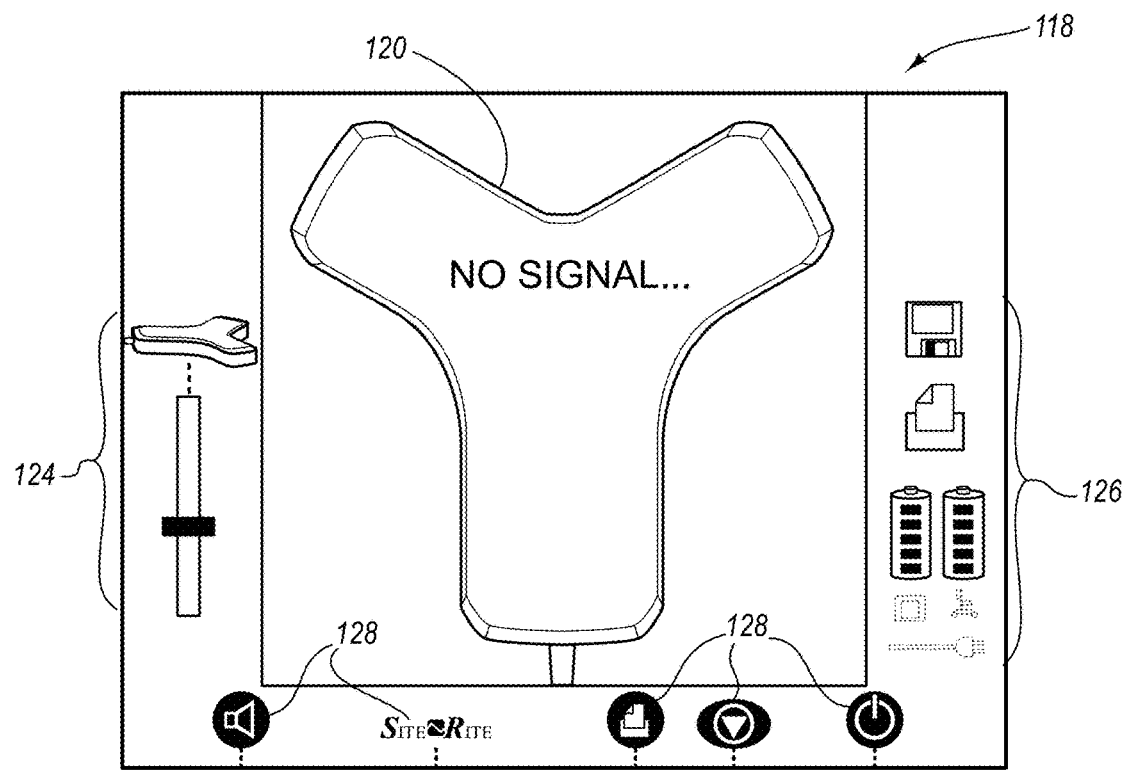
FIGS. 8A-8C are screenshots of images depicted on a display of the integrated system of FIG. 1 during catheter tip placement procedures.
Figure 8B:
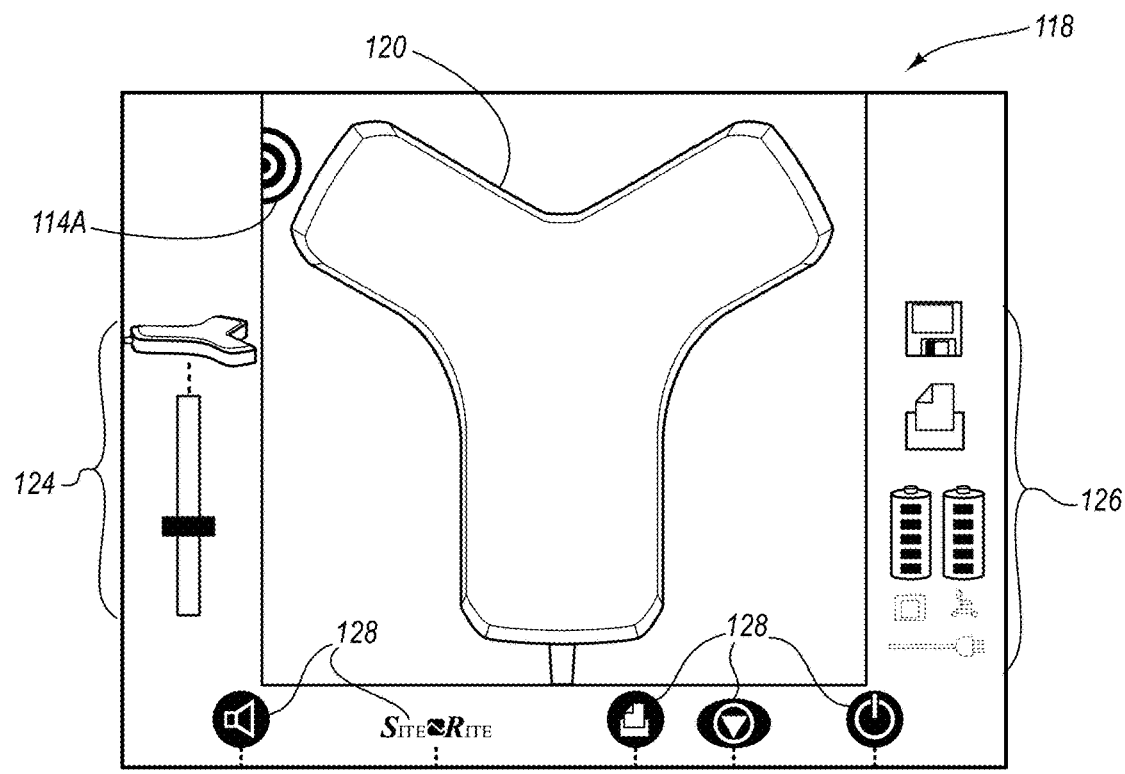
Figure 8C:
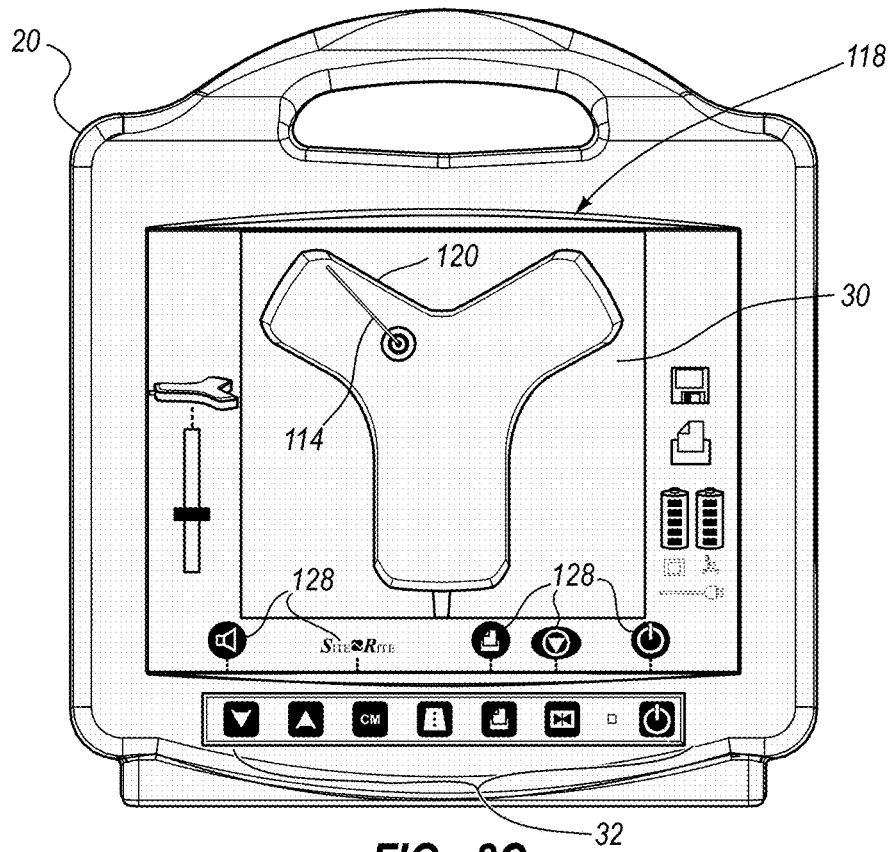

An example implementation of the console 20 is shown in FIG. 8C, though it is appreciated that the console can take one of a variety of forms. A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 (see FIGS. 1, 8C) and buttons included on the probe 40 can be used to immediately call up a desired mode to the display 30 by the clinician to assist in the placement procedure. In one embodiment, information from multiple modes, such as TLS and ECG, may be displayed simultaneously, such as in FIG. 17. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

Figure 3A:
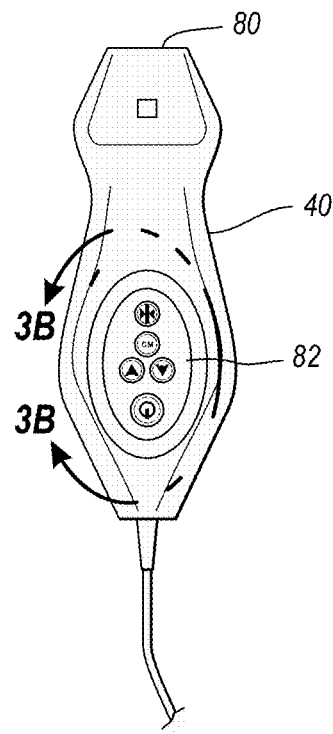
FIGS. 3A and 3B are views of a probe of the integrated system of FIG. 1.
Figure 3B:
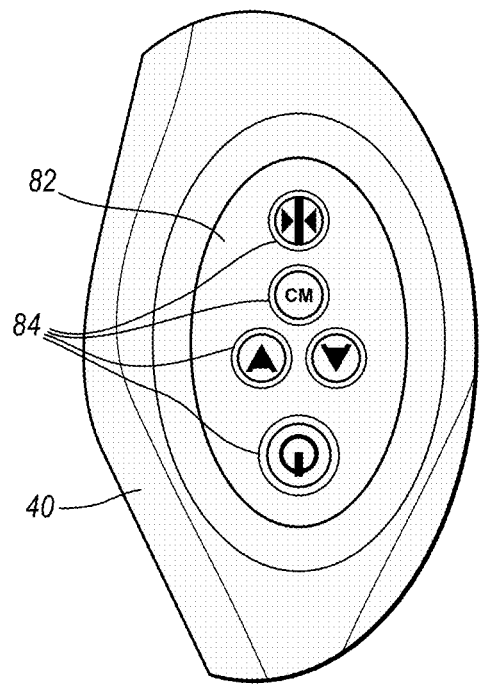

FIGS. 3A and 3B depict features of the probe 40 according to one embodiment. The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

The handheld probe 40 includes a head 80 that houses a piezoelectric array for producing ultrasonic pulses and for receiving echoes thereof after reflection by the patient's body when the head is placed against the patient's skin proximate the prospective insertion site 73 (FIG. 2). The probe 40 further includes a plurality of control buttons 84, which can be included on a button pad 82. In the present embodiment, the modality of the system 10 can be controlled by the control buttons 84, thus eliminating the need for the clinician to reach out of the sterile field, which is established about the patient insertion site prior to catheter placement, to change modes via use of the console button interface 32.

As such, in one embodiment a clinician employs the first (US) modality to determine a suitable insertion site and establish vascular access, such as with a needle or introducer, then with the catheter. The clinician can then seamlessly switch, via button pushes on the probe button pad 82, to the second (TLS) modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Figure 4:
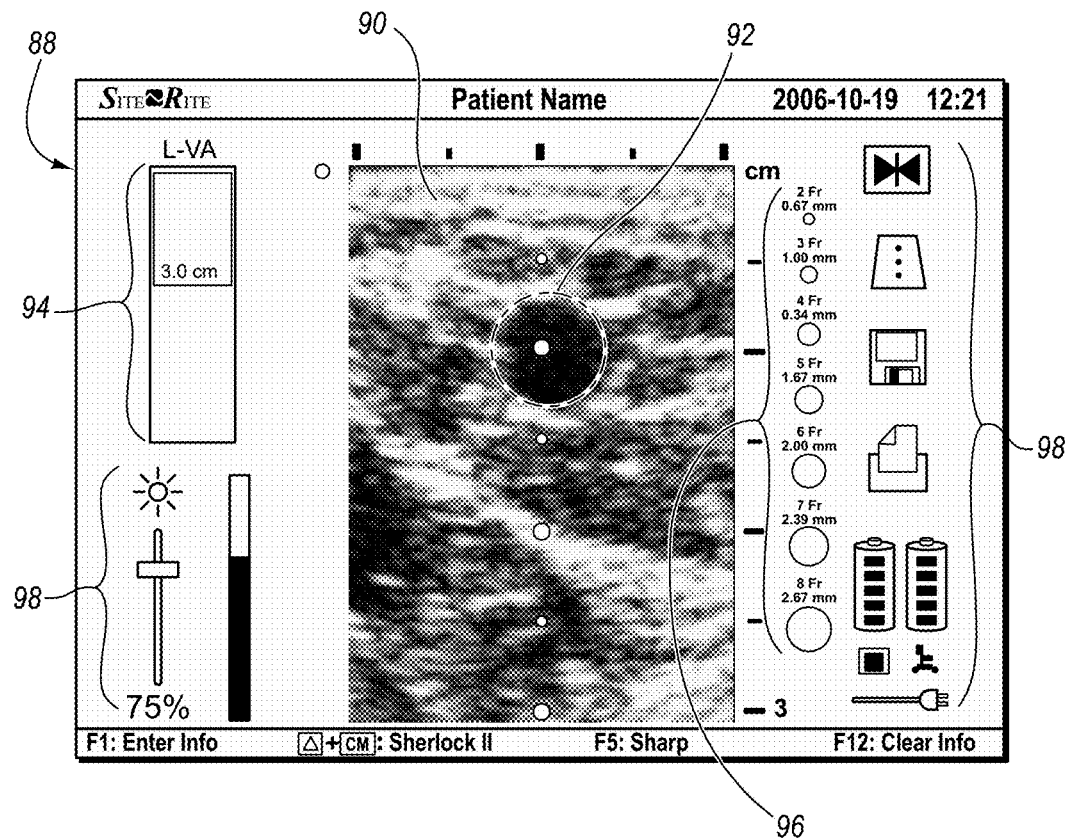
FIG. 4 is a screenshot of an ultrasound image as depicted on a display of the integrated system of FIG. 1.

FIG. 4 shows an example screenshot 88 as depicted on the display 30 while the system 10 is in its first ultrasound modality. An image 90 of a subcutaneous region of the patient 70 is shown, depicting a cross section of a vein 92. The image 90 is produced by operation of the piezoelectric array of the probe 40. also included on the display screenshot 88 is a depth scale indicator 94, providing information regarding the depth of the image 90 below the patient's skin, a lumen size scale 96 that provides information as to the size of the vein 92 relative to standard catheter lumen sizes, and other indicia 98 that provide information regarding status of the system 10 or possible actions to be taken, e.g., freeze frame, image templates, data save, image print, power status, image brightness, etc.

Note that while a vein is depicted in the image 90, other body lumens or portions can be imaged in other embodiments. Note that the US mode shown in FIG. 4 can be simultaneously depicted on the display 30 with other modes, such as the TLS mode, if desired. In addition to the visual display 30, aural information, such as beeps, tones, etc., can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, both US and TLS activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

Figure 5:
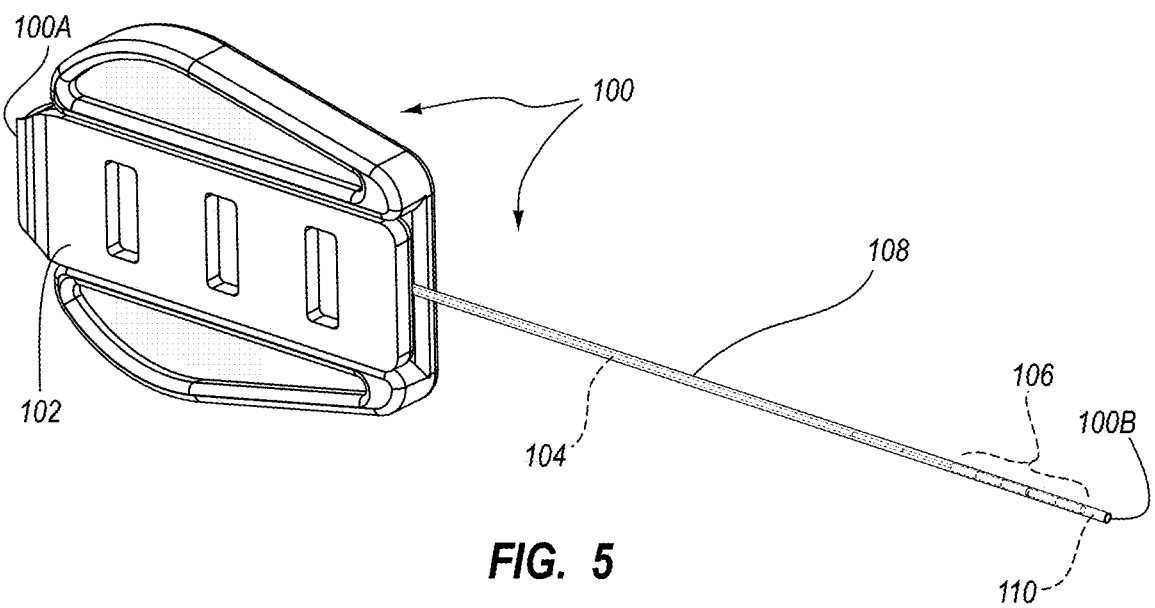
FIG. 5 is a perspective view of a stylet employed in connection with the system of FIG. 1 in placing a catheter within a patient vasculature.

As mentioned, the TLS utilizes a stylet to enable the distal end of the catheter 72 to be tracked during its advancement through the vasculature. FIG. 5 gives an example of such a stylet 100, which includes a proximal end 100A and a distal end 100B. A handle 102 is included at the stylet proximal end 100A, with a core wire 104 extending distally therefrom. A magnetic assembly is disposed distally of the core wire 104. The magnetic assembly includes one or more magnetic elements 106 disposed adjacent one another proximate the stylet distal end 100B and encapsulated by tubing 108. In the present embodiment, a plurality of magnetic elements 106 is included, each element including a solid, cylindrically shaped ferromagnetic stacked end-to-end with the other magnetic elements. An adhesive tip 110 can fill the distal tip of the tubing 108, distally to the magnetic elements 106.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845, titled "Medical Instrument Location Means," which is incorporated herein by reference in its entirety. Yet other examples of stylets including magnetic elements that can be employed with the TLS modality can be found in U.S. Pat. No. 8,784,336, filed Aug. 23, 2006, titled "Stylet Apparatuses and Methods of Manufacture," which is incorporated herein by reference in its entirety. These and other variations are therefore contemplated by embodiments of the present invention. It should appreciated herein that "stylet" as used herein can include any one of a variety of devices configured for removable placement within a lumen of the catheter to assist in placing a distal end of the catheter in a desired location within the patient's vasculature.

FIG. 2 shows disposal of the stylet 100 substantially within a lumen in the catheter 72 such that the proximal portion thereof extends proximally from the catheter lumen, through the hub 74A and out through a selected one of the extension legs 74B. So disposed within a lumen of the catheter, the distal end 100B of the stylet 100 is substantially co-terminal with the distal catheter end 76A such that detection by the TLS of the stylet distal end correspondingly indicates the location of the catheter distal end.

The TLS sensor 50 is employed by the system 10 during TLS operation to detect a magnetic field produced by the magnetic elements 106 of the stylet 100. As seen in FIG. 2, the TLS sensor 50 is placed on the chest of the patient during catheter insertion. The TLS sensor 50 is placed on the chest of the patient in a predetermined location, such as through the use of external body landmarks, to enable the magnetic field of the stylet magnetic elements 106, disposed in the catheter 72 as described above, to be detected during catheter transit through the patient vasculature. Again, as the magnetic elements 106 of the stylet magnetic assembly are co-terminal with the distal end 76A of the catheter 72 (FIG. 2), detection by the TLS sensor 50 of the magnetic field of the magnetic elements provides information to the clinician as to the position and orientation of the catheter distal end during its transit.

In greater detail, the TLS sensor 50 is operably connected to the console 20 of the system 10 via one or more of the ports 52, as shown in FIG. 1. Note that other connection schemes between the TLS sensor and the system console can also be used without limitation. As just described, the magnetic elements 106 are employed in the stylet 100 to enable the position of the catheter distal end 76A (FIG. 2) to be observable relative to the TLS sensor 50 placed on the patient's chest. Detection by the TLS sensor 50 of the stylet magnetic elements 106 is graphically displayed on the display 30 of the console 20 during TLS mode. In this way, a clinician placing the catheter is able to generally determine the location of the catheter distal end 76A within the patient vasculature relative o the TLS sensor 50 and detect when catheter malposition, such as advancement of the catheter along an undesired vein, is occurring.

Figure 6:
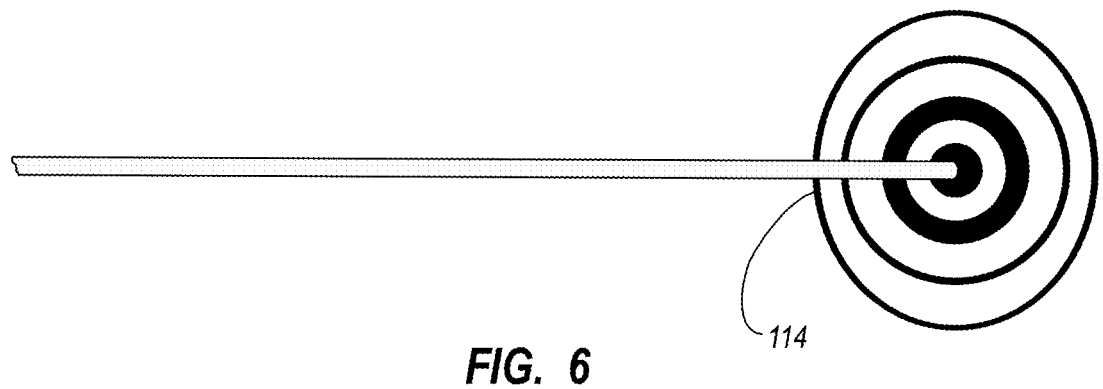
FIG. 6 is an icon as depicted on a display of the integrated system of FIG. 1, indicating a position of a distal end of the stylet of FIG. 5 during catheter tip placement procedures.
Figure 7A:
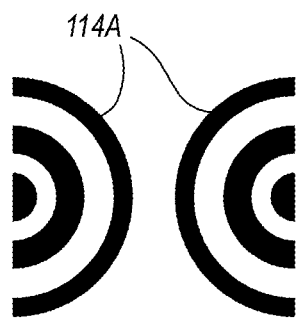
FIGS. 7A-7E depict various example icons that can be depicted on the display of the integrated system of FIG. 1 during catheter tip placement procedures.
Figure 7B:
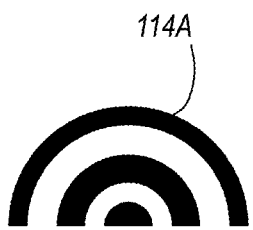
Figure 7C:
Figure 7D:
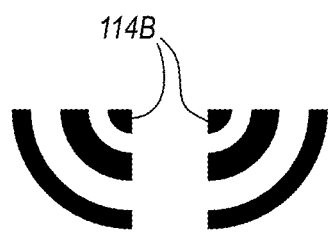
Figure 7E:
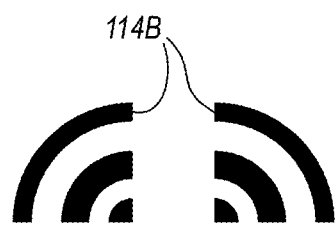

FIGS. 6 and 7A-7E show examples of icons that can be used by the console display 30 to depict detection of the stylet magnetic elements 106 by the TLS sensor 50. In particular, FIG. 6 shows an icon 114 that depicts the distal portion of the stylet 100, including the magnetic elements 106 as detected by the TLS sensor 50 when the magnetic elements are positioned under the TLS sensor. As the stylet distal end 100B is substantially co-terminal with the distal end 76A of the catheter 72, the icon indicates the position and orientation of the catheter distal end. FIGS. 7A-7E show various icons that can be depicted on the on the console display 30 when the magnetic elements 106 of the stylet 100 are not positioned directly under a portion of the TLS sensor 50, but are nonetheless detected nearby. The icons can include half-icons 114A and quarter-icons 114B that are displayed according to the position of the stylet magnetic assembly, i.e., the magnetic elements 106 in the present embodiment, relative to the TLS sensor 50.

FIGS. 8A-8C depict screenshots taken from the display 30 of the system 10 while in TLS mode, showing how the magnetic assembly of the stylet 100 is depicted. The screenshot 118 of FIG. 8A shows a representative image 120 of the TLS sensor 50. Other information is provided on the display screenshot 118, including a depth scale indicator 124, status/action indicia 126, and icons 128 corresponding to the button interface 32 included on the console 20 (FIG. 8C). Though the icons 128 in the present embodiment are simply indicators to guide the user in identifying the purpose of the corresponding buttons of the button interface 32, in another embodiment the display can be made touch-sensitive so that the icons themselves can function as button interfaces and can change according to the mode the system is in.

During initial stages of catheter advancement through the patient's vasculature after insertion therein, the distal end 76A of the catheter 72, having the stylet distal end 100B substantially co-terminal therewith, is relatively distant from the TLS sensor 50. As such, the display screenshot will indicate "no signal," indicating that the magnetic field from the stylet magnetic assembly has not been detected. In FIG. 8B, the magnetic assembly proximate the stylet distal end 100B has advanced sufficiently close to the TLS sensor 50 to be detected thereby, though it is not yet under the sensor. This is indicated by the half-icon 114A shown to the left of the sensor image 120, representing the stylet magnetic assembly being positioned to the right of the TLS sensor 50 from the perspective of the patient.

In FIG. 8C, the magnetic assembly proximate the stylet distal end 100B has advanced under the TLS sensor 50 such that its position and orientation relative thereto is detected by the TLS sensor. This is indicated by the icon 114 on the sensor image 120. Note that the button icons 128 provide indications of the actions that can be performed by pressing the corresponding buttons of the console button interface 32. As such, the button icons 128 can change according to which modality the system 10 is in, thus providing flexibility of use for the button interface 32. Note further that, as the button pad 82 of the probe 40 (FIG. 3A, 3B) includes buttons 84 that mimic several of the buttons of the button interface 32, the button icons 128 on the display 30 provide a guide to the clinician for controlling the system 10 with the probe buttons 84 while remaining in the sterile field. For instance, if the clinician has need to leave TLS mode and return to US (ultrasound) mode, the appropriate control button 84 on the probe button pad 82 can be depressed, and the US mode can be immediately called up, with the display 30 refreshing to accommodate the visual information needed for US functionality, such as that shown in FIG. 4. This is accomplished without a need for the clinician to reach out of the sterile field.

Figure 9:
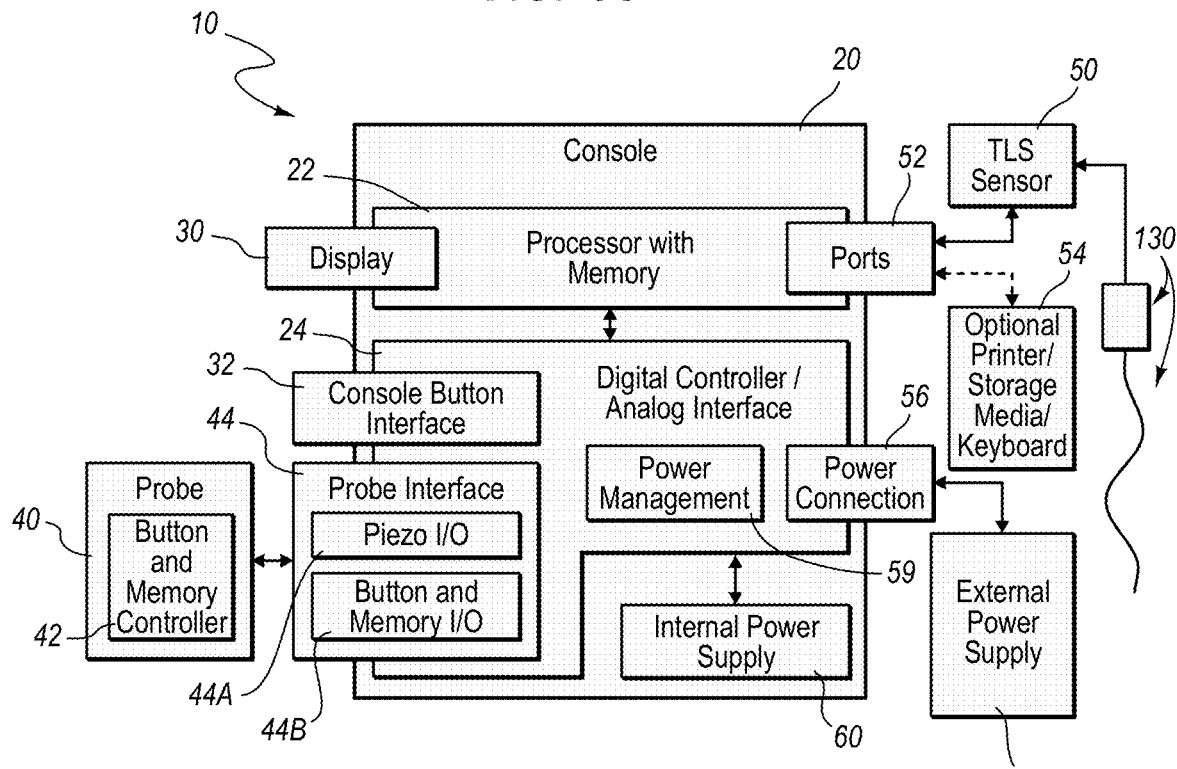
FIG. 9 is a block diagram depicting various elements of an integrated system for intravascular placement of a catheter, according to another example embodiment of the present invention.
Figure 10:
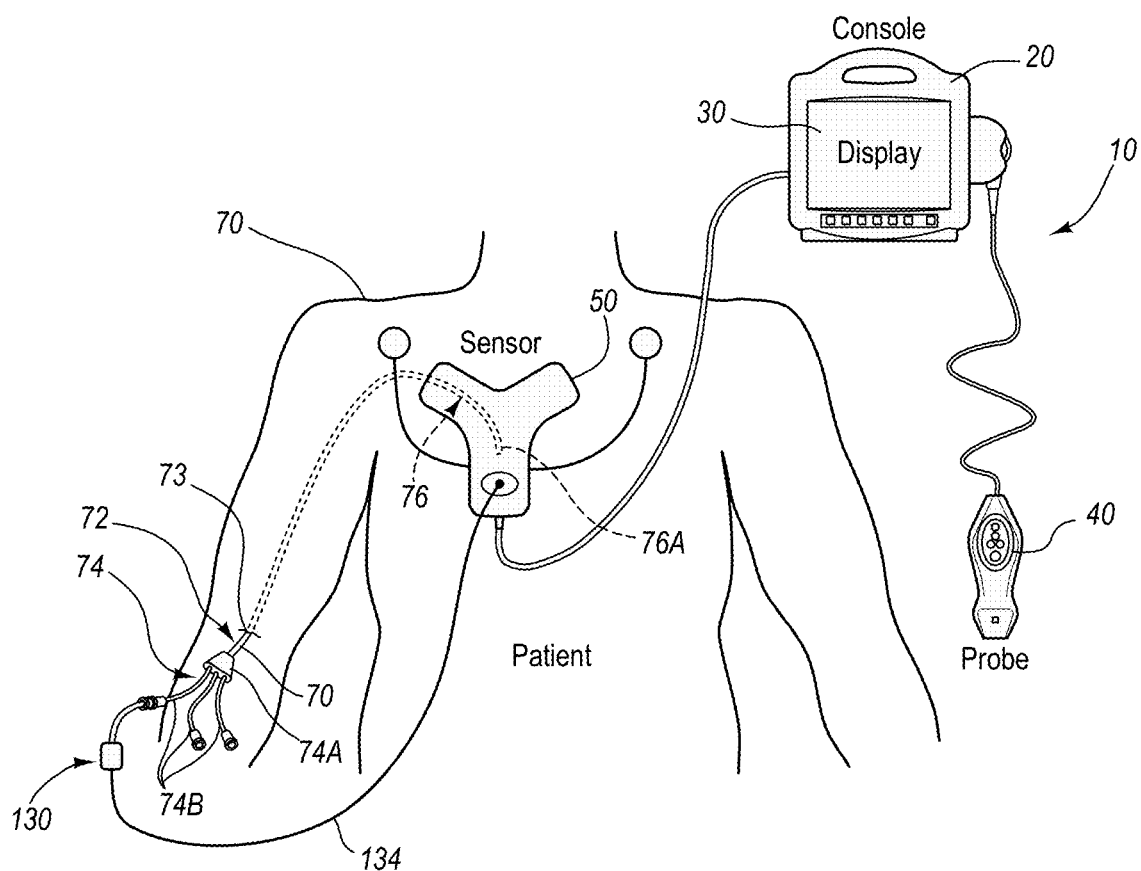
FIG. 10 is a simplified view of a patient and a catheter being inserted therein with assistance of the integrated system of FIG. 9.

Reference is now made to FIGS. 9 and 10 in describing the integrated catheter placement system 10 according to another example embodiment. As before, the integrated system 10 includes the console 20, display 30, probe 40 for US functionality, and the TLS sensor 50 for tip location functionality as described above. Note that the system 10 depicted in FIGS. 9 and 10 is similar in many respects to the system shown in FIGS. 1 and 2. As such, only selected differences will be discussed below. The system 10 of FIGS. 9 and 10 includes additional functionality wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10 and can be employed in concert or individually to assist in catheter placement.

FIGS. 9 and 10 show the addition to the system 10 of a stylet 130 configured in accordance with the present embodiment. As an overview, the catheter stylet 130 is removably predisposed within the lumen of the catheter 72 being inserted into the patient 70 via the insertion site 73. The stylet 130, in addition to including a magnetic assembly for the magnetically-based TLS modality, includes an ECG sensor assembly proximate its distal end and including a portion that is co-terminal with the distal end of the catheter tip for sensing ECG signals produced by the SA node. In contrast to the previous embodiment, the stylet 130 includes a tether 134 extending from its proximal end that operably connects to the TLS sensor 50. As will be described in further detail, the stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality. Reference and ground ECG lead/electrode pairs 158 attach to the body of the body of the patient 70 and are operably attached to the TLS sensor 50 to enable the system to filter out high level electrical activity unrelated to the electrical activity of the SA node of the heart, thus enabling the ECG-based tip confirmation functionality. Together with the reference and ground signals received from the ECG lead/electrode pairs 158 placed on the patient's skin, the ECG signals sensed by the stylet ECG sensor assembly are received by the TLS sensor 50 positioned on the patient's chest (FIG. 10). The TLS sensor 50 and/or console processor 22 can process the ECG signal data to produce an electrocardiogram waveform on the display 30, as will be described. In the case where the TLS sensor 50 processes the ECG signal data, a processor is included therein to perform the intended functionality. If the console 20 processes the ECG signal data, the processor 22, controller 24, or other processor can be utilized in the console to process the data.

Thus, as it is advanced through the patient vasculature, the catheter 72 equipped with the stylet 130 as described above can advance under the TLS sensor 50, which is positioned on the chest of the patient as shown in FIG. 10. This enables the TLS sensor 50 to detect the position of the magnetic assembly of the stylet 130, which is substantially co-terminal with the distal tip 76A of the catheter as located within the patient's vasculature. The detection by the TLS sensor 50 of the stylet magnetic assembly is depicted on the display 30 during ECG mode. The display 30 further depicts during ECG mode an ECG electrocardiogram waveform produced as a result of patient heart's electrical activity as detected by the ECG sensor assembly of the stylet 130. In greater detail, the ECG electrical activity of the SA node, including the P-wave of the waveform, is detected by the ECG sensor assembly of the stylet (described below) and forwarded to the TLS sensor 50 and console 20. The ECG electrical activity is then processed for depiction on the display 30. clinician placing the catheter can then observe the ECG data to determine optimum placement of the distal tip 76A of the catheter 72, such as proximate the SA node in one embodiment. In one embodiment, the console 20 which includes the electronic components, such as the processor 22 (FIG. 9) necessary to receive and process the signals detected by the stylet ECG sensor assembly. In another embodiment, the TLS sensor 50 can include the necessary electronic components processing the ECG signals.

As already discussed, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons 84 included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

Figure 11:
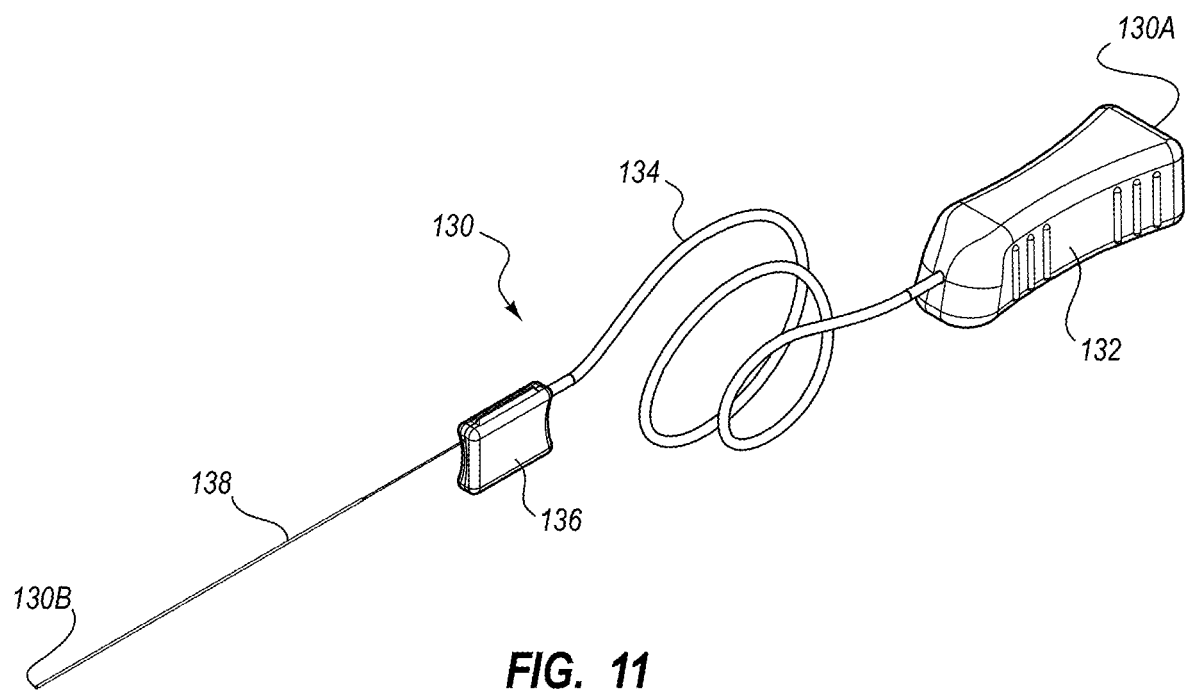
FIG. 11 is a perspective view of a stylet employed in connection with the integrated system of FIG. 9 in placing a catheter within a patient vasculature.
Figure 12A:
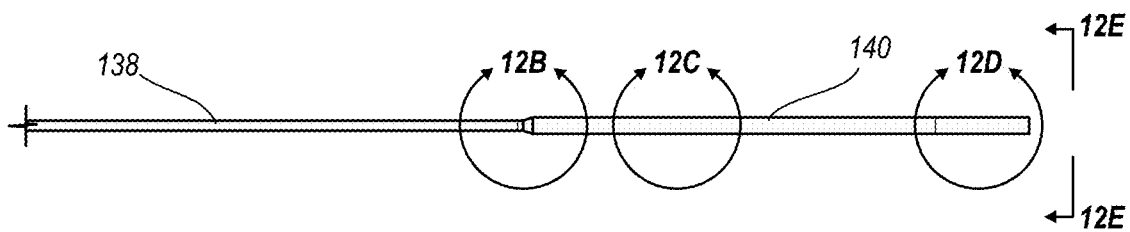
FIGS. 12A-12E are various views of portions of the stylet of FIG. 11.
Figure 12B:
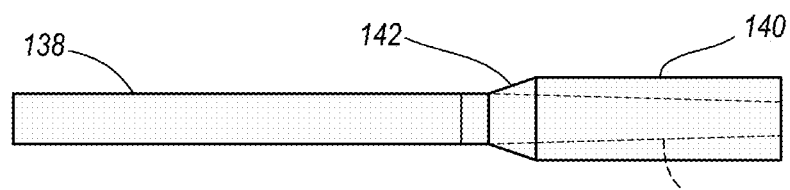
Figure 12C:
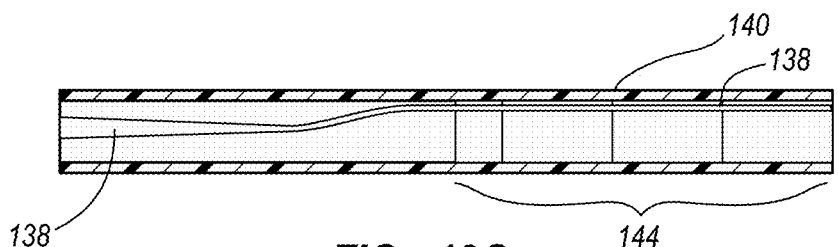
Figure 12D:
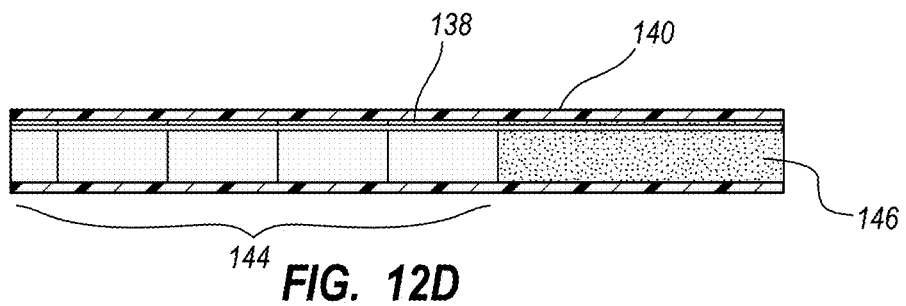
Figure 12E:
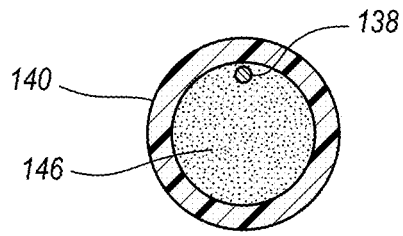

Reference is now made to FIGS. 11-12E in describing various details of one embodiment of the stylet 130 that is removably loaded into the catheter 72 and employed during insertion to position the distal tip 76A of the catheter in a desired location within the patient vasculature. As shown, the stylet 130 as removed from the catheter defines a proximal end 130A and a distal end 130B. A connector 132 is included at the proximal stylet end 130A, and a tether 134 extends distally from the connector and attaches to a handle 136. A core wire 138 extends distally from the handle 136. The stylet 130 is pre-loaded within a lumen of the catheter 72 in one embodiment such that the distal end 130B is substantially flush, or co-terminal, with the catheter opening at the distal end 76A thereof (FIG. 10), and such that a proximal portion of the core wire 138, the handle 136, and the tether 134 extend proximally from a selected one of the extension tubes 74B. Note that, though described herein as a stylet, in other embodiments a guidewire or other catheter guiding apparatus could include the principles of the embodiment described herein.

The core wire 138 defines an elongate shape and is composed of a suitable stylet material including stainless steel or a memory material such as, in one embodiment, a nickel and titanium-containing alloy commonly known by the acronym "nitinol." Though not shown here, manufacture of the core wire 138 from nitinol in one embodiment enables the portion of the core wire corresponding to a distal segment of the stylet to have a pre-shaped bent configuration so as to urge the distal portion of the catheter 72 into a similar bent configuration. In other embodiments, the core wire includes no pre-shaping. Further, the nitinol construction lends torqueability to the core wire 138 to enable a distal segment of the stylet 130 to be manipulated while disposed within the lumen of the catheter 72, which in turn enables the distal portion of the catheter to be navigated through the vasculature during catheter insertion.

The handle 136 is provided to enable insertion/removal of the stylet from the catheter 72. In embodiments where the stylet core wire 138 is torqueable, the handle 136 further enables the core wire to be rotated within the lumen of the catheter 72, to assist in navigating the catheter distal portion through the vasculature of the patient 70.

The handle 136 attaches to a distal end of the tether 134. In the present embodiment, the tether 134 is a flexible, shielded cable housing one or more conductive wires electrically connected both to the core wire 138, which acts as the ECG sensor assembly referred to above, and the tether connector 132. As such, the tether 134 provides a conductive pathway from the distal portion of the core wire 138 through to the tether connector 132 at proximal end 130A of the stylet 130. As will be explained, the tether connector 132 is configured for operable connection to the TLS sensor 50 on the patient's chest for assisting in navigation of the catheter distal tip 76A to a desired location within the patient vasculature.

As seen in FIGS. 12B-12D, a distal portion of the core wire 138 is gradually tapered, or reduced in diameter, distally from a junction point 142. A sleeve 140 is slid over the reduced-diameter core wire portion. Though of relatively greater diameter here, the sleeve in another embodiment can be sized to substantially match the diameter of the proximal portion of the stylet core wire. The stylet 130 further includes a magnetic assembly disposed proximate the distal end 130B thereof for use during TLS mode. The magnetic assembly in the illustrated embodiment includes a plurality of magnetic elements 144 interposed between an outer surface of the reduced-diameter core wire 138 and an inner surface of the sleeve 140 proximate the stylet distal end 130B. In the present embodiment, the magnetic elements 144 include 20 ferromagnetic magnets of a solid cylindrical shape stacked end-to-end in a manner similar to the stylet 100 of FIG. 2. In other embodiments, however, the magnetic element(s) may vary from this design in not only shape, but also composition, number, size, magnetic type, and position in the stylet. For example, in one embodiment the plurality of magnets of the magnetic assembly is replaced with an electromagnetic coil that produces a magnetic field for detection by the TLS sensor. These and other variations are therefore contemplated by embodiments of the present invention.

The magnetic elements 144 are employed in the stylet 130 distal portion to enable the position of the stylet distal end 130B to be observable relative to the TLS sensor 50 placed on the patient's chest. As has been mentioned, the TLS sensor 50 is configured to detect the magnetic field of the magnetic elements 144 as the stylet advances with the catheter 72 through the patient vasculature. In this way, a clinician placing the catheter 72 is able to generally determine the location of the catheter distal end 76A within the patient vasculature and detect when catheter malposition is occurring, such as advancement of the catheter along an undesired vein, for instance.

The stylet 130 further includes the afore-mentioned ECG sensor assembly, according to one embodiment. The ECG sensor assembly enables the stylet 130, disposed in a lumen of the catheter 72 during insertion, to be employed in detecting an intra-atrial ECG signal produced by an SA or other node of the patient's heart, thereby allowing for navigation of the distal tip 76A of the catheter 72 to a predetermined location within the vasculature proximate the patient's heart. Thus, the ECG sensor assembly serves as an aide in confirming proper placement of the catheter distal tip 76A.

In the embodiment illustrated in FIGS. 11-12E, the ECG sensor assembly includes a distal portion of the core wire 138 disposed proximate the stylet distal end 130B. The core wire 138, being electrically conductive, enables ECG signals to be detected by the distal end thereof and transmitted proximally along the core wire. A conductive material 146, such as a conductive epoxy, fills a distal portion of the sleeve 140 adjacent the distal termination of the core wire 138 so as to be in conductive communication with the distal end of the core wire. This in turn increases the conductive surface of the distal end 130B of the stylet 130 so as to improve its ability to detect ECG signals.

Before catheter placement, the stylet 130 is loaded into a lumen of the catheter 72. Note that the stylet 130 can come preloaded in the catheter lumen from the manufacturer, or loaded into the catheter by the clinician prior to catheter insertion. The stylet 130 is disposed within the catheter lumen such that the distal end 130B of the stylet 130 is substantially co-terminal with the distal tip 76A of the catheter 72, thus placing the distal tips of both the stylet and the catheter in substantial alignment with one another. The co-terminality of the catheter 72 and stylet 130 enables the magnetic assembly to function with the TLS sensor 50 in TLS mode to track the position of the catheter distal tip 76A as it advances within the patient vasculature, as has been described. Note, however, that for the tip confirmation functionality of the system 10, the distal end 130B of the stylet 130 need not be co-terminal with the catheter distal end 76A. Rather, all that is required is that a conductive path between the vasculature and the ECG sensor assembly, in this case the core wire 138, be established such that electrical impulses of the SA node or other node of the patient's heart can be detected. This conductive path in one embodiment can include various components including saline solution, blood, etc.

In one embodiment, once the catheter 72 has been introduced into the patient vasculature via the insertion site 73 (FIG. 10) the TLS mode of the system 10 can be employed as already described to advance the catheter distal tip 76A toward its intended destination proximate the SA node. Upon approaching the region of the heart, the system 10 can be switched to ECG mode to enable ECG signals emitted by the SA node to be detected. As the stylet-loaded catheter is advanced toward the patient's heart, the electrically conductive ECG sensor assembly, including the distal end of the core wire 138 and the conductive material 146, begins to detect the electrical impulses produced by the SA node. As such, the ECG sensor assembly serves as an electrode for detecting the ECG signals. The elongate core wire 138 proximal to the core wire distal end serves as a conductive pathway to convey the electrical impulses produced by the SA node and received by the ECG sensor assembly to the tether 134.

The tether 134 conveys the ECG signals to the TLS sensor 50 temporarily placed on the patient's chest. The tether 134 is operably connected to the TLS sensor 50 via the tether connector 132 or other suitable direct or indirect connective configuration. As described, the ECG signal can then be process and depicted on the system display 30 (FIG. 9, 10). Monitoring of the ECG signal received by the TLS sensor 50 and displayed by the display 30 enables a clinician to observe and analyze changes in the signal as the catheter distal tip 76A advances toward the SA node. When the received ECG signal matches a desired profile, the clinician can determine that the catheter distal tip 76A has reached a desired position with respect to the SA node. As mentioned, in one embodiment this desired position lies within the lower one-third ($\frac{1}{3}_{rd}$) portion of the SVC.

The ECG sensor assembly and magnetic assembly can work in concert in assisting a clinician in placing a catheter within the vasculature. Generally, the magnetic assembly of the stylet 130 assists the clinician in generally navigating the vasculature from initial catheter insertion so as to place the distal end 76A of the catheter 72 in the general region of the patient's heart. The ECG sensor assembly can then be employed to guide the catheter distal end 76A to the desired location within the SVC by enabling the clinician to observe changes in the ECG signals produced by the heart as the stylet ECG sensor assembly approaches the SA node. Again, once a suitable ECG signal profile is observed, the clinician can determine that the distal ends of both the stylet 130 and the catheter 72 have arrived at the desired location with respect to the patient's heart. Once it has been positioned as desired, the catheter 72 may be secured in place and the stylet 130 removed from the catheter lumen. It is noted here that the stylet may include one of a variety of configurations in addition to what is explicitly described herein. In one embodiment, the stylet can attach directly to the console instead of an indirect attachment via the TLS sensor. In another embodiment, the structure of the stylet 130 that enables its TLS and ECG-related functionalities can be integrated into the catheter structure itself. For instance, the magnetic assembly and/or ECG sensor assembly can, in one embodiment, be incorporated into the wall of the catheter.

FIGS. 13A-15 describe various details relating to the passage of ECG signal data from the stylet tether 134 to the TLS sensor 50 positioned on the patient's chest, according the present embodiment. In particular, this embodiment is concerned with passage of ECG signal data from a sterile field surrounding the catheter 72 and insertion site 73, which includes the stylet 130 and tether 134, and a non-sterile field, such as the patient's chest on which the TLS sensor is positioned. Such passage should not disrupt the sterile field so that the sterility thereof is compromised. A sterile drape that is positioned over the patient 70 during the catheter insertion procedure defines the majority of the sterile field: areas above the drape are sterile, while areas below (excluding the insertion site and immediately surrounding region) are non-sterile. As will be seen, the discussion below includes at least a first communication node associated with the stylet 130, and a second communication node associated with the TLS sensor 50 that operably connect with one another to enable ECG signal data transfer therebetween.

Figure 13A:
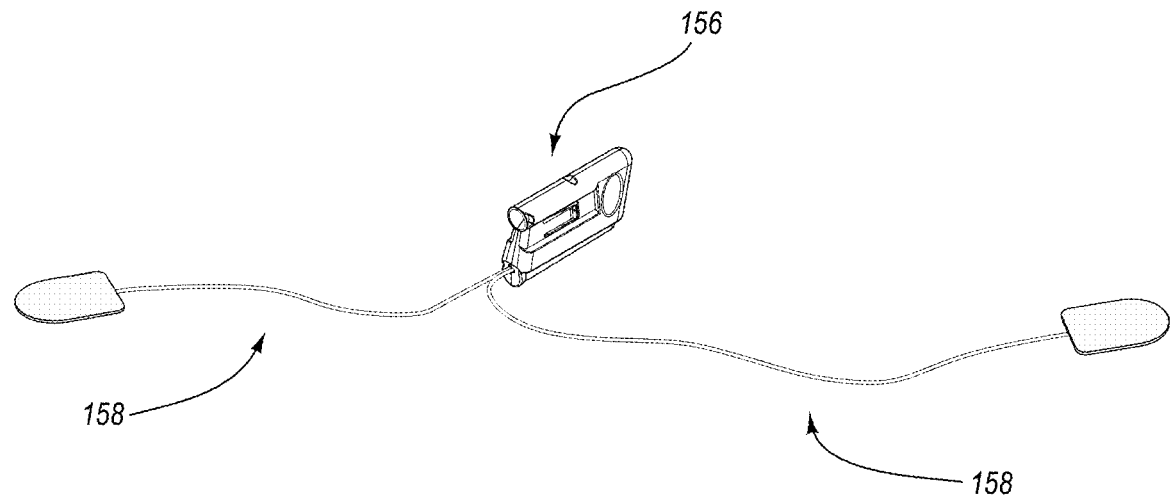
FIGS. 13A-13D are various views of a fin connector assembly for use with the integrated system of FIG. 9.
Figure 13B:
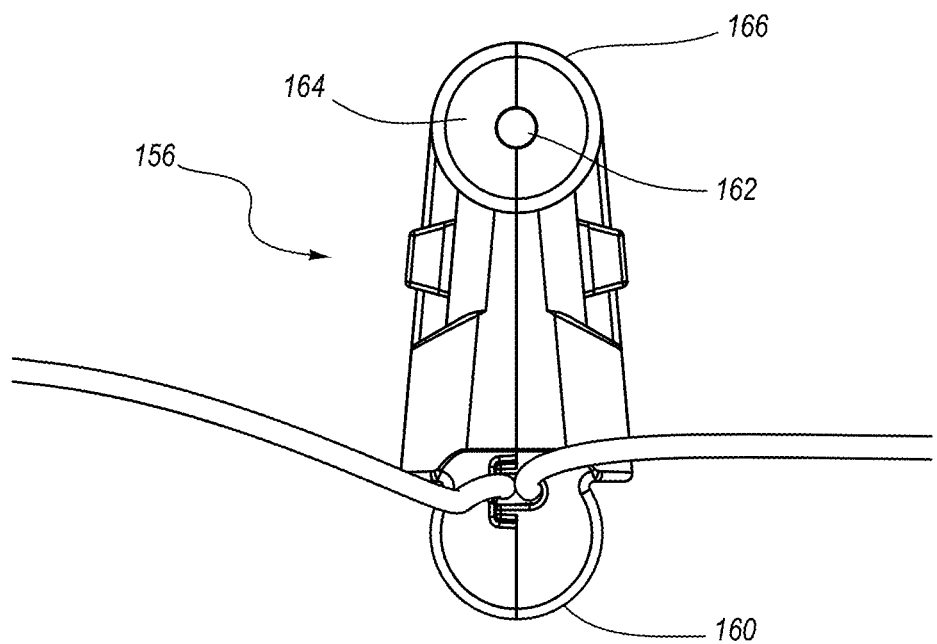
Figure 13C:
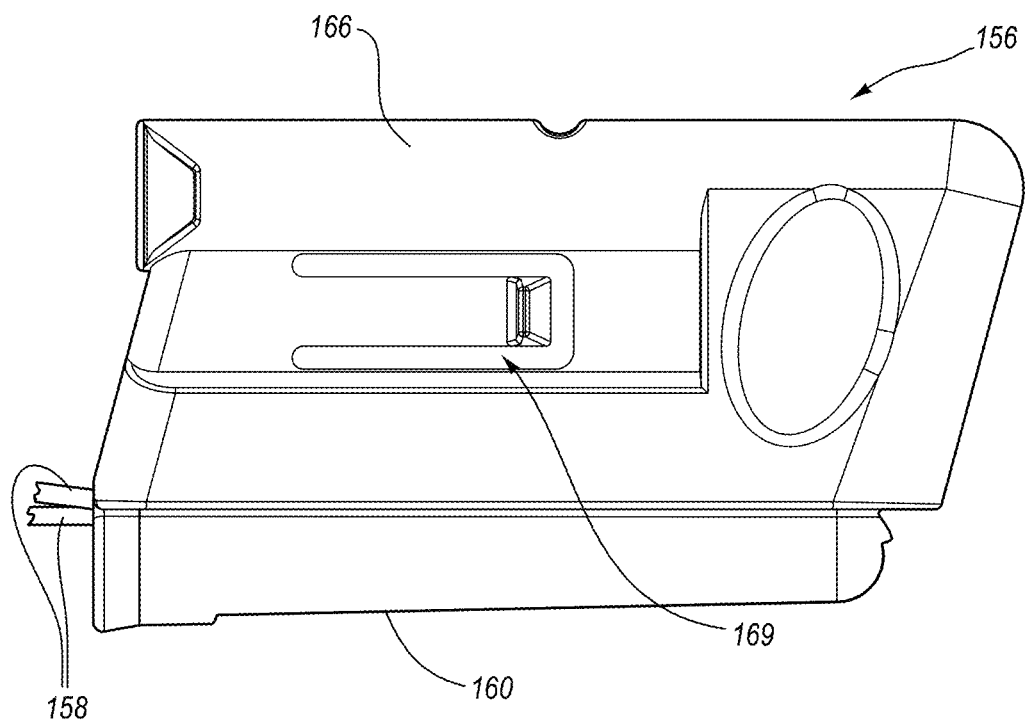
Figure 13D:
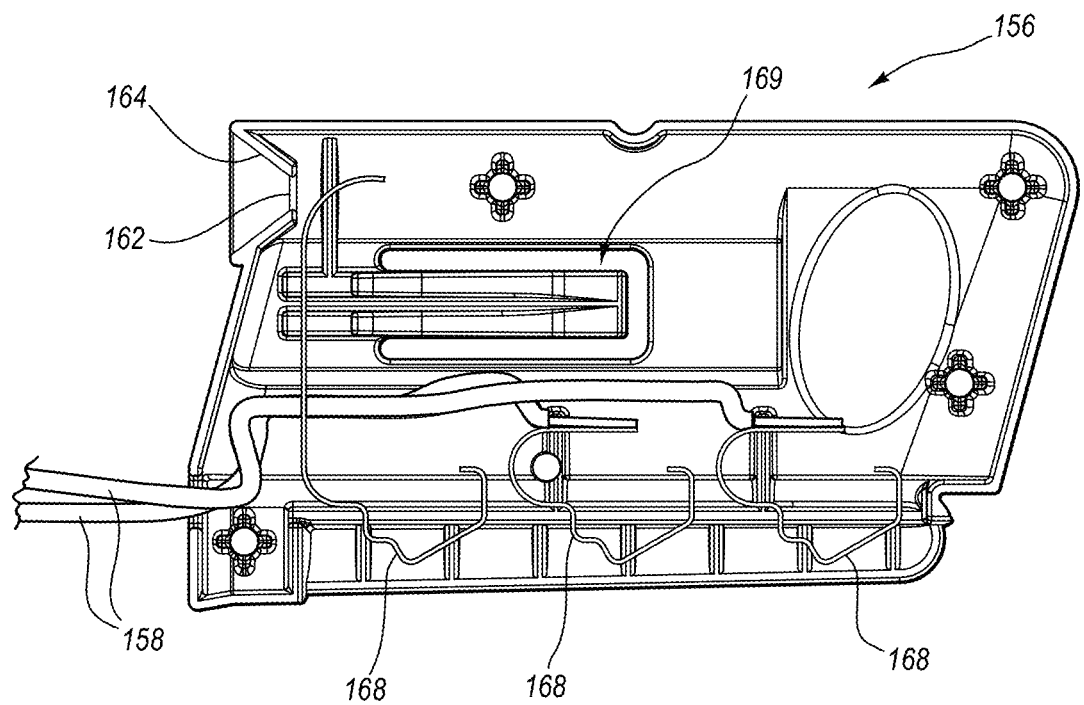
Figure 14A:
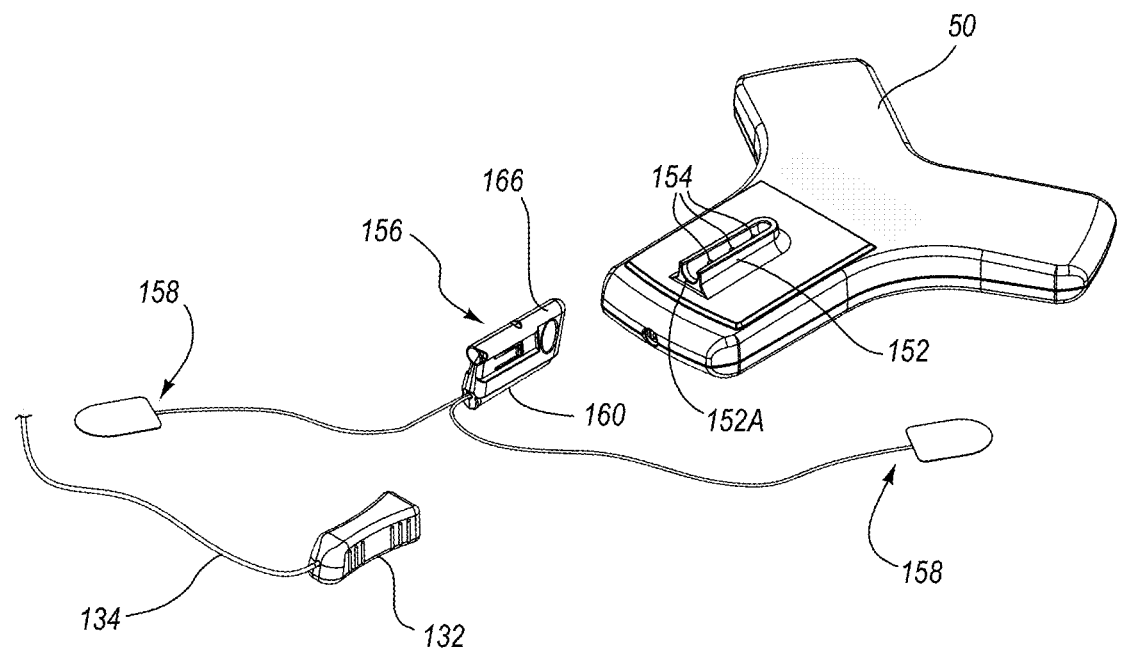
FIGS. 14A-14C are views showing the connection of a stylet tether and fin connector to a sensor of the integrated system of FIG. 9.
Figure 14B:
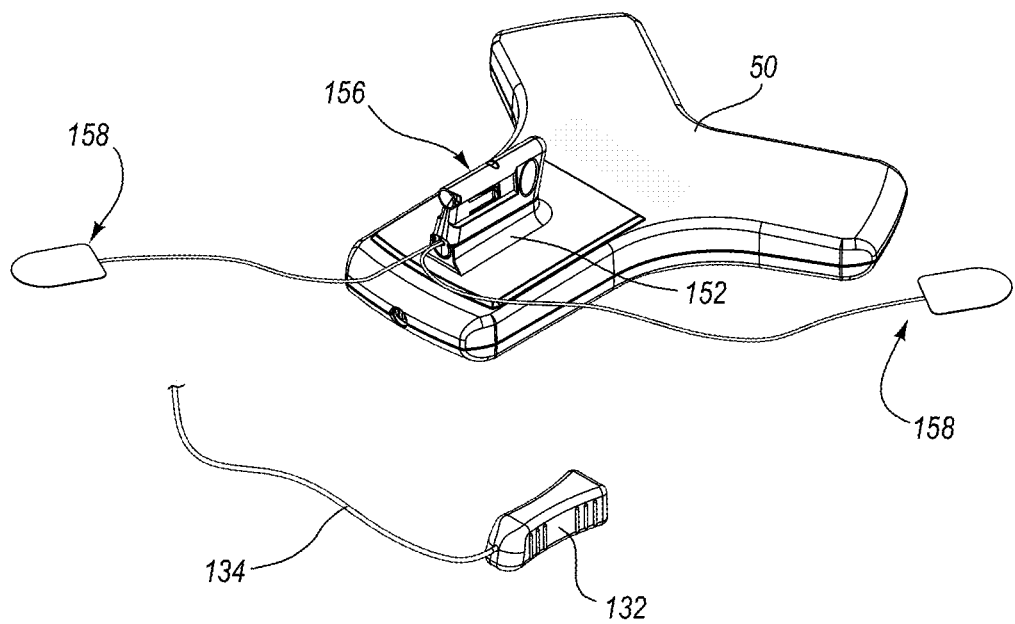
Figure 14C:
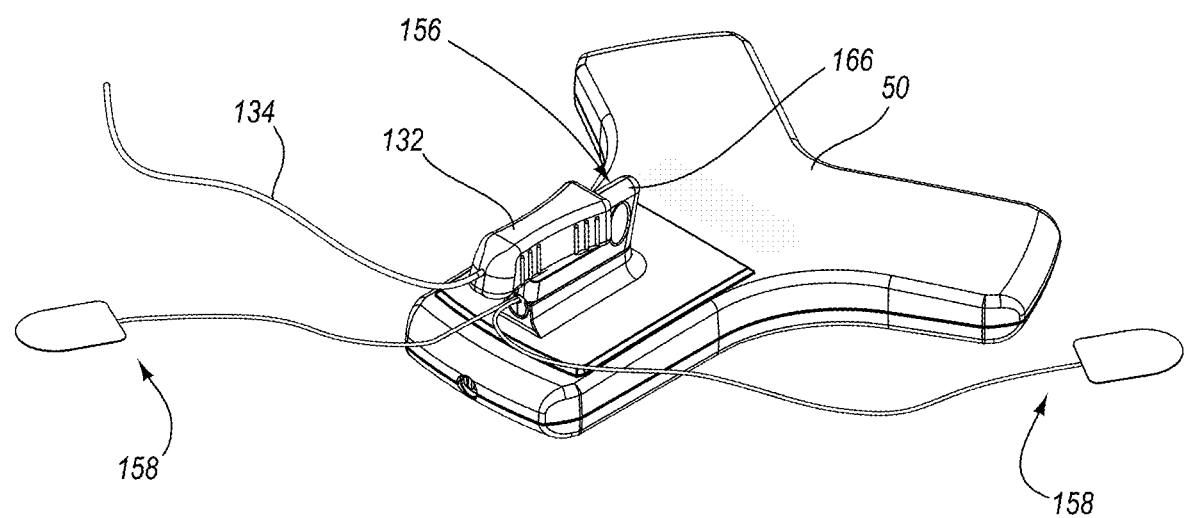
Figure 15:
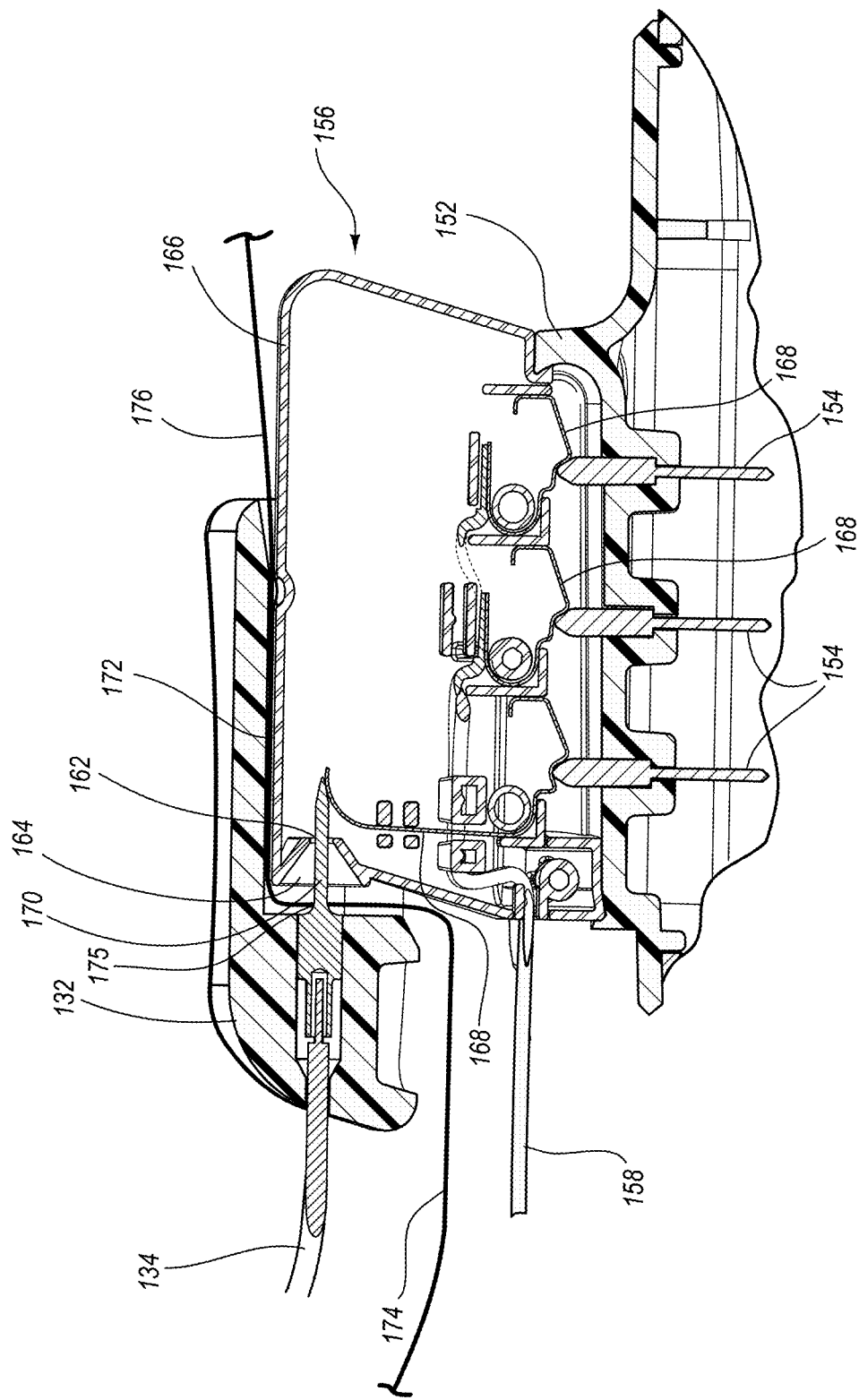
FIG. 15 is a cross sectional view of the connection of the stylet tether, fin connector, and sensor shown in FIG. 14C.

One embodiment addressing the passage of ECG signal data from the sterile field to the non-sterile field without compromising the sterility of the former is depicted in FIGS. 13A-15, which depict a "through-drape" implementation also referred to as a "shark fin" implementation. In particular, FIG. 14A shows the TLS sensor 50 as described above for placement on the chest of the patient during a catheter insertion procedure. The TLS sensor 50 includes on a top surface thereof a connector base 152 defining a channel 152A in which are disposed three electrical base contacts 154. A fin connector 156, also shown in FIGS. 13A-13D, is sized to be slidingly received by the channel 152A of the connector base 152, as shown in FIG. 14B and 15. Two ECG lead/electrode pairs 158 extend from the fin connector 156 for placement on the shoulder and torso or other suitable external locations on the patient body. The drape-piercing tether connector 132 is configured to slidingly mate with a portion of the fin connector 156, as will be described further below, to complete a conductive pathway from the stylet 120, through the sterile field to the TLS sensor 50.

FIGS. 13A-13D show further aspects of the fin connector 156. In particular, the fin connector 156 defines a lower barrel portion 160 that is sized to be received in the channel 152A of the connector base 152 (FIGS. 14B, 15). A hole 162 surrounded by a centering cone 164 is included on a back end of an upper barrel portion 166. The upper barrel portion 166 is sized to receive the tether connector 132 of the stylet 130 (FIGS. 14C, 15) such that a pin contact 170 extending into a channel 172 of the tether connector 132 (FIG. 15) is guided by the centering hole until it seats within the hole 162 of the fin connector 156, thus interconnecting the tether connector with the fin connector. An engagement feature, such as the engagement feature 169 shown in FIGS. 13C and 13D, can be included on the fin connector 156 to engage with a corresponding feature on the tether connector 132 to assist with maintaining a mating between the two components.

FIG. 13D shows that the fin connector 156 includes a plurality of electrical contacts 168. In the present embodiment, three contacts 168 are included: the two forward-most contact each electrically connecting with a terminal end of one of the ECG leads 158, and the rear contact extending into axial proximity of the hole 162 so as to electrically connect with the pin contact 170 of the tether connector 132 when the latter is mated with the fin connector 156 (FIG. 15). A bottom portion of each contact 168 of the fin connector 156 is positioned to electrically connect with a corresponding one of the base contacts 154 of the TLS sensor connector base 152.

FIG. 14B shows a first connection stage, wherein the fin connector 156 is removably mated with the TLS sensor connector base 152 by the sliding engagement of the lower barrel portion 160 of the fin connector with the connector base channel 152A. This engagement electrically connects the connector base contacts 154 with the corresponding fin contacts 168.

FIG. 14C shows a second connection stage, wherein the tether connector 132 is removably mated with the fin connector 156 by the sliding engagement of the tether connector channel 172 with the upper barrel portion 166 of the fin connector. This engagement electrically connects the tether connector pin contact 170 with the back contact 168 of the fin connector 156, as best seen in FIG. 15. In the present embodiment, the horizontal sliding movement of the tether connector 132 with respect to the fin connector 156 is in the same engagement direction as when the fin connector is slidably mated to the sensor connector base channel 152A (FIG. 14B). In one embodiment, one or both of the stylet 130/tether connector 132 and the fin connector 156 are disposable. Also, the tether connector in one embodiment can be mated to the fin connector after the fin connector has been mated to the TLS sensor, while in another embodiment the tether connector can be first mated to the fin connector through the surgical drape before the fin connector is mated to the TLS sensor.

In the connection scheme shown in FIG. 14C, the stylet 130 is operably connected to the TLS sensor 50 via the tether connector 132, thus enabling the ECG sensor assembly of the stylet to communicate ECG signals to the TLS sensor. In addition, the ECG lead/electrode pairs 158 are operably connected to the TLS sensor 50. In one embodiment, therefore, the tether connector 132 is referred to as a first communication node for the stylet 130, while the fin connector 156 is referred to as a second communication node for the TLS sensor 50.

Note that various other connective schemes and structures can be employed to establish operable communication between the stylet and the TLS sensor. For instance, the tether connector can use a slicing contact instead of a pin contact to pierce the drape. Or, the fin connector can be integrally formed with the TLS sensor. These and other configurations are therefore embraced within the scope of embodiments of the present disclosure.

As seen in FIG. 15, a sterile drape 174 used during catheter placement to establish a sterile field is interposed between the interconnection of the tether connector 132 with the fin connector 156. As just described, the tether connector 132 includes the pin contact 170 that is configured to pierce the drape 174 when the two components are mated. This piercing forms a small hole, or perforation 175, in the sterile drape 174 that is occupied by the pin contact 170, thus minimizing the size of the drape perforation by the pin contact. Moreover, the fit between the tether connector 132 and the fin connector 156 is such that the perforation in sterile drape made by piercing of the pin contact 170 is enclosed by the tether connector channel 172, thus preserving the sterility of the drape and preventing a breach in the drape that could compromise the sterile field established thereby. The tether connector channel 172 is configured so as to fold the sterile drape 174 down prior to piercing by the pin contact 170 such that the pin contact does not pierce the drape until it is disposed proximate the hole 162 of the fin connector 156. It is noted here that the tether connector 132 and fin connector 156 are configured so as to facilitate alignment therebetween blindly through the opaque sterile drape 174, i.e., via palpation absent visualization by the clinician of both components.

Note further that the fin contacts 168 of the fin connector 156 as shown in FIG. 15 are configured to mate with the sensor base contacts 154 in such a way as to assist in retaining the fin connector in engagement with the sensor base channel 152A. This in turn reduces the need for additional apparatus to secure the fin connector 156 to the TLS sensor 50.

Figure 16:
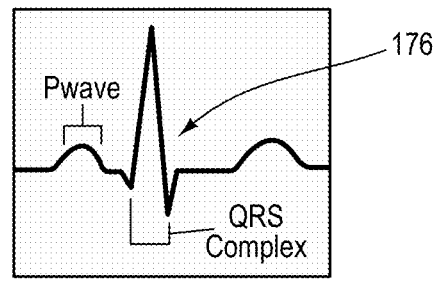
FIG. 16 is simplified view of an ECG trace of a patient.

FIG. 16 shows a typical ECG waveform 176, including a P-wave and a QRS complex. Generally, the amplitude of the P-wave varies as a function of distance of the ECG sensor assembly from the SA node, which produces the waveform 176. A clinician can use this relationship in determining when the catheter tip is properly positioned proximate the heart. For instance, in one implementation the catheter tip is desirably placed within the lower one-third ($\frac{1}{3}_{rd}$) of the superior vena cava, as has been discussed. The ECG data detected by the ECG sensor assembly of the stylet 130 is used to reproduce waveforms such as the waveform 176, for depiction on the display 30 of the system 10 during ECG mode.

Figure 17:
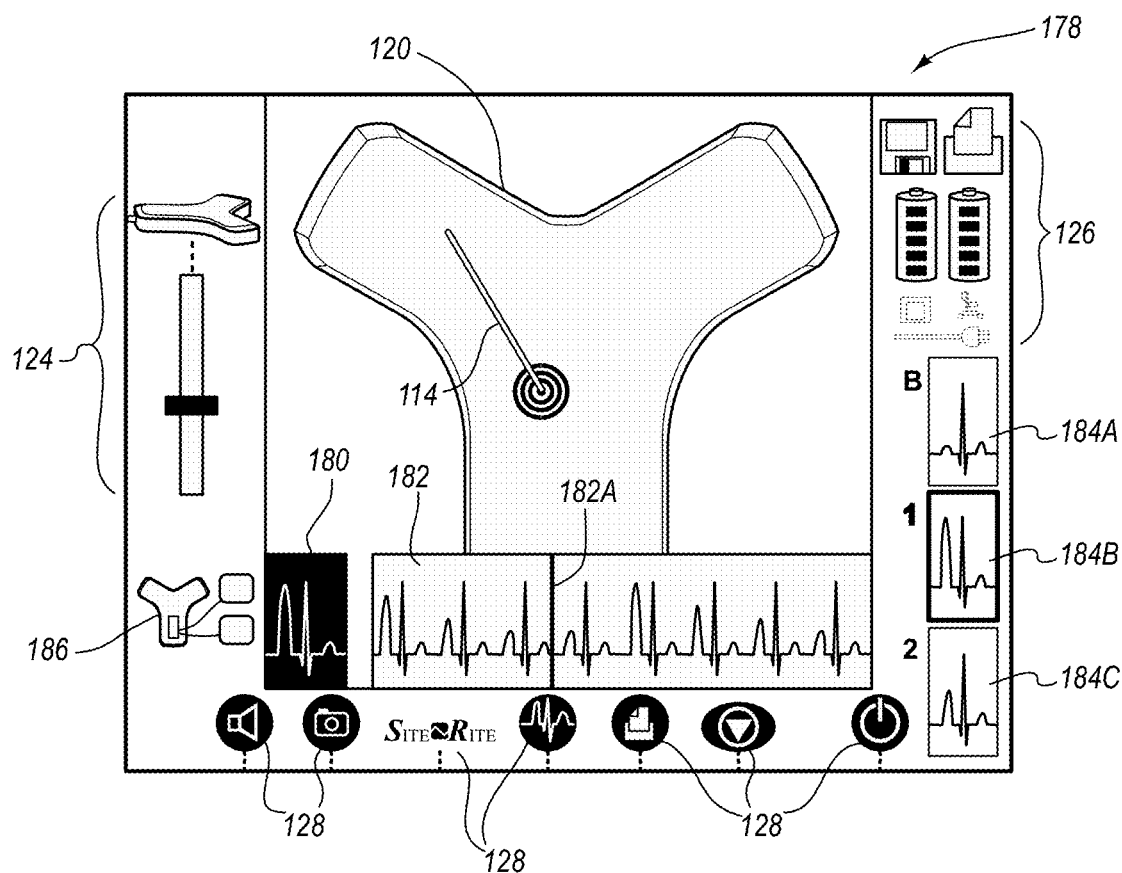
FIG. 17 is a screenshot of an image depicted on a display of the integrated system of FIG. 9 during catheter tip placement procedures.

Reference is now made to FIG. 17 in describing display aspects of ECG signal data on the display 30 when the system 10 is in ECG mode, the third modality described further above, according to one embodiment. The screenshot 178 of the display 30 includes elements of the TLS modality, including a representative image 120 of the TLS sensor 50, and can the icon 114 corresponding to the position of the distal end of the stylet 130 during transit through the patient vasculature. The screenshot 178 further includes a window 180 in which the current ECG waveform captured by the ECG sensor assembly of the stylet 130 and processed by the system 10 is displayed. The window 180 is continually refreshed as new waveforms are detected.

Window 182 includes a successive depiction of the most recent detected ECG waveforms, and includes a refresh bar 182A, which moves laterally to refresh the waveforms as they are detected. Window 184A is used to display a baseline ECG waveform, captured before the ECG sensor assembly is brought into proximity with the SA node, for comparison purposes to assist the clinician in determining when the desired catheter tip location has been achieved. Windows 184B and 184C can be filed by user-selected detected ECG waveforms when the user pushes a predetermined button on the probe 40 or the console button interface 32. The waveforms in the windows 184B and 184C remain until overwritten by new waveforms as a result of user selection via button pushes or other input. As in previous modes, the depth scale 124, status/action indicia 126, and button icons 128 are included on the display 30. An integrity indicator 186 is also included on the display 30 to give an indication of whether the ECG lead/electrode pairs 158 are operably connected to the TLS sensor 50.

As seen above, therefore, the display 30 depicts in one embodiment elements of both the TLS and ECG modalities simultaneously on a single screen, thus offering the clinician ample data to assist in placing the catheter distal tip in a desired position. Note further that in one embodiment a printout of the screenshot or selected ECG or TLS data can be saved, printed, or otherwise preserved by the system 10 to enable documentation of proper catheter placement.

Although the embodiments described herein relate to a particular configuration of a catheter, such as a PICC or CVC, such embodiments are merely exemplary. Accordingly, the principles of the present invention can be extended to catheters of many different configurations and designs.

II. Assisted Guidance for Needle/Medical Component

Embodiments of the present invention described herein are generally directed to a guidance system for locating and guiding a needle or other medical component during ultrasound-based or other suitable procedures for accessing with the needle a subcutaneous vessel of a patient, for instance. In one embodiment, the guidance system enables the position, orientation, and advancement of the needle to be superimposed in real-time atop the ultrasound image of the vessel, thus enabling a clinician to accurately guide the needle to the intended target. Furthermore, in one embodiment, the guidance system tracks the needle's position in five degrees of motion: x, y, and z spatial coordinate space, needle pitch, and needle yaw. Such tracking enables the needle to be guided and placed with relatively high accuracy.

Figure 18:
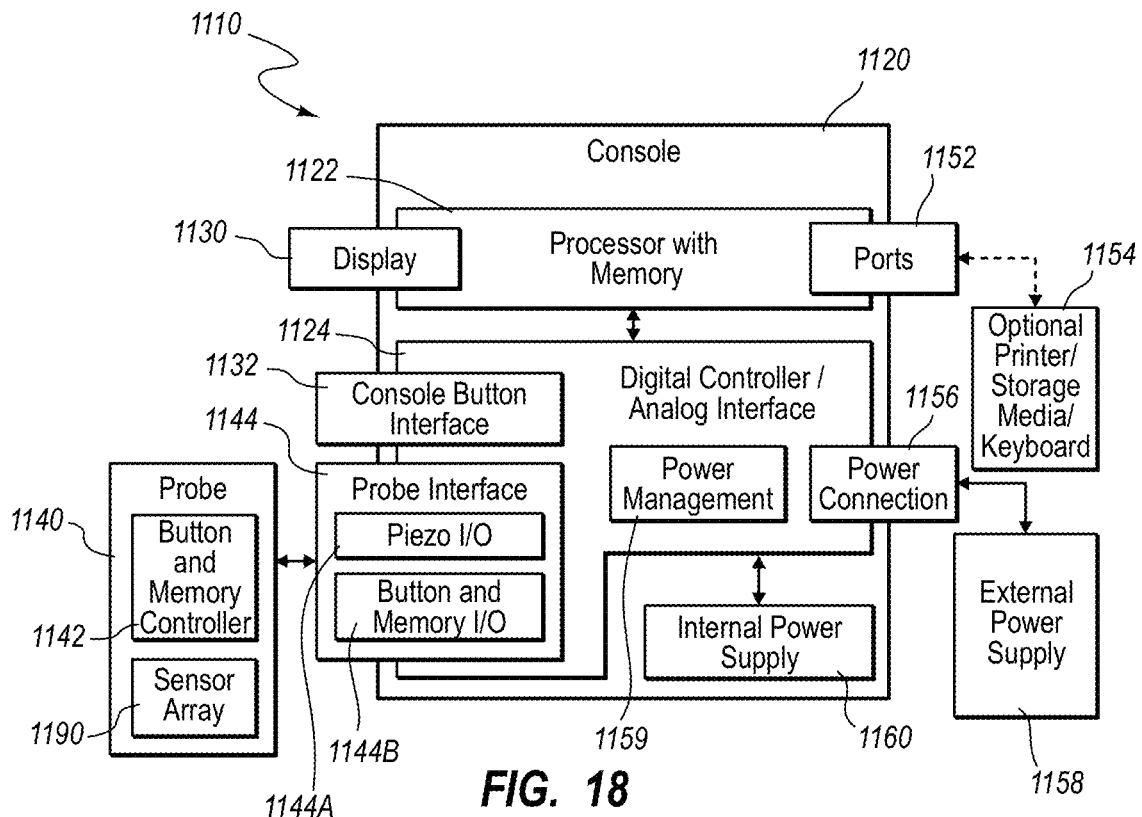
FIG. 18 is a block diagram depicting various elements of an ultrasound-based guidance system for needles and other medical components, according to one embodiment.
Figure 19:
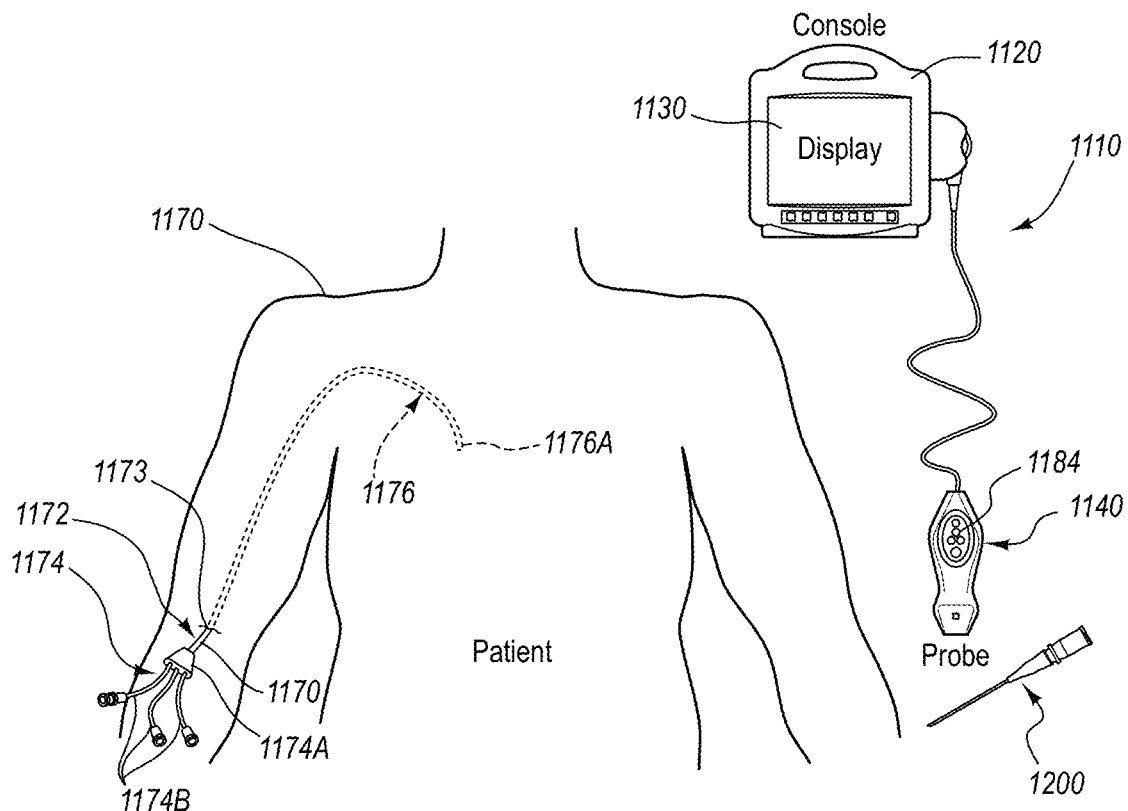
FIG. 19 is a simplified view of a patient and a catheter being inserted therein, showing one possible environment in which the guidance system of FIG. 18 can be practiced.

Reference is first made to FIGS. 18 and 19, which depict various components of an ultrasound-based needle guidance system ("system"), generally designated at 1110, configured in accordance with one embodiment of the present invention. As shown, the system 1110 generally includes an ultrasound ("US") imaging portion including a console 1120, display 1130, and probe 1140, each of which is described in further detail below. Note that the system 1110 bears similarity to the system 10 shown in FIG. 1 with respect to some components, in one embodiment. It should be noted, however, that the ultrasound imaging portion can be configured in one of a variety of ways in addition to what is shown and described herein.

The ultrasound imaging portion of the system 1110 is employed to image a targeted internal portion of a body of a patient prior to percutaneous insertion of a needle or other device to access the target. As described below, in one embodiment insertion of the needle is performed prior to the subsequent insertion of a catheter into a vein or other portion of the vasculature of the patient. It is appreciated, however, that insertion of a needle into the body of a patient can be performed for a variety of medical purposes.

FIG. 19 shows the general relation of the above-described components to a patient 1170 during a procedure to ultimately place a catheter 1172 into the patient vasculature through a skin insertion site 1173, according to one embodiment. FIG. 19 shows that the catheter 1172 generally includes a proximal portion 1174 that remains exterior to the patient and a distal potion 1176 that resides within the patient vasculature after placement is complete. The system 1110 is employed to ultimately position a distal tip 1176A of the catheter 1172 in a desired position within the patient vasculature. In one embodiment, the desired position for the catheter distal tip 1176A is proximate the patient's heart, such as in the lower one-third ($\frac{1}{3}^{rd}$) portion of the Superior Vena Cava ("SVC"). Of course, the system 1110 can be employed to place the catheter distal tip in other locations.

The catheter proximal portion 1174 further includes a hub 1174A that provides fluid communication between the one or more lumens of the catheter 1172 and one or more extension legs 1174B extending proximally from the hub. As mentioned, placement of a needle into the patient vasculature at the insertion site 1173 is typically performed prior to insertion of the catheter, though it is appreciated that other placement methods can be employed. Further, it is appreciated that the above discussion is only one example for use of the system 1110; indeed it can be employed for a variety of uses, such as the placement of needles preparatory to insertion of a catheter as above, the insertion of a needle for other uses, or for the insertion of other medical components into the body of a patient, including x-ray or ultrasound markers, biopsy sheaths, ablation components, bladder scanning components, vena cava filters, etc.

In greater detail, the console 1120 houses a variety of components of the system 1110 and it is appreciated that the console can take one of a variety of forms. A processor 1122, including non-volatile memory such as EEPROM for instance, is included in the console 1120 for controlling system function and executing various algorithms during operation of the system 1110, thus acting as a control processor. A digital controller/analog interface 1124 is also included with the console 1120 and is in communication with both the processor 1122 and other system components to govern interfacing between the probe 1140 and other system components.

The system 1110 further includes ports 1152 for connection with additional components such as optional components 1154 including a printer, storage media, keyboard, etc. The ports in one embodiment are USB ports, though other port types or a combination of port types can be used for this and the other interfaces connections described herein. A power connection 1156 is included with the console 1120 to enable operable connection to an external power supply 1158. An internal battery 1160 can also be employed, either with or exclusive of an external power supply. Power management circuitry 1159 is included with the digital controller/analog interface 1124 of the console to regulate power use and distribution.

The display 1130 in the present embodiment is integrated into the console 1120 and is used to display information to the clinician during the placement procedure, such as an ultrasound image of the targeted internal body portion attained by the probe 1140. In another embodiment, the display may be separate from the console. In one embodiment, a console button interface 1132 and control buttons 1184 (FIG. 19) included on the probe 1140 can be used to immediately call up a desired mode to the display 1130 by the clinician to assist in the placement procedure. In one embodiment, the display 1130 is an LCD device.

FIG. 19 further depicts a needle 1200 used to gain initial access to the patient vasculature via the insertion site 1173. As will be described in further detail below, the needle 1200 is configured to cooperate with the system 1110 in enabling the system to detect the position, orientation, and advancement of the needle during an ultrasound-based placement procedure.

Figure 20:
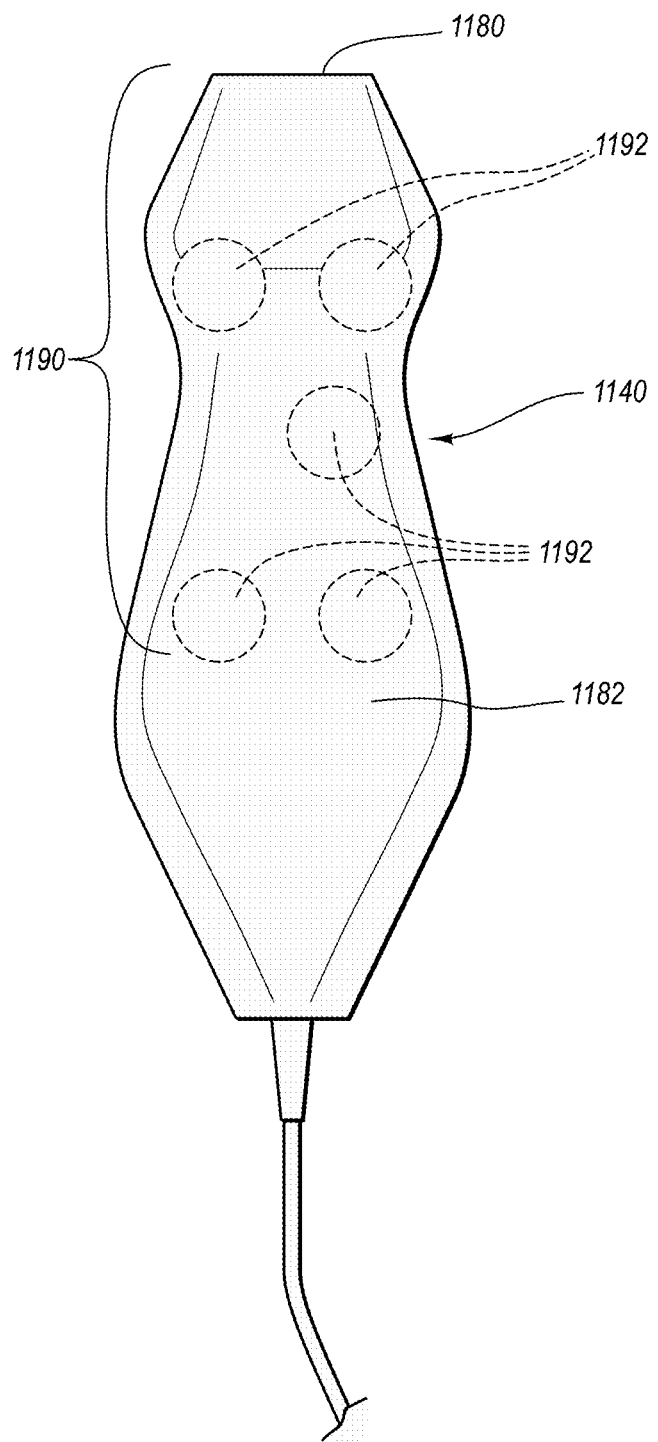
FIG. 20 is a top view of the ultrasound probe of the guidance system of FIG. 18.

FIG. 20 depicts features of the probe 1140 according to one embodiment. The probe 1140 is employed in connection with ultrasound-based visualization of a vessel, such as a vein, in preparation for insertion of the needle 1200 and/or catheter 1172 into the vasculature. Such visualization gives real time ultrasound guidance and assists in reducing complications typically associated with such introduction, including inadvertent arterial puncture, hematoma, pneumothorax, etc.

The handheld probe 1140 includes a head 1180 that houses a piezoelectric array for producing ultrasonic pulses and for receiving echoes thereof after reflection by the patient's body when the head is placed against the patient's skin proximate the prospective insertion site 1173 (FIG. 19). The probe 1140 further includes a plurality of control buttons 1184 (FIG. 19) for controlling the system, thus eliminating the need for the clinician to reach out of the sterile field, which is established about the patient insertion site prior to establishment of the insertion site, to control the system 1110.

As such, in one embodiment a clinician employs the ultrasound imaging portion of the system 1110 to determine a suitable insertion site and establish vascular access, such as with the needle 1200, prior to introduction of the catheter 1172 for ultimate advancement thereof through the vasculature toward an intended destination.

FIG. 18 shows that the probe 1140 further includes a button and memory controller 1142 for governing button and probe operation. The button and memory controller 1142 can include non-volatile memory, such as EEPROM, in one embodiment. The button and memory controller 1142 is in operable communication with a probe interface 1144 of the console 1120, which includes a piezo input/output component 1144A for interfacing with the probe piezoelectric array and a button and memory input/output component 1144B for interfacing with the button and memory controller 1142.

As seen in FIG. 20, the probe 1140 includes a sensor array 1190 for detecting the position, orientation, and movement of the needle 1200 during ultrasound imaging procedures, such as those described above. As will be described in further detail below, the sensor array includes a plurality of magnetic sensors 1192 embedded within the housing of the probe. The sensors 1192 are configured to detect a magnetic field associated with the needle 1200 and enable the system 1110 to track the needle. Though configured here as magnetic sensors, it is appreciated that the sensors 1192 can be sensors of other types and configurations, as will be described. Also, though they are shown in FIG. 20 as included with the probe 1140, the sensors 1192 of the sensor array 1190 can be included in a component separate from the probe, such as a separate handheld device. In the present embodiment, the sensors 1192 are disposed in a planar configuration below a top face 1182 of the probe 1140, though it is appreciated that the sensors can be arranged in other configurations, such as in an arched or semi-circular arrangement.

In the present embodiment, each of the sensors 1192 includes three orthogonal sensor coils for enabling detection of a magnetic field in three spatial dimensions. Such three dimensional ("3-D") magnetic sensors can be purchased, for example, from Honeywell Sensing and Control of Morristown, NJ. Further, the sensors 1192 of the present embodiment are configured as Hall-effect sensors, though other types of magnetic sensors could be employed. Further, instead of 3-D sensors, a plurality of one dimensional magnetic sensors can be included and arranged as desired to achieve 1-, 2-, or 3-D detection capability.

In the present embodiment, five sensors 1192 are included in the sensor array 1190 so as to enable detection of the needle 1200 in not only the three spatial dimensions (i.e., X, Y, Z coordinate space), but also the pitch and yaw orientation of the needle itself. Note that in one embodiment, orthogonal sensing components of two or more of the sensors 1192 enable the pitch and yaw attitude of the magnetic element 1210, and thus the needle 1200, to be determined.

In other embodiments, fewer or more sensors can be employed in the sensor array. More generally, it is appreciated that the number, size, type, and placement of the sensors of the sensor array can vary from what is explicitly shown here.

Figure 21A:
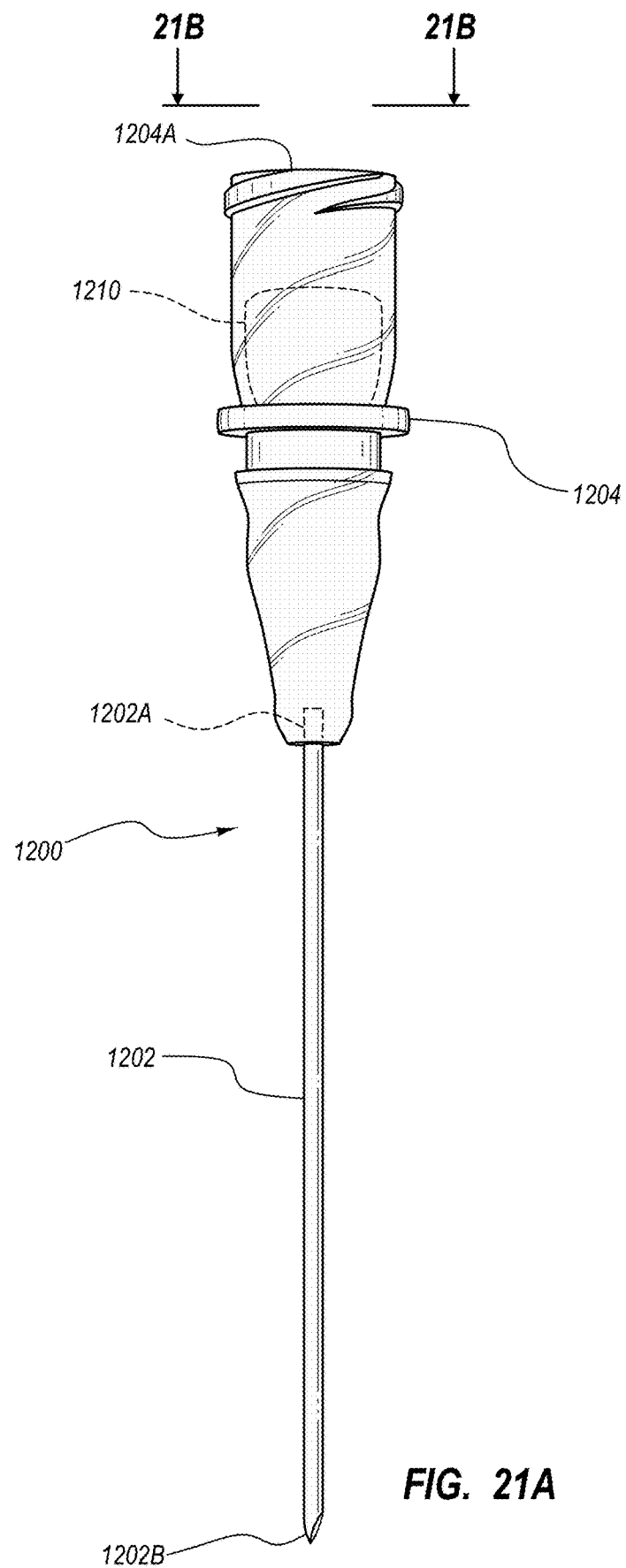
FIG. 21A is a side view of a needle for use with the guidance system of FIG. 18, according to one embodiment.
Figure 21B:
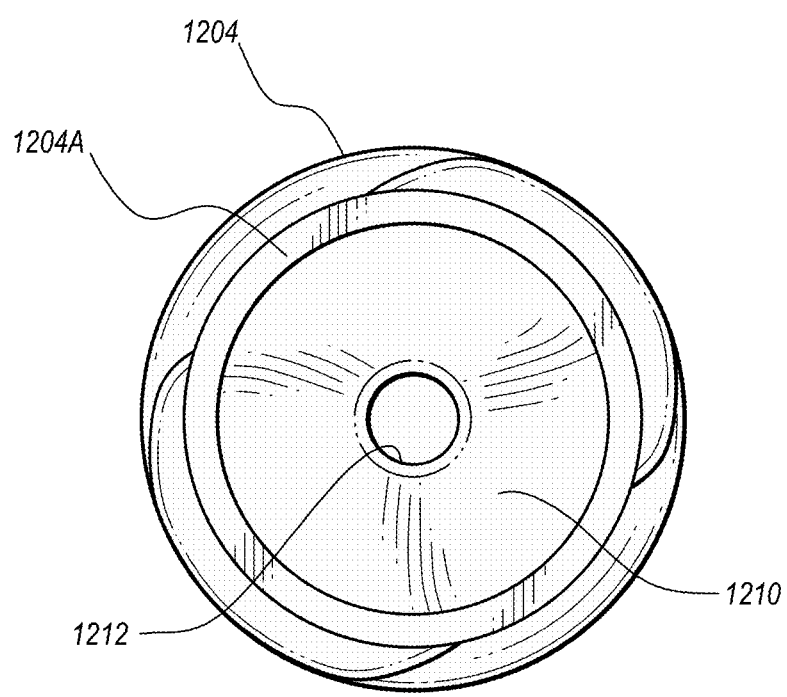
FIG. 21B is an end view of the needle of FIG. 21A.

FIGS. 21A and 21B show details of one example of the needle 1200 that can be used in connection with the guidance system 1110 in accessing a targeted internal body portion of the patient, as shown in FIG. 19, according to one embodiment. In particular, the needle 1200 includes a hollow cannula 1202, which defines a proximal end 1202A and a distal end 1202B. A hub 1204 is attached to the proximal end 1202A of the cannula 1202 and includes an open end 1204A that is configured as a connector for connecting with various devices, in the present embodiment. Indeed, the open end 1204A of the hub 1204 is in communication with the hollow cannula 1202 such that a guide wire, stylet, or other component may be passed through the hub into the cannula.

As shown in FIGS. 21A and 21B, a magnetic element 1210 is included with the hub 1204. As best seen in FIG. 21B, the magnetic element 1210 in the present embodiment is a permanent magnet, including a ferromagnetic substance for instance, and is ring-shaped so as to define hole 1212 that is aligned with the hollow cannula 1202. So configured, the magnetic element 1210 produces a magnetic field that is detectable by the sensor array 1190 of the ultrasound probe 1140 so as to enable the location, orientation, and movement of the needle 1200 to be tracked by the system 1110, as described further below.

In other embodiments, it is appreciated that many other types, numbers, and sizes of magnetic elements can be employed with the needle 1200 or other medical component to enable tracking thereof by the present guidance system.

Figure 22A:
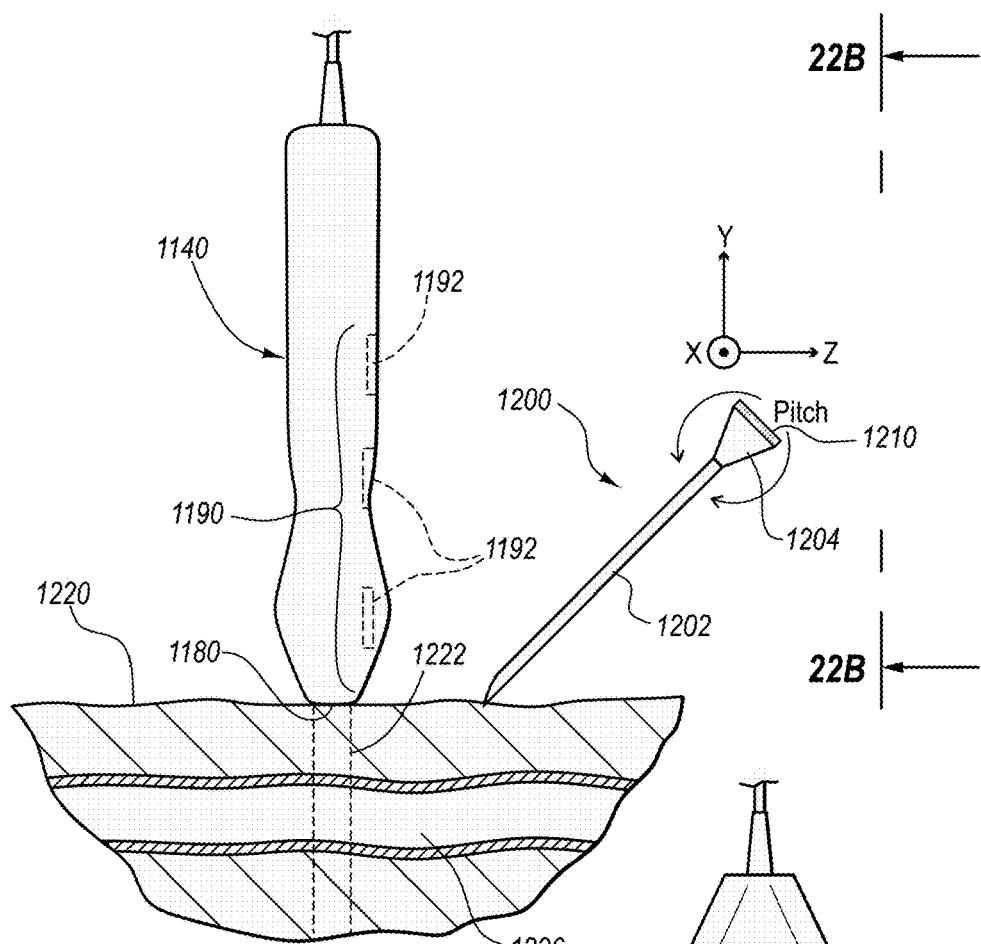
FIGS. 22A and 22B are simplified views of the ultrasound probe of the guidance system being used to guide a needle toward a vessel within the body of a patient.
Figure 22B:
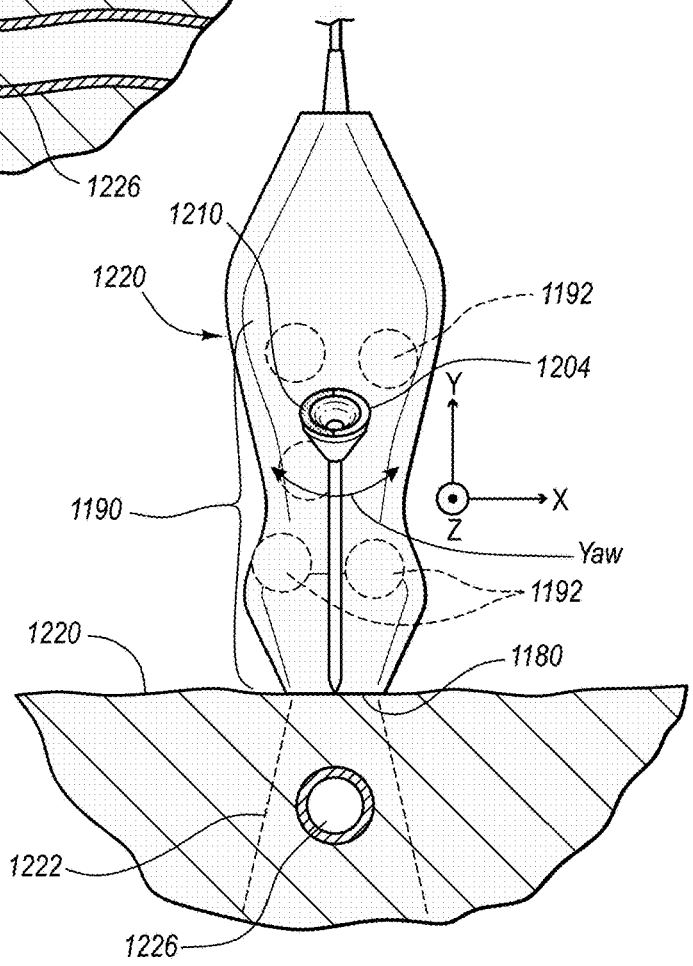

Reference is now made to FIGS. 22A and 22B, which show the ultrasound probe 1140 of the system 1110 and the needle 1200 in position and ready for insertion thereof through a skin surface 1220 of a patient to access a targeted internal body portion. In particular, the probe 1140 is shown with its head 1180 placed against the patient skin and producing an ultrasound beam 1222 so as to ultrasonically image a portion of a vessel 1226 beneath the patient skin surface 1220. The ultrasonic image of the vessel 1226 can be depicted on the display 1130 of the system 1110 (FIG. 19).

As mentioned above, the system 1110 in the present embodiment is configured to detect the position, orientation, and movement of the needle 1200 described above. In particular, the sensor array 1190 of the probe 1140 is configured to detect a magnetic field of the magnetic element 1210 included with the needle 1200. Each of the sensors 1192 of the sensor array 1190 is configured to spatially detect the magnetic element 1210 in three dimensional space. Thus during operation of the system 1110, magnetic field strength data of the needle's magnetic element 1210 sensed by each of the sensors 1192 is forwarded to a processor, such as the processor 1122 of the console 1120 (FIG. 18), which computes in real-time the position and/or orientation of the magnetic element 1210.

Specifically, and as shown in FIGS. 22A and 22B, the position of the magnetic element 1210 in X, Y, and Z coordinate space with respect to the sensor array 1190 can be determined by the system 1110 using the magnetic field strength data sensed by the sensors 1192. Moreover, FIG. 22A shows that the pitch of the magnetic element 1210 can also be determined, while FIG. 22B shows that the yaw of the magnetic element can be determined. Suitable circuitry of the probe 1140, the console 1120, or other component of the system can provide the calculations necessary for such position/orientation. In one embodiment, the magnetic element 210 can be tracked using the teachings of one or more of the following U.S. Pat. Nos. 5,775,322; 5,879,297; 6,129,668; 6,216,028; and 6,263,230. The contents of the aforementioned U.S. patents are incorporated herein by reference in their entireties.

Figure 23A:
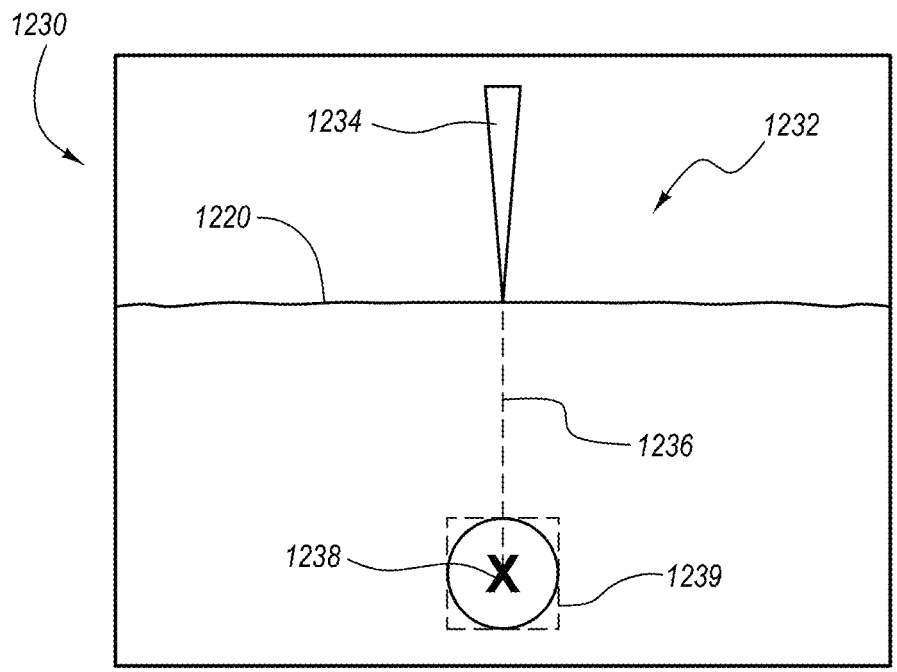
FIGS. 23A and 23B show possible screenshots for depiction on the display of the guidance system, showing the position and orientation of a needle according to one embodiment.
Figure 23B:
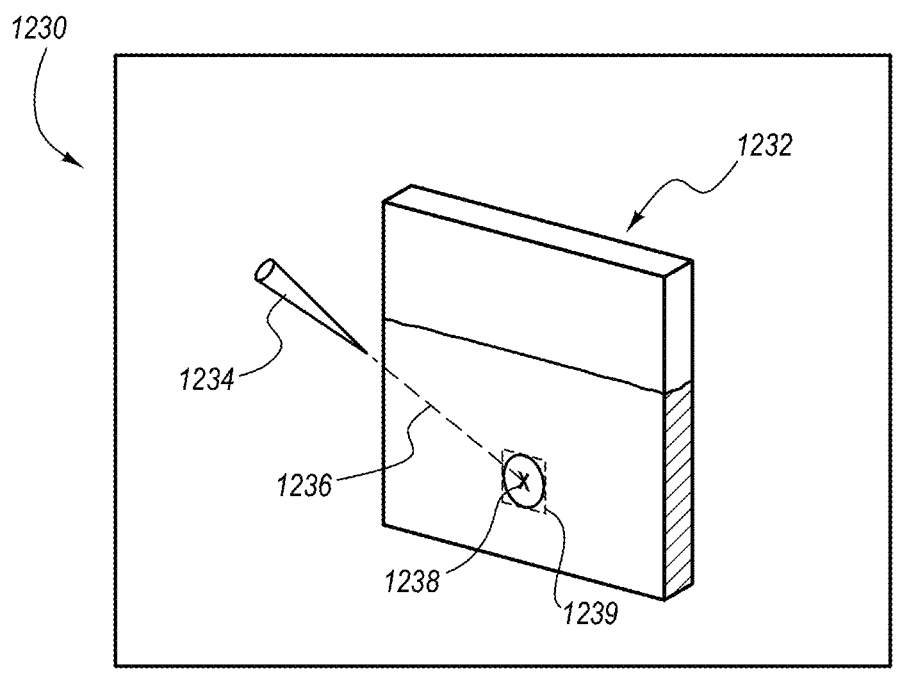

The above position and orientation information determined by the system 1110, together with the length of the cannula 1202 and position of the magnetic element 1210 with respect to the distal needle tip as known by or input into the system, enable the system to accurately determine the location and orientation of the entire length of the needle 1200 with respect to the sensor array 1190. Optionally, the distance between the magnetic element 1210 and the distal needle tip is known by or input into the system 1110. This in turn enables the system 1110 to superimpose an image of the needle 1200 on to an image produced by the ultrasound beam 1222 of the probe 1140. FIGS. 23A and 23B show examples of such a superimposition of the needle onto an ultrasound image. Specifically, FIGS. 23A and 23B each show a screenshot 1230 that can be depicted on the display 1130 (FIG. 19), for instance. In FIG. 23A, an ultrasound image 1232 is shown, including depiction of the patient skin surface 1220, and the subcutaneous vessel 1226. The ultrasound image 1232 corresponds to an image acquired by the ultrasound beam 1222 shown in FIGS. 22A and 22B, for instance.

The screenshot 1230 further shows a needle image 1234 representing the position and orientation of the actual needle 1200 as determined by the system 1110 as described above. Because the system is able to determine the location and orientation of the needle 1200 with respect to the sensor array 1190, the system is able to accurately determine the position and orientation of the needle 1200 with respect to the ultrasound image 1232 and superimpose it thereon for depiction as the needle image 1234 on the display 1130. Coordination of the positioning of the needle image 1234 on the ultrasound image 1232 is performed by suitable algorithms executed by the processor 1122 or other suitable component of the system 1110.

The sensors 1192 are configured to continuously detect the magnetic field of the magnetic element 1210 of the needle 1200 during operation of the system 1110. This enables the system 1110 to continuously update the position and orientation of the needle image 1234 for depiction on the display 1130. Thus, advancement or other movement of the needle 1200 is depicted in real-time by the needle image 1234 on the display 1130. Note that the system 1110 is capable of continuously updating both the ultrasound image 1232 and the needle image 1234 on the display 1130 as movements of the probe 1140 and the needle 1200 occur during a placement procedure or other activity.

FIG. 23A further shows that in one embodiment the system 1110 can depict a projected path 1236 based on the current position and orientation of the needle 1200 as depicted by the needle image 1234. The projected path 1236 assists a clinician in determining whether the current orientation of the needle 1200, as depicted by the needle image 1234 on the display 1130, will result in arriving at the desired internal body portion target, such as the vessel 1226 shown here. Again, as the orientation and/or position of the needle image 1234 changes, the projected path 1236 is correspondingly modified by the system 1110. A target 1238, indicating the point where the projected path 1236 crosses the plane of the ultrasound image 1232, can also be depicted on the display 1130 by the system 1110. As shown in FIG. 23A, in the present example the target 1238 is located within the vessel 1226 depicted in the ultrasound image 1232. Note that the position of the target 1238 on the display 1130 can also be modified as the needle 1200 and/or the ultrasound image 1232 are adjusted. The screenshot 1230 also includes an area of probability 1239, here depicted as a box, which indicates any possible margin of error of the system due to needle length, needle rigidity and flex, field strength of the magnetic element, magnetic interference, possible discrepancy in alignment of the magnetic axis of the magnetic element with the longitudinal axis of the needle, orientation of the sensor array with respect to the ultrasound imaging plane, etc.

FIG. 23B shows that, in one embodiment, the screenshot 1230 can be configured such that the ultrasound image 1232 and the needle image 1234 are oriented so as to be displayed in a three dimensional aspect. This enables the angle and orientation of the needle 1200, as depicted by the needle image 1234, to be ascertained and compared with the intended target imaged by the ultrasound image 1232. It should be noted that the screenshots 1230 are merely examples of possible depictions produced by the system 1110 for display; indeed, other visual depictions can be used. Note further that the particular area of the body being imaged is merely an example; the system can be used to ultrasonically image a variety of body portions, and should not be limited to what is explicitly depicted in the accompanying figures. Further, the system as depicted and described herein can be included as a component of a larger system, if desired, or can be configured as a stand-alone device. Also, it is appreciated that, in addition to the visual display 1130, aural information, such as beeps, tones, etc., can also be employed by the system 1110 to assist the clinician during positioning and insertion of the needle into the patient.

As mentioned above, in one embodiment it is necessary for the system 1110 to know the total length of the needle 1200 and the location of the magnetic element 1210 thereon in order to enable an accurate depiction of the needle image 1234 and other features of the screenshots 1230 of FIGS. 23A and 23B to be made. The system 1110 can be informed these and/or other pertinent parameters in various ways, including scanning by the system of a barcode included on or with the needle, the inclusion of a radiofrequency identification ("RFID") chip with the needle for scanning by the system, color coding of the needle, manual entry of the parameters by the clinician into the system, etc. For instance, an RFID chip 1354 is included on the needle 1200 shown in FIG. 33A. The probe 1140 or other component of the system 1110 can include an RFID reader to read the information included on the RFID chip 1354, such as the type or length of the needle 1200, etc. These and other means for inputting the needle parameters into the system 1110 or detecting the parameters are therefore contemplated.

In one embodiment, a length of the needle (or other aspect of a medical component) can be determined by measurement by the probe/system of a characteristic of the magnetic element, such as its field strength. For instance, in one embodiment the magnetic element of the needle can be positioned at a predetermined distance from the probe or at a predetermined location with respect to the probe. With the magnetic element so positioned, the sensor array of the probe detects and measures the field strength of the magnetic element. The system can compare the measured field strength with a stored list of possible field strengths corresponding to different lengths of needles. The system can match the two strengths and determine the needle length. The needle location and subsequent needle insertion can then proceed as described herein. In another embodiment, instead of holding the magnetic element stationary at a predetermined location, the magnetic element can be moved about the probe such that multiple field strength readings are taken by the probe. Aspects that can be modified so as to impart different field strengths to a set of magnetic element include size, shape, and composition of the magnetic element, etc.

Further details are given here regarding use of the system 1110 in guiding a needle or other medical device in connection with ultrasonic imaging of a targeted internal body portion ("target") of a patient, according to one embodiment. With the magnetic element-equipped needle 1200 positioned a suitable distance (e.g., two or more feet) away from the ultrasound probe 1140 including the sensor array 1190, the probe is employed to ultrasonically image, for depiction on the display 1130 of the system 1110, the target within the patient that the needle is intended to intersect via percutaneous insertion. A calibration of the system 1110 is then initiated, in which algorithms are executed by the processor 1122 of the console 1120 to determine a baseline for any ambient magnetic fields in the vicinity of where the procedure will be performed. The system 1110 is also informed of the total length of the needle 1200, and/or position of the magnetic element with respect to the distal needle tip such as by user input, automatic detection, or in another suitable manner, as has been discussed above.

The needle 1200 is then brought into the range of the sensors 1192 of the sensor array 1190 of the probe 1140. Each of the sensors 1192 detects the magnetic field strength associated with the magnetic element 1210 of the needle 1200, which data is forwarded to the processor 1122. In one embodiment, such data can be stored in memory until needed by the processor. As the sensors 1192 detect the magnetic field, suitable algorithms are performed by the processor 1122 to calculate a magnetic field strength of the magnetic element 1210 of the needle 1200 at predicted points in space in relationship to the probe. The processor 1122 then compares the actual magnetic field strength data detected by the sensors 1192 to the calculated field strength values. Note that this process is further described by the U.S. patents identified above. This process can be iteratively performed until the calculated value for a predicted point matches the measured data. Once this match occurs, the magnetic element 1210 has been positionally located in three dimensional space. Using the magnetic field strength data as detected by the sensors 1192, the pitch and yaw (i.e., orientation) of the magnetic element 1210 can also be determined. Together with the known length of the needle 1200 and the position of the distal tip of the needle with respect to the magnetic element, this enables an accurate representation of the position and orientation of the needle can be made by the system 1110 and depicted as a virtual model, i.e., the needle image 1234, on the display 1130. Note that the predicted and actual detected values must match within a predetermined tolerance or confidence level in one embodiment for the system 1110 to enable needle depiction to occur.

Depiction of the virtual needle image 1234 of the needle 1200 as described above is performed in the present embodiment by overlaying the needle image on the ultrasound image 1232 of the display 1130 (FIGS. 23A, 23B). Suitable algorithms of the system 1110 as executed by the processor 1122 or other suitable component further enable the projected path 1236, the target 1238, and area of probability 1239 (FIGS. 23A, 23B) to be determined and depicted on the display 1130 atop the ultrasound image 1232 of the target. The above prediction, detection, comparison, and depiction process is iteratively performed to continue tracking the movement of the needle 1200 in real-time.

Figure 24:
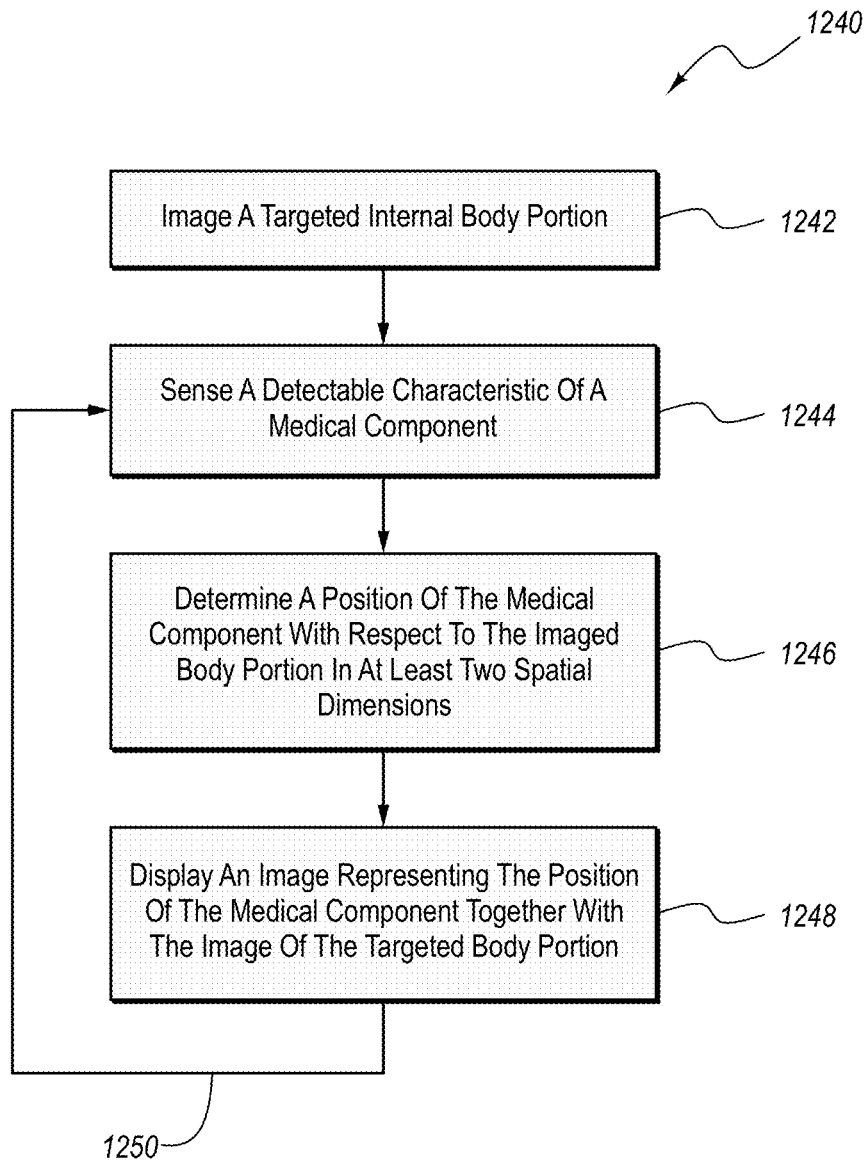
FIG. 24 shows various stages of a method for guiding a needle to a desired target within the body of a patient according to one embodiment.

In light of the foregoing and with reference to FIG. 24, it is appreciated that in one embodiment a method 1240 for guiding a needle or other medical component includes various stages. At stage 1242, a targeted internal body portion of a patient is imaged by an imaging system, such as an ultrasound imaging device for instance.

At stage 1244, a detectable characteristic of a medical component such as a needle is sensed by one or more sensors included with the imaging system. In the present embodiment, the detectable characteristic of the needle is a magnetic field of the magnetic element 1210 included with the needle 1200 and the sensors are magnetic sensors included in the sensor array 1190 included with the ultrasound probe 1140.

At stage 1246, a position of the medical component with respect to the targeted internal body portion is determined in at least two spatial dimensions via sensing of the detectable characteristic. As described above, such determination is made in the present embodiment by the processor 1122 of the console 1120.

At stage 1248, an image representing the position of the medical component is combined with the image of the targeted internal body portion for depiction on a display. Stage 1250 shows that stages 1244-1248 can be iteratively repeated to depict advancement or other movement of the medical component with respect to the imaged target, such as percutaneous insertion of the needle 1200 toward the vessel 1226 (FIGS. 23A, 23B), for instance.

It is appreciated that the processor 1122 or other suitable component can calculate additional aspects, including the area of probability 1239 and the target 1238 (FIGS. 23A, 23B) for depiction on the display 1130.

Figure 25:
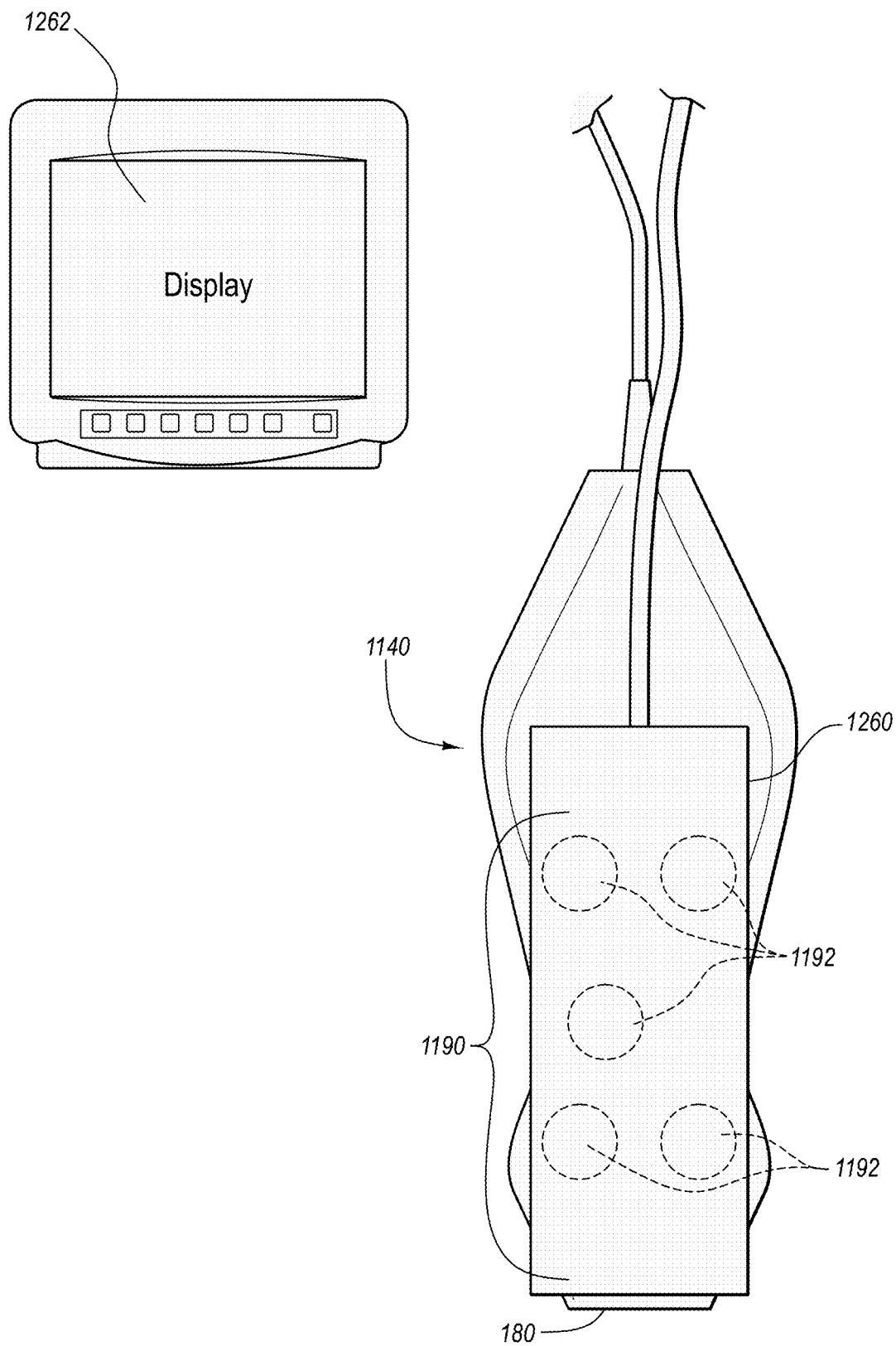
FIG. 25 shows a sensor array for attachment to an ultrasound probe and associated display, according to one embodiment.

It is appreciated that in one embodiment the sensor array need not be incorporated natively into the ultrasound imaging device, but can be included therewith in other ways. FIG. 25 shows one example of this, wherein an attachable sensor module 1260 including the sensors 1192 of the sensor array 1190 is shown attached to the ultrasound probe 1140. Such a configuration enables needle guidance as described herein to be achieved in connection with a standard ultrasound imaging device, i.e., a device not including a sensor array integrated into the ultrasound probe or a processor and algorithms configured to locate and track a needle as described above. As such, the sensor module 1260 in one embodiment includes a processor and algorithms suitable for locating and tracking the needle or other medical component and for depicting on a display the virtual image of the needle for overlay on to the ultrasound image. In one embodiment, the sensor module 1260 can be included with a module display 1262 for depiction of the needle tracking. These and other configurations of the guidance system are therefore contemplated.

Figure 26:
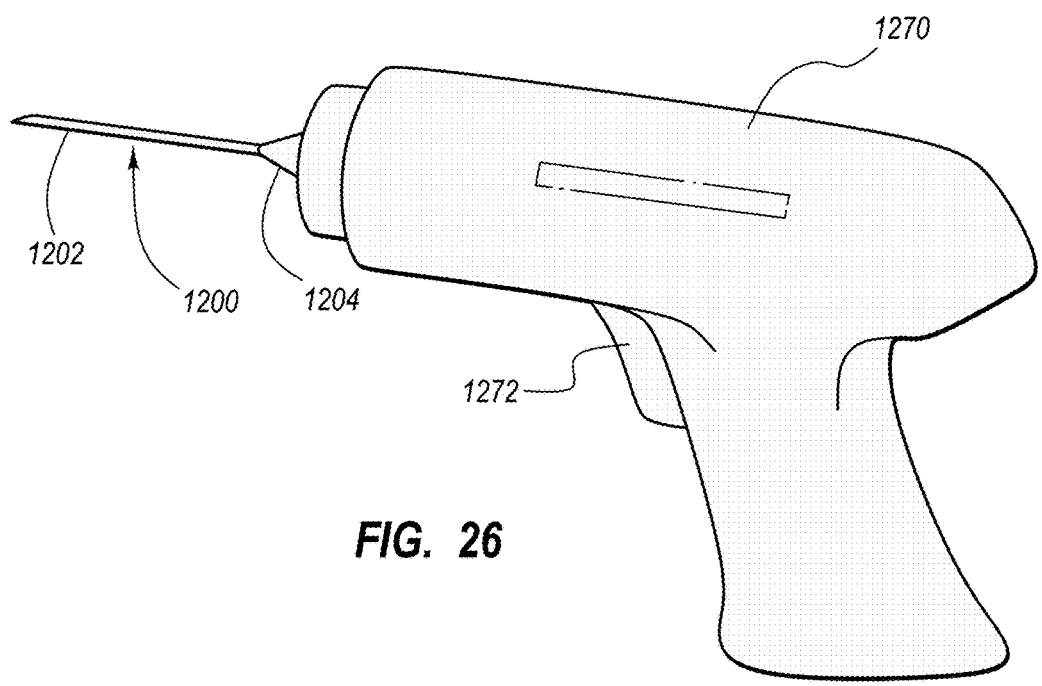
FIG. 26 is a simplified view of a needle holder gun for use with the guidance system of FIG. 18, according to one embodiment.

FIG. 26 shows that in one embodiment, a needle holder can be employed to hold and advance the needle 1200 during the ultrasound imaging and needle guidance procedure performed by the system 1110 as has been described. As shown, the needle holder 1270 is pistol-shaped and includes a trigger 1272 for selectively advancing the needle 1200 or other suitable medical component by moving the needle longitudinally away from the barrel of the holder upon pressing of the trigger. So configured, the needle holder 1270 facilitates ease of needle handling with one hand of the clinician while the other hand is grasping and manipulating the ultrasound probe 1140. In addition, the needle holder 1270 can provide needle movement/rotation assistance such as via a motor, ratcheting, hydraulic/pneumatic drivers, etc. Moreover, a clocking feature can be included on the needle holder 1270 to assist with determining the orientation of the distal tip of the needle 1200 and for facilitating rotation of the needle.

In one embodiment, the needle holder 1270 can be operably connected to the system 1110 such that advancement by the needle holder is automatically stopped when the distal end 1202B of the needle cannula 1202 reaches the targeted internal body portion or the needle intercepts the ultrasound plane. In yet another embodiment the magnetic element can be included with the needle holder instead of the needle itself. The needle, when temporarily attached to the needle holder, can thus be located and guided by the guidance system without the need for a magnetic element to be attached directly to the needle.

Note that other sensor configurations can also be employed. In one embodiment, an annular sensor can be configured to receive through a hole defined thereby the cannula of the needle. So disposed, a magnetic element of the needle is positioned proximate the annular sensor, which enables ready detection of the magnetic element and location of the needle by the system. The annular sensor can be attached to a surface of the probe, in one embodiment.

Figure 27:
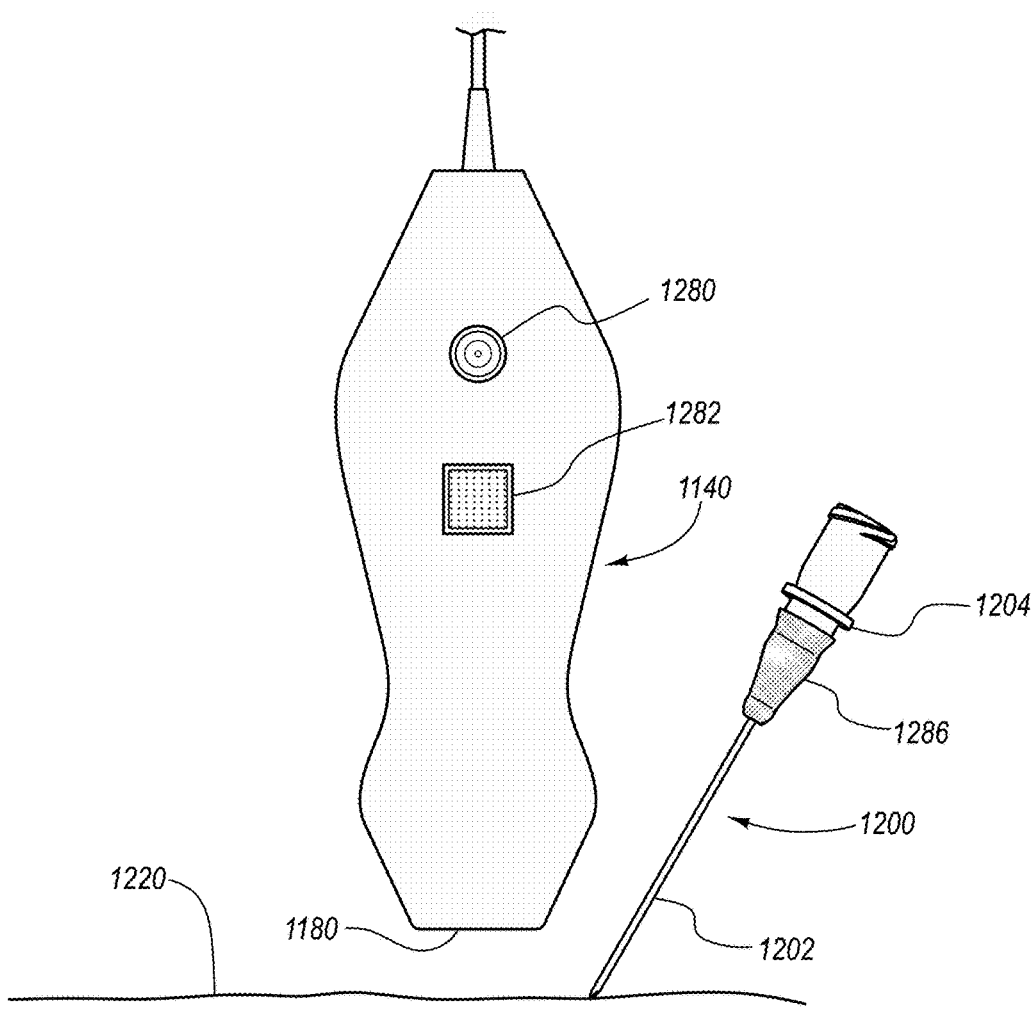
FIG. 27 is a simplified view of an ultrasound probe and needle including elements of an optical guidance system, according to one embodiment.
Figure 28:
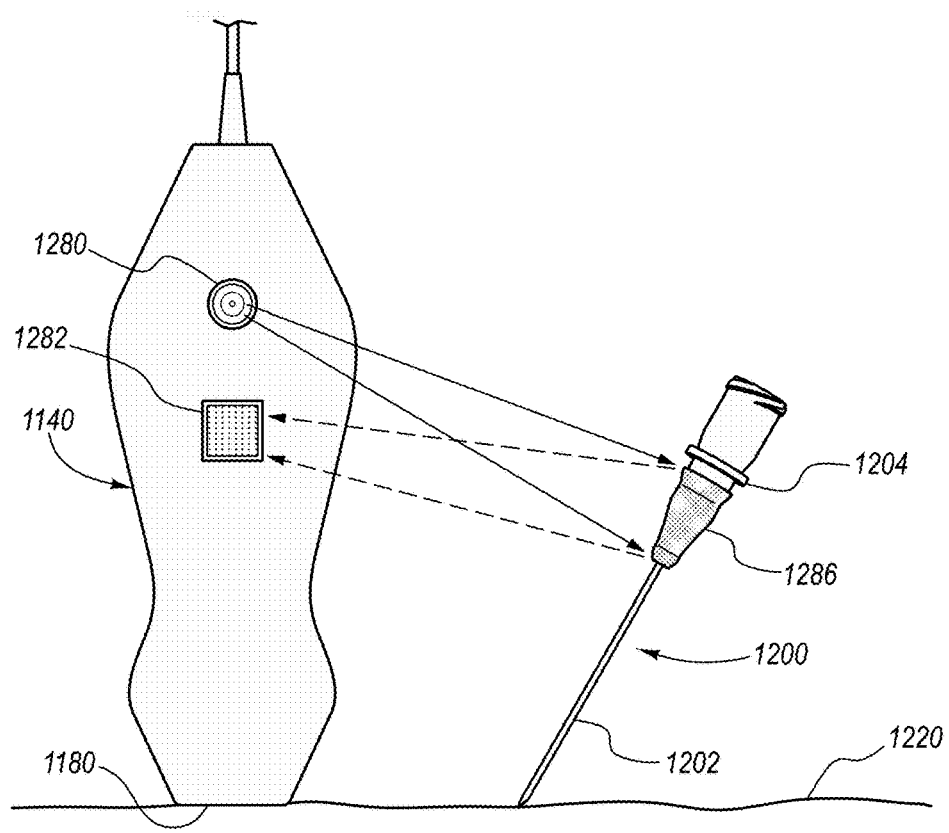
FIG. 28 shows operation of the ultrasound probe and needle of FIG. 27, according to one embodiment.

FIGS. 27 and 28 depict components of the guidance system 1110 according to another embodiment, wherein an optical-based interaction between the probe 1140 and the needle 1200 is employed to enable tracking and guidance of the needle. In particular, the probe 1140 includes a optical/light source, such as an LED 1280, and a photodetector 1282 positioned on the probe surface. It is appreciated that the light source and detector can be configured to produce and detect light signals of a variety of ranges including visible, infrared, etc.

The needle hub 1204 includes a reflective surface 1286 capable of reflecting light produced by the LED 1280 and incident thereon. As shown in FIG. 28, light emitted by the LED 1280 is reflected by the reflective surface 1286 of the needle 1200, a portion of which is received and sensed by the photodetector 1282. As in previous embodiments, the processor 1122 of the system console 1120 can be employed to receive the sensed data of the photodetector 1282 and compute the position and or orientation of the needle 1200. As before, the length of the needle 1200 and/or the position of the reflective surface with respect to the distal end of the needle 1200 are input into or otherwise detectable or known by the system 1110. Note that the reflective surface can be included at other locations on the needle.

In light of the above, it is appreciated that in the present embodiment the detectable characteristic of the needle 1200 includes the reflectivity of the reflective surface 1286, in contrast to the magnetic field characteristic of the magnetic element 1210 of previous embodiments, and the sensor includes the photodetector 1282, in contrast to the magnetic sensors 1192 of previous embodiments. It should be appreciated that in one embodiment, the above-described configuration can be reversed, wherein an optical source is included with the needle or medical component. In this case, light is emitted from the needle and detected by the photodetector 1282 included with the probe 1140 so as to enable location and tracking of the needle. A power source can be included with the needle, such as a watch battery or the like, in order to power the light source of the needle.

More generally, it is appreciated that the needle or medical component can include one or more of these or other detectable characteristics to enable the needle to be tracked and guided toward a target within the body of the patient. Non-limiting examples of other detectable characteristic modalities include electromagnetic or radiofrequency ("RF") (see, e.g., FIGS. 29-30 below), and radioactivity. With respect to RF modalities, it is appreciated that one or more synchronously or asynchronously pulsed frequency sources can be included with the needle as to enable detection thereof by a suitable sensor(s). Or, an RF first source can be coupled with a passive magnet as a second source.

Figure 29:
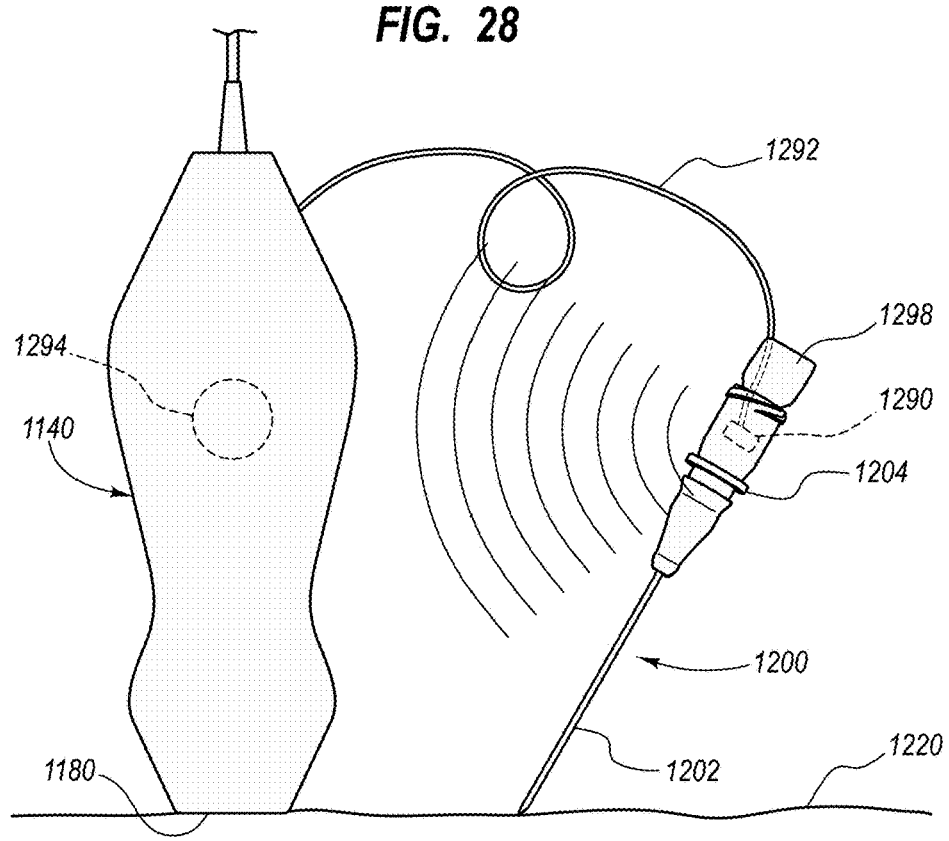
FIG. 29 is a simplified view of an ultrasound probe and needle including elements of an electromagnetic signal-based guidance system, according to one embodiment.
Figure 30:
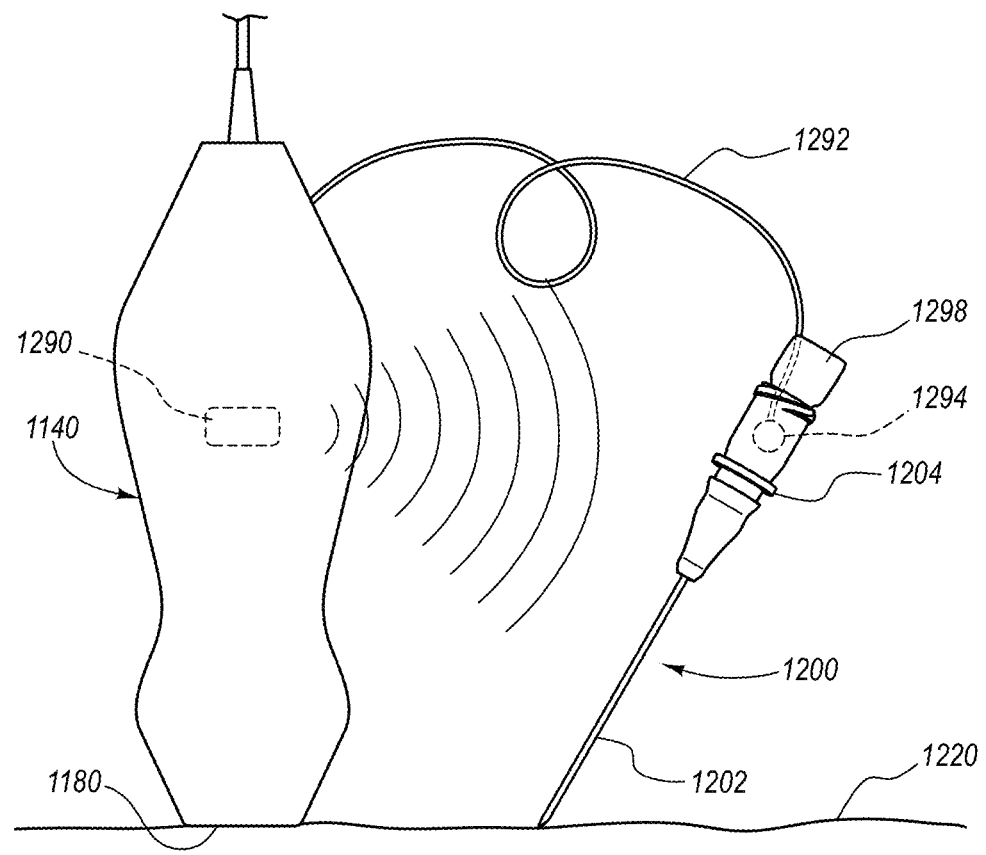
FIG. 30 is a simplified view of an ultrasound probe and needle including elements of an electromagnetic signal-based guidance system, according to another embodiment.
Figure 31C:
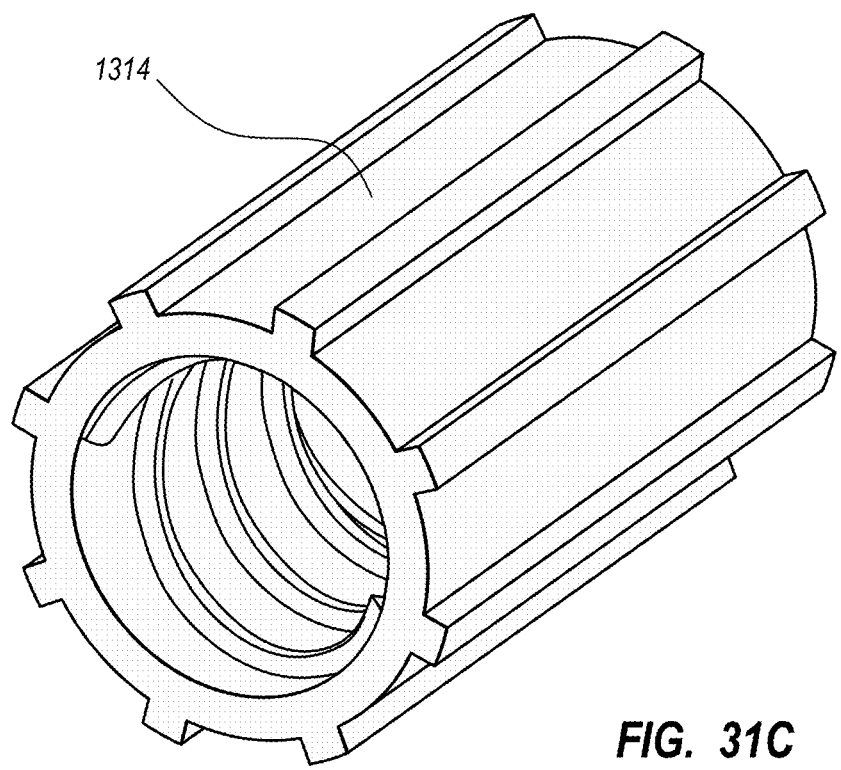
Figure 31D:
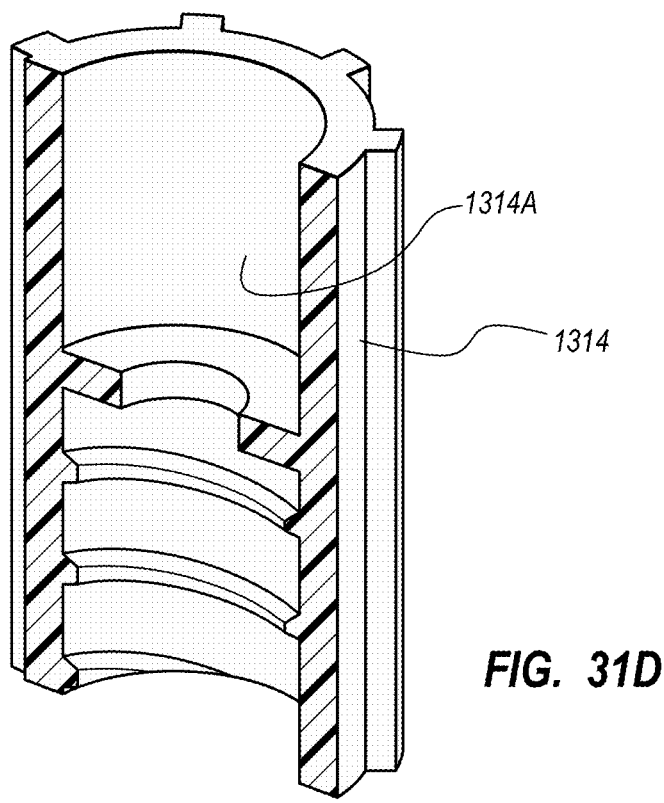

FIGS. 29 and 30 depict components of a guidance system according to one embodiment, wherein EM signal interaction between the probe 1140 and the needle 1200 is employed to enable tracking and guidance of the needle. In particular, in FIG. 29 the needle 1200 includes a stylet 1298 disposed therein. The stylet 1298 includes an EM coil 1290 that is operably connected to the probe 1140 via a tether 1292. In this way, the EM coil 1290 can be driven by suitable components included in the probe 1140 or system console 1120 such that the EM coil emits an EM signal during operation.

A sensor 1294 suitable for detecting EM signals emitted by the EM coil 1290 of the stylet 1298 is included in the probe 1140. In the present embodiment, the sensor 1294 is a three-axis sensor for detecting corresponding orthogonal components of the EM signal, though other coil and sensor configurations can also be employed. So configured, the position and orientation of the needle 1200 can be determined, by EM signal triangulation or other suitable process, and displayed by the system in a manner similar to that already described above. As in previous embodiments, the processor 1122 of the system console 1120 (FIG. 18) can be employed to receive the sensed data of the EM sensor 1294 and compute the position and/or orientation of the needle 1200. As before, the length of the needle 1200 and/or the position of the EM coil 1290 with respect to the distal end of the needle 1200 are input into or otherwise detectable or known by the system.

FIG. 30 shows a variation of the EM configuration of FIG. 29, wherein the respective positions of the EM components is reversed: the EM coil 1290 is included in the probe 1140 and the EM sensor 1294 is included with the stylet 1298 disposed in the needle 1200. Note that in the embodiments of FIGS. 29 and 30, the operable connection between the EM coil 1290 and the EM sensor 1294 via the tether 1292 enables the component disposed in the stylet 1298 to be driven by the system 1110. This also enables correspondence of the particular EM frequency/frequencies emitted by the EM coil 1290 and detected by the EM sensor 1294 to be made. In one embodiment, the configuration shown in FIG. 29 can be varied, wherein no tether operably connects the EM coil and the EM sensor; rather, the EM coil of the stylet operates as a separate component from the probe and its EM sensor and is powered by an independent power source, such as a battery. In this case, the probe/system includes suitable signal processing components configured to detect the EM signal emitted by the EM coil and to process it as necessary in order to locate the needle.

Note that the EM coil and EM sensors can be included at other locations than what is depicted herein. For instance, the EM coil can be included on the needle itself, or on a connector that is attachable to the proximal end of the needle.

FIGS. 31A-31D give further details of the needle 1200 configured according to one embodiment, wherein the needle includes a hub 1304 from which extends the cannula 1202. A magnetic element 1310 defining a hole 1312 is included in a cavity 1314A of a housing 1314. The housing 1314 includes threads so as to threadably engage the needle hub 1304 or other suitable component of the needle or medical component. In this way, the magnetic element 1310 is removably attachable to the needle 1200 via the housing 1314. Thus, the magnetic element 1310 need not be permanently affixed or included with the needle 1200, but rather can be removed therefrom when magnetic-based needle guidance is no longer needed. In addition, this enables the magnetic element to be attached to many different types and sizes of needles. Note that in the present embodiment the needle 1200 further includes a distally slidable needle safety component 1320 for safely isolating the distal tip of the needle upon removal of the needle from the patient. Note further that other removable magnetic elements can be employed in addition to what is explicitly shown and described herein.

FIGS. 32-33B give further examples of the needle 1200 including a magnetic element. In FIG. 32, two bar-like magnetic elements 1340 are disposed so as to orthogonally extend from a hub 1334 of the needle 1200, illustrating that the magnetic element need not be oriented parallel to the longitudinal axis of the needle. In FIGS. 33A-33B, four magnetic elements 1350 are included in the needle hub 1344, showing that more than one magnetic element can be included with the needle. Such a configuration may be employed, for example, where limited space prevents one magnetic element from being used. Note the number, shape, and placement of the magnetic elements here is only one example of many possible configurations.

Figure 34A:
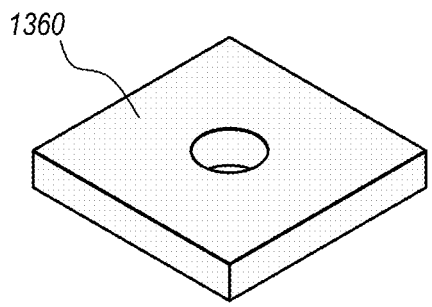
FIGS. 34A-34G are views of variously shaped magnetic elements for use with a needle guidance system according to one embodiment.
Figure 34B:
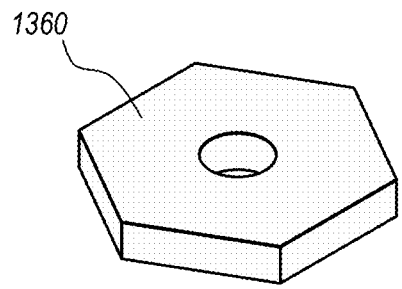
Figure 34C:
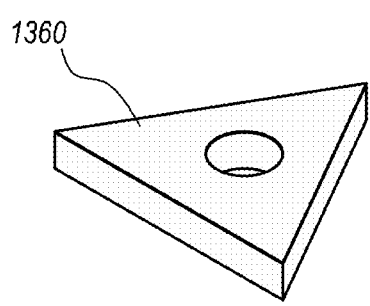
Figure 34D:
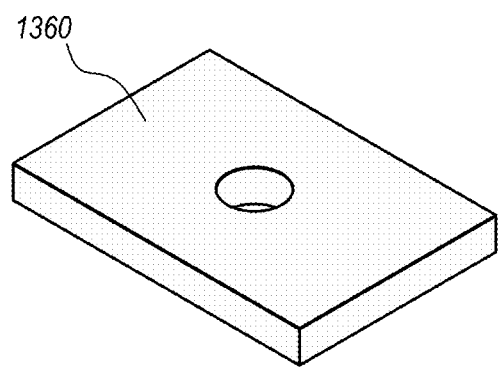
Figure 34E:
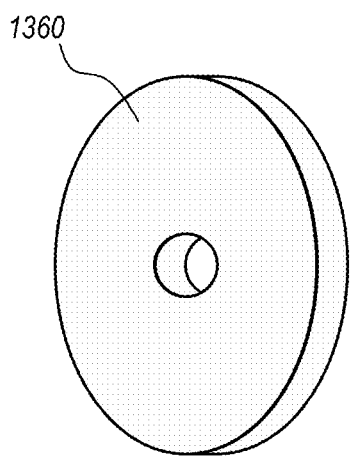
Figure 34F:
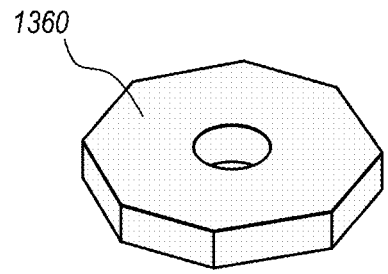
Figure 34G:
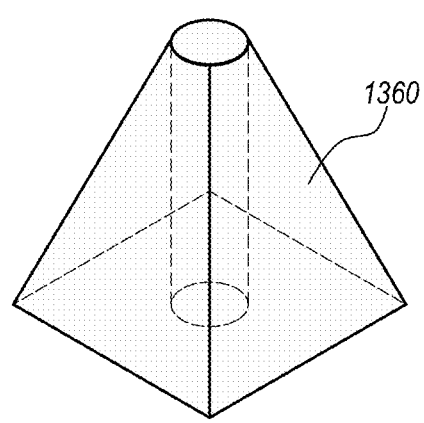

FIGS. 34A-34G give various example configurations of a magnetic element 1360 that defines a hole for receiving the cannula of the needle therethrough. Various shape configurations for the magnetic element 1360 are shown, including a square (FIG. 34A), a hexagon (FIG. 34B), a triangle (FIG. 34C), a rectangle (FIG. 34D), an oval (FIG. 34E), an octagon (FIG. 34F), and a four-sided pyramid (FIG. 34G). The magnetic elements shown in the accompanying figures are merely examples of the broad number of geometric and other shapes that can be used to define the magnetic element; indeed other shapes not shown explicitly herein are also contemplated.

Figure 35:
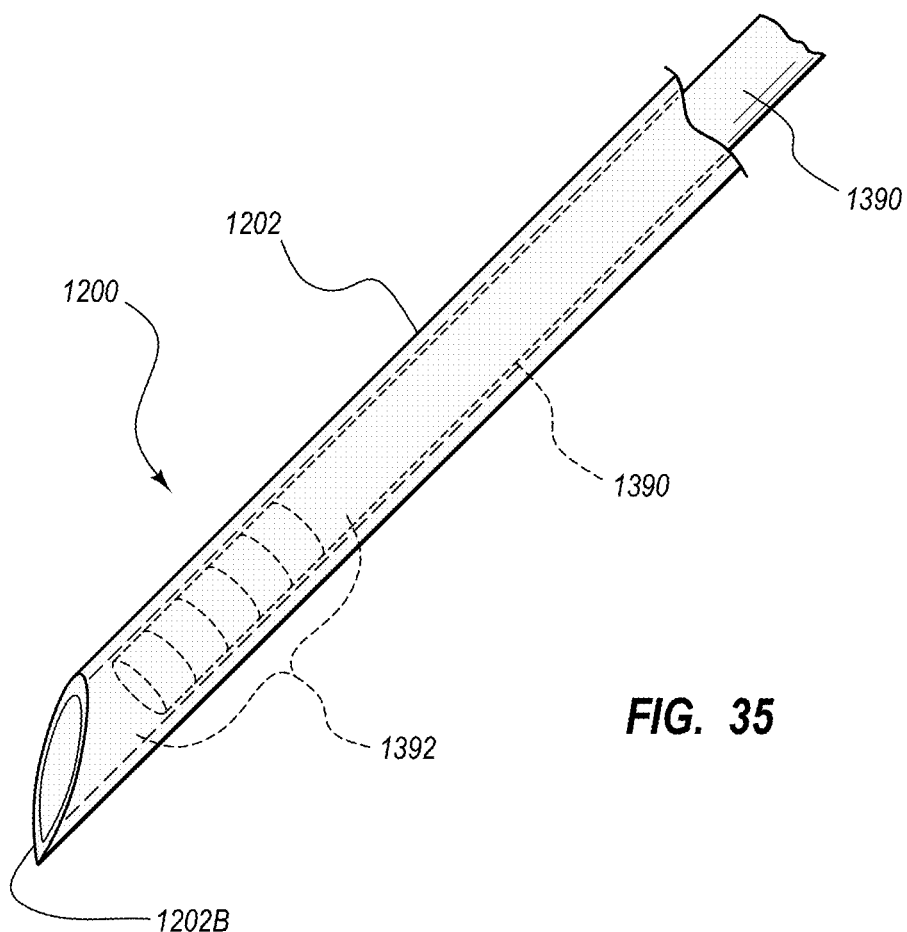
FIG. 35 is a perspective view of a distal portion of a needle cannula including a magnet-bearing stylet disposed therein, according to one embodiment.
Figure 36:
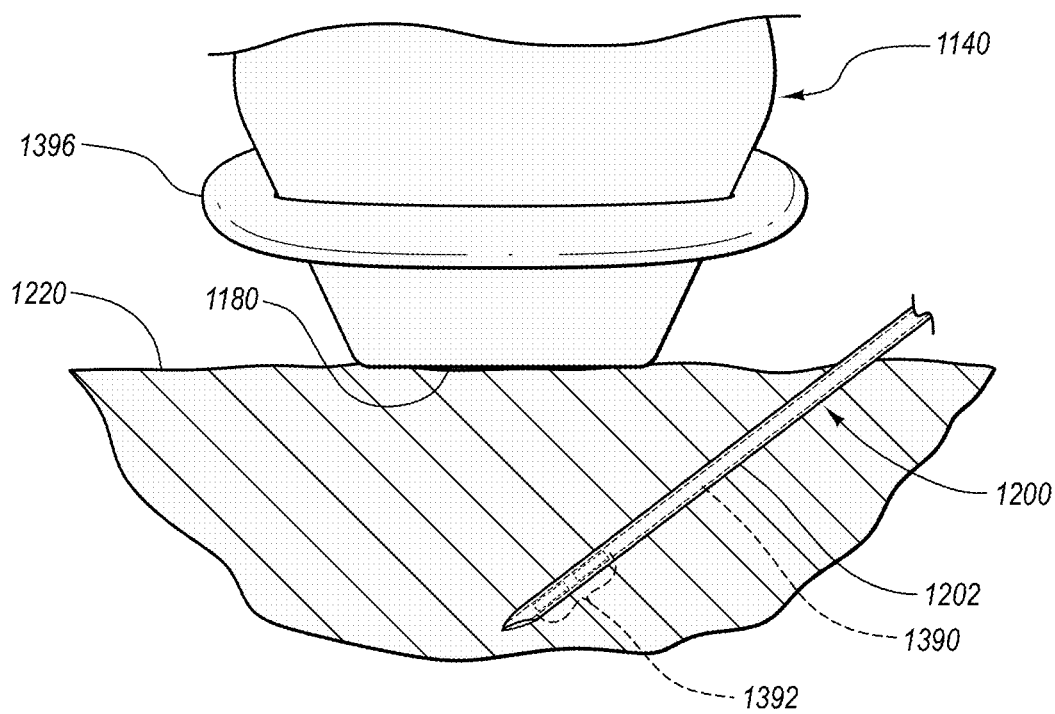
FIG. 36 shows the needle of FIG. 35 in use with an ultrasound probe including a ring sensor, according to one embodiment.

FIGS. 35 and 36 depict yet another embodiment, wherein a stylet 1390 is included for removable insertion into the hollow cannula 1202 of the needle 1200. A plurality of permanent magnets 1392, such as solid, cylindrically shaped ferromagnets stacked end-to-end with each other, is included at a distal end of the stylet 1390. As shown in FIG. 36, the stylet 1390 is received within the needle cannula 1202 during insertion of the needle 1200 into the patient. A sensor ring 1396 or other suitable magnetic sensor can be included with or in proximity to the probe 1140 to enable detection of the magnetic field of the magnets 1392, thus enabling the guidance system to detect the position and orientation of the needle 1200 and superimpose an image thereof atop the ultrasound image produced by the probe 1140 in a manner similar to that described in connection with FIGS. 5A-7.

FIGS. 35 and 36 thus illustrate that the magnetic element(s) can be configured in any one of a variety of ways. In one embodiment, for example, the magnetic elements can be disposed more proximally along the stylet length. In another embodiment, the stylet itself can be magnetized or composed of magnetic materials. It is appreciated that the stylet can be configured in one of many different ways, analogous examples of which can be found in U.S. Pat. No. 5,099,845, titled "Medical Instrument Location Means," and U.S. Pat. No. 8,784,336, filed Aug. 23, 2006, titled "Stylet Apparatuses and Methods of Manufacture," both of which are incorporated herein by reference in their entireties. These and other variations are therefore contemplated.

It should be appreciated herein that "stylet" as used herein can include any one of a variety of devices, including guidewires, configured for removable placement within a lumen of the needle to assist in the placement thereof within the patient. In one embodiment, the stylet can include a sharp end that distally extends past a blunt distal end of the needle cannula so as to enable a blunt needle to be inserted into a patient. Note that the stylet in one embodiment stiffens the needle so as to minimize unintended bending thereof during insertion.

Figure 37:
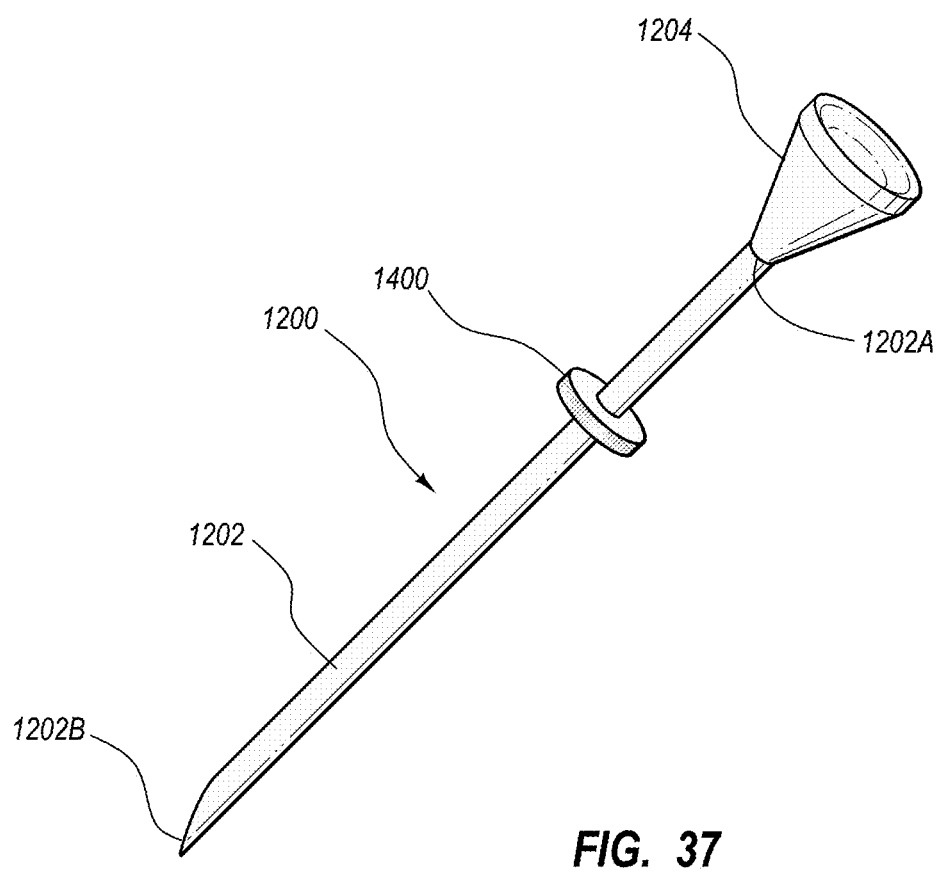
FIG. 37 is a perspective view of a needle including a donut magnet disposed on the cannula, according to one embodiment.

FIG. 37 depicts yet another possible embodiment, wherein the needle 1200 includes an annular or donut-shaped magnet 1400 disposed distal to a proximal end 1202A of the needle cannula 1202. Note that the magnet 1400 can be positioned in one of several positions along the length of the cannula 1202, in other embodiments. Positioning of the magnet 1400 relatively closer to the distal needle tip reduces the effects that unintended bending of the needle has on determining and displaying the position of the needle. In yet another embodiment, the needle itself can be magnetized. Note further that the relative places of the sensor and source (e.g., magnet) of the system can be reversed. These and other configurations are also contemplated. Further, note that the discussion herein can be applied to other imaging modalities in addition to ultrasound, including MRI, x-ray and CT scanning, etc.

Figure 38:
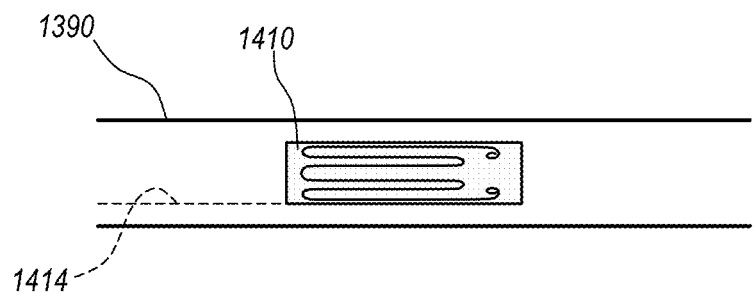
FIG. 38 is a side view of a stylet including a strain gauge according to one embodiment.

FIG. 38 depicts a strain gauge 1410 included on a stylet, such as the stylet 1390 shown in FIGS. 35 and 36 for instance. The strain gauge 1410 can be operably connected to the probe 1140, console 1120 (FIG. 18), or other component of the system 1110 via a conductive path 1414. One example of the conductive path 1414 includes one or more conductive wires disposed in or along the stylet 1390, for instance. So connected, the strain gauge 1410 acts as a transducer and can provide data relating to bending of the needle in which the stylet 1390 is disposed during needle insertion procedures, given that bending of the needle 1200 will cause similar bending to occur in the stylet 1390.

Figure 39A:
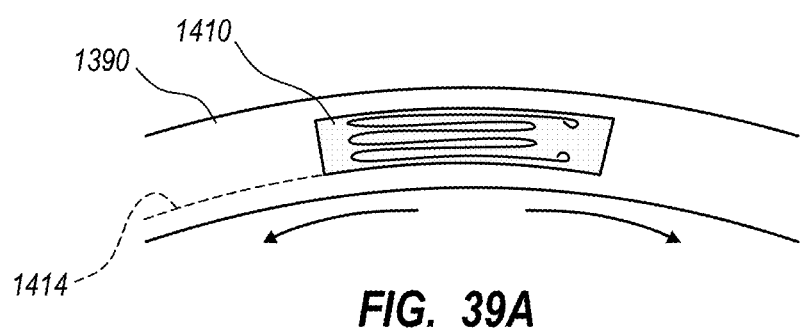
FIGS. 39A-39B show the stylet and strain gauge of FIG. 38 under bending stress.
Figure 39B:
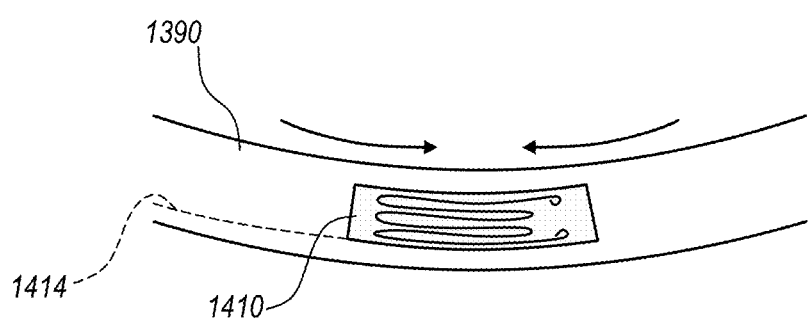
Figure 40:
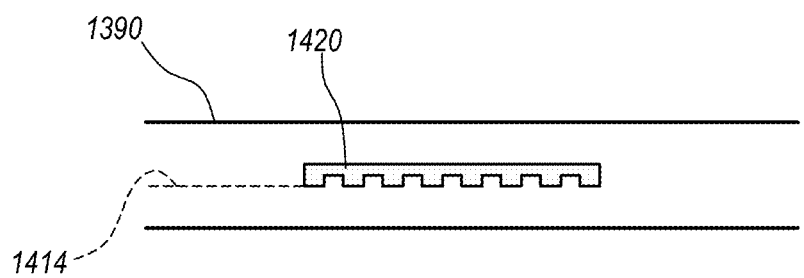
FIG. 40 is a side view of a stylet including a flex sensor according to one embodiment.

These data sensed via bending of the strain gauge 1410 can be forwarded to and interpreted by the processor 1122 (FIG. 18) or other suitable component of the system 1110 so as to include such bending together with detection of the magnetic element by the probe sensors 1192 (FIG. 20) in computing the position of the needle 1200, especially the distal tip thereof. This results in enhanced accuracy for locating and depicting the position of the needle distal tip. Indeed, FIG. 39A shows flexure of the strain gauge 1410 in one direction as caused by bending of the stylet 1390, wherein FIG. 39B shows flexure of the strain gauge in another direction. Such stylet bending is thus detected by the strain gauge 1410 (via changes in electrical resistance within the strain gauge in one embodiment) and forwarded to the system 1110 for use in computing needle position. Note that other suitable sensors and gauges can optionally be used for measuring needle/stylet bending, including a flex sensor 1420, as shown in FIG. 40 for instance, and capacitance and fiber optic-based strain gauges/sensors. Also, the sensor/gauge may be placed directly on the needle/medical component, in one embodiment.

FIGS. 41-59 depict various embodiments generally directed to the inclusion of a magnetic element, such as a permanent magnet with a needle, needle-related component, or other medical device. In particular, embodiments are disclosed for providing a needle assembly with a magnetic element whose magnetic axis is coaxially aligned with the longitudinal axis of the needle cannula. Such a magnetic element-equipped needle assembly can be spatially tracked by a suitable magnetic-based needle insertion guidance tracking system, in preparation for insertion of the needle into the body of a patient, for instance, as already described above.

Figure 41A:
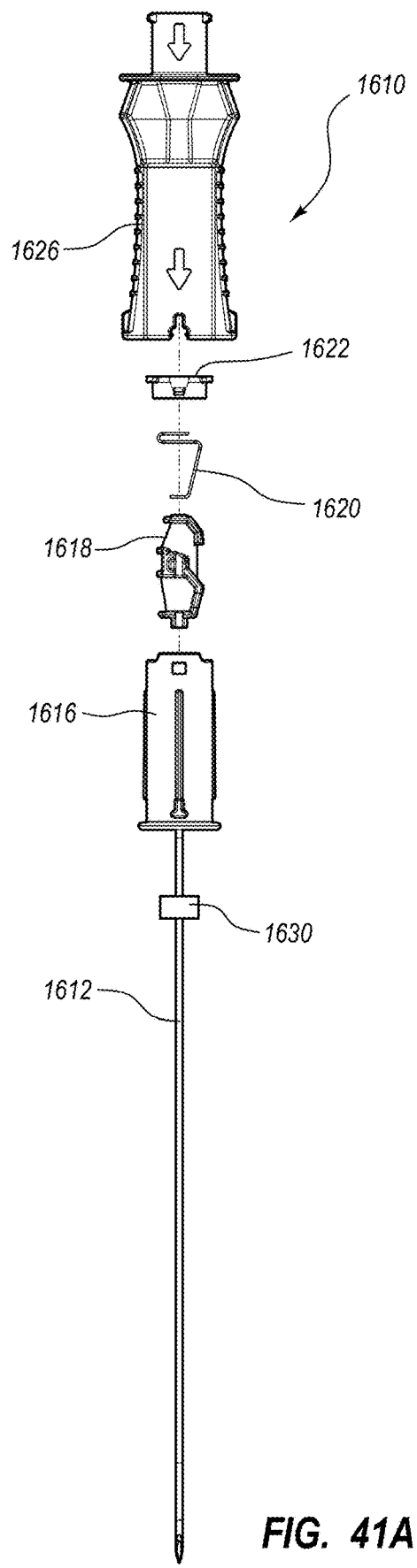
FIGS. 41A-41C are various views of a needle assembly according to one embodiment.
Figure 41B:
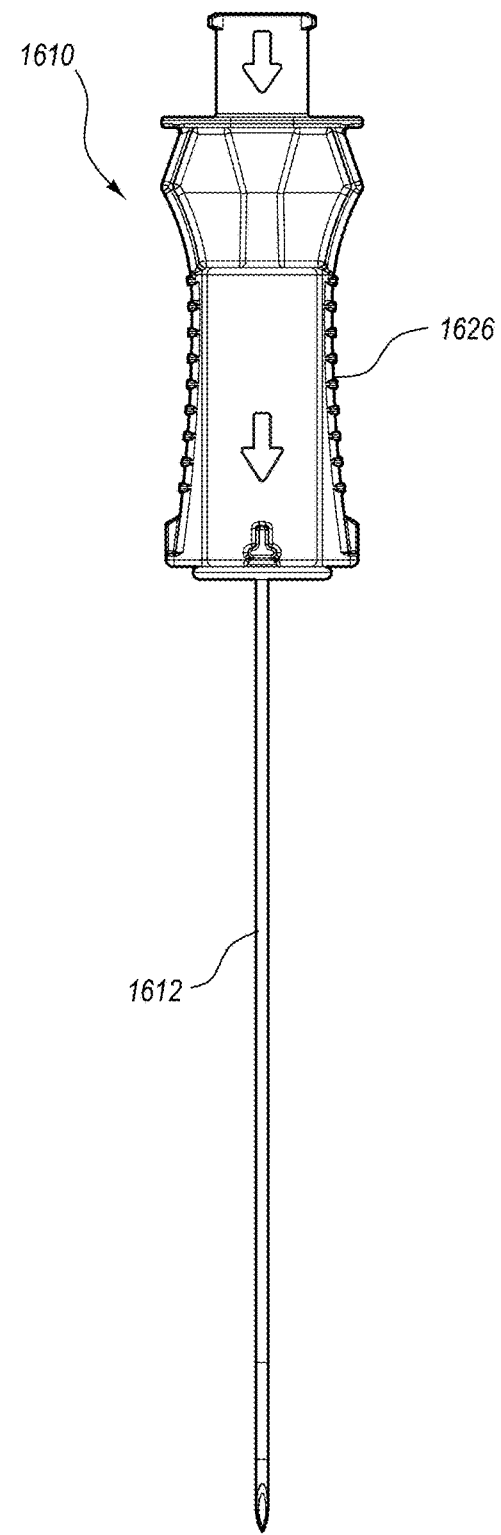
Figure 41C:
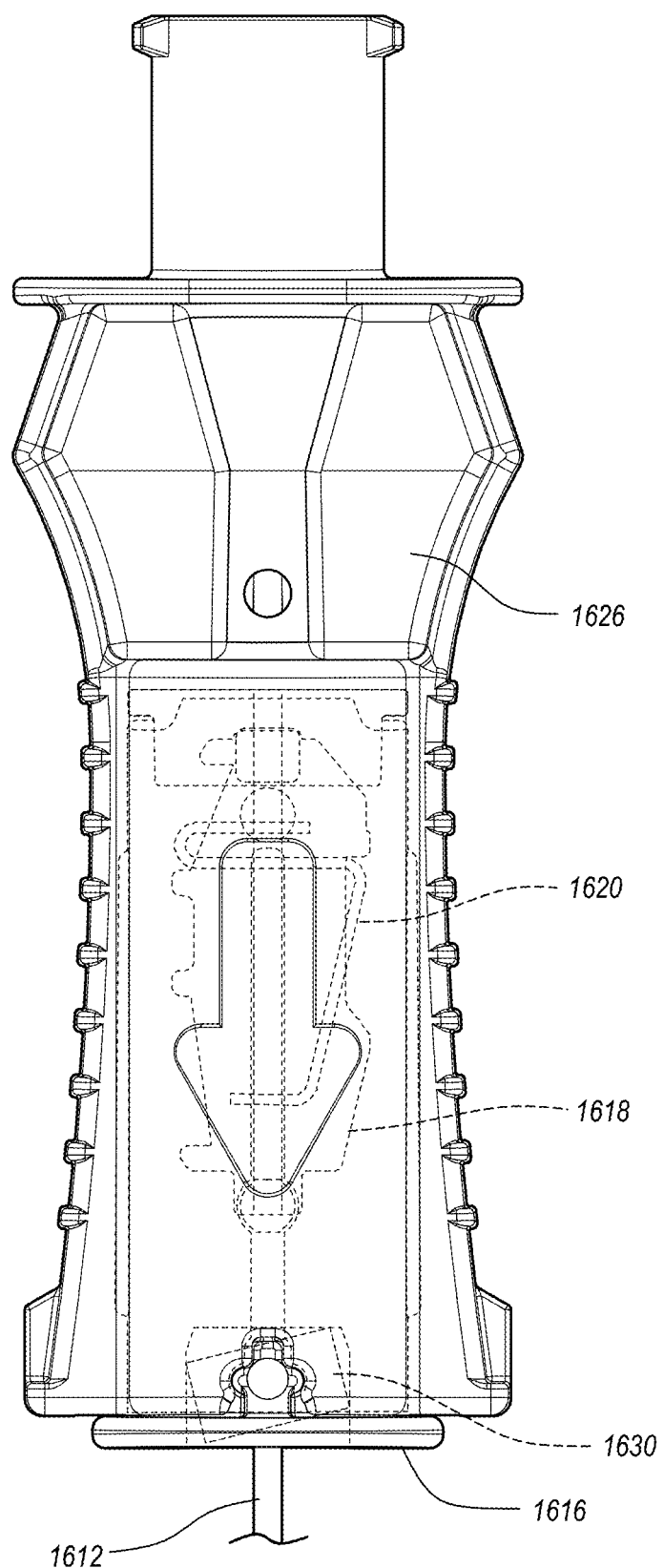

FIGS. 41A-41C show various details regarding a needle assembly 1610 that serves as one example of a medical device or component that can be guided by the above-described guidance system, in accordance with one embodiment. As shown, the needle assembly 1610 includes a hollow cannula 1612 and a safety can 1616 disposed at a proximal end of the cannula. A carriage 1618 and binding element 1620 of a needle safety component are shown for disposal within the safety can 1616. A cap 1622 covers a proximal end of the safety can 1616, and the safety can is sized for insertion into and affixation within a needle hub 1626.

A magnetic element 1630, such as a permanent magnet, is also included and is sized such that the cannula 1612 can pass through a hole 1632 defined therein and such that the magnetic element is securely disposed within a recess defined in the safety can 1616. So configured, the magnetic element 1630 in the present embodiment is cylindrically shaped with the hole 1632 defined along its central axis. Further, in accordance with present embodiments and as best seen in FIG. 41C, the magnetic element 1630 is oriented within the recess of the safety can 1616 such that its magnetic axis, which may not align with its central axis, is coaxially aligned with the longitudinal axis of the cannula 12. For example, the permanent magnet serving as the magnetic element 1630 shown in FIGS. 41A-41C is shown in FIG. 41C as tilted with respect to the needle assembly cannula 1612 such that its magnetic axis is substantially coaxially aligned with the longitudinal axis of the cannula. This alignment enables the needle insertion guidance system described further above to accurately track the distal needle tip.

Note that, though explicitly described in connection with the needle assembly shown in FIGS. 41A-41C and in the other accompanying figures, the present embodiments regarding magnetic element alignment can be applied to needle assemblies/medical devices of varying configurations, designs, etc. As such, the discussion to follow should not be considered limiting in any way. In particular, though described herein as disposed in a safety can of a needle assembly hub, the magnetic element can be disposed/positioned in other ways as well. Further, "safety can" as used herein can be understood to refer to a hub, housing, or any other object in which or with which a magnetic element can be disposed.

In one embodiment, the cannula 1612 includes a material of low magnetic permeability. Specifically, in one embodiment the cannula 1612 includes an austenitic alloy including nickel and chromium, such as the material marketed under the name INCONEL® 625, by Special Metals Corporation, New Hartford, New York, U.S.A. Such material shows a reduced tendency to become temporarily magnetized and attracted by the magnetic material, thus preserving the integrity of the magnetic field and leading to more accurate results when the needle is tracked using a magnetic-based guidance system. Other possible materials include low magnetic-permeability stainless steel, other variations of stainless steel, etc.

In one embodiment, the magnetic element 1630 is a permanent magnet including neodynium-iron-boron. In one embodiment, such a permanent magnet may further include dysprosium and other rare-earth elements. In one embodiment, the permanent magnet is formed from a powder, which is first oriented by an applied magnetic field, then compressed at high pressure before being sintered in a furnace. It is appreciated that a permanent magnet can be composed of other materials, including samarium-cobalt, and manufactured in ways other than pressed and sintered powders. As such, it is appreciated that the examples of magnetic elements given herein are not considered limiting. In another embodiment, an N52 MGOe rare-earth neodynium magnet is employed.

Note that, in one embodiment the needle 10 or other medical device to be tracked by a magnetic-based guidance system referred to herein includes an RFID chip that can be read by an RFID reader included with a probe or other component of the guidance system. The RFID chip of the needle can include information of the needle including the needle name, type, distance from the needle magnetic element to the needle distal tip, the strength and/or size of the magnetic element, and other useful information. Such information can be used by the guidance system to adjust its operating parameters to match the type of needle being used. In another embodiment, the information regarding the needle is manually input into the guidance system. In yet another embodiment, a barcode can be included on or with the needle to enable the guidance system to determine pertinent information regarding the needle. In one embodiment, the system includes a memory location for storing a database of characteristics of needles that may be used with the guidance system.

Figure 42:
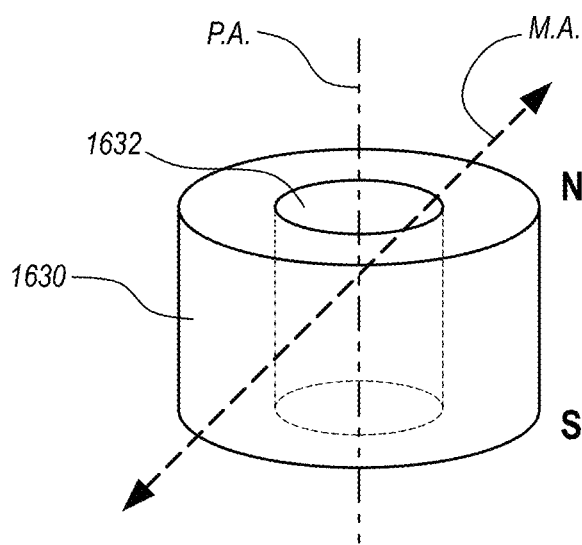
FIG. 42 is a perspective view showing various aspects of a magnetic element.

FIG. 42 shows a permanent magnet as the magnetic element 1630 including a hole 1632 and is similar to the magnetic element shown in FIGS. 41A-41C. As shown, the magnetic element 1630 includes a physical axis, indicated by P.A., which extends through the body of the magnetic element. As the magnetic element 1630 is defined as a cylinder, the physical axis P.A. corresponds with the central axis of the cylindrical magnetic element. Also shown is a magnetic axis, indicated by M.A., which extends through the cylindrical body of the magnetic element 1630 at an angle with respect to the physical axis P.A., and thus is not coaxial with the physical axis.

Figure 43:
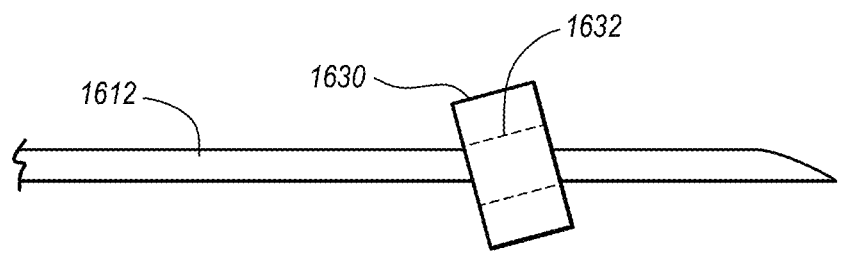
FIG. 43 is a side view of a needle cannula and magnetic element according to one embodiment.

As many permanent magnets include non-coaxial, angularly-deviated physical and magnetic axes as just described, it is desirable in such cases to position a magnet in a needle assembly for use with the above-described needle insertion guidance system such that its magnetic axis—and not necessarily its physical axis—is substantially coaxially aligned with the longitudinal axis of the needle assembly cannula so that the needle insertion guidance system can accurately indicate the position of the needle distal tip, given its detection of the properly oriented magnet. When this is done, the magnetic element may be physically oriented at an angle with respect to the needle cannula in cases where the magnetic element receives the cannula through a hole defined therein. This instance is shown in FIG. 43, where the magnetic element 1630 is shown with the needle assembly cannula 1612 disposed through the magnetic element hole 1632 and the magnetic element angularly skewed so that the magnetic axis of the magnetic element is substantially coaxially aligned with the longitudinal axis of the cannula. Note that the hole 1632 is of sufficient diameter to enable such orienting of the magnetic element 1630 on the cannula 1612. Suitable measurements can be made to determine the angular offset of the magnetic axis, if any, so as to determine the amount of skewing/tilting necessary for each magnetic element.

Figure 44:
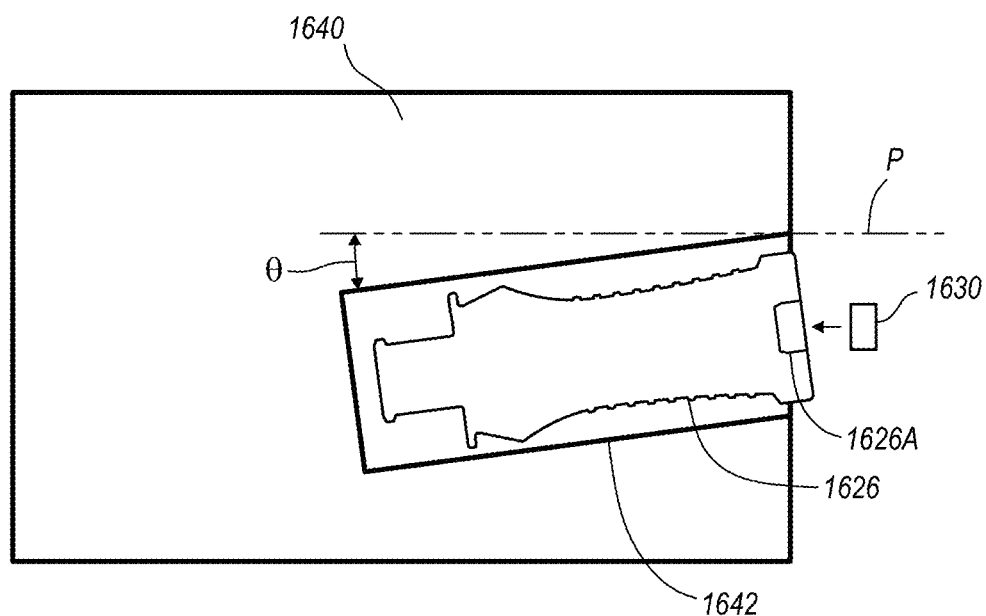
FIG. 44 is a top view of a jig, needle hub, and magnetic element according to one embodiment.
Figure 45:
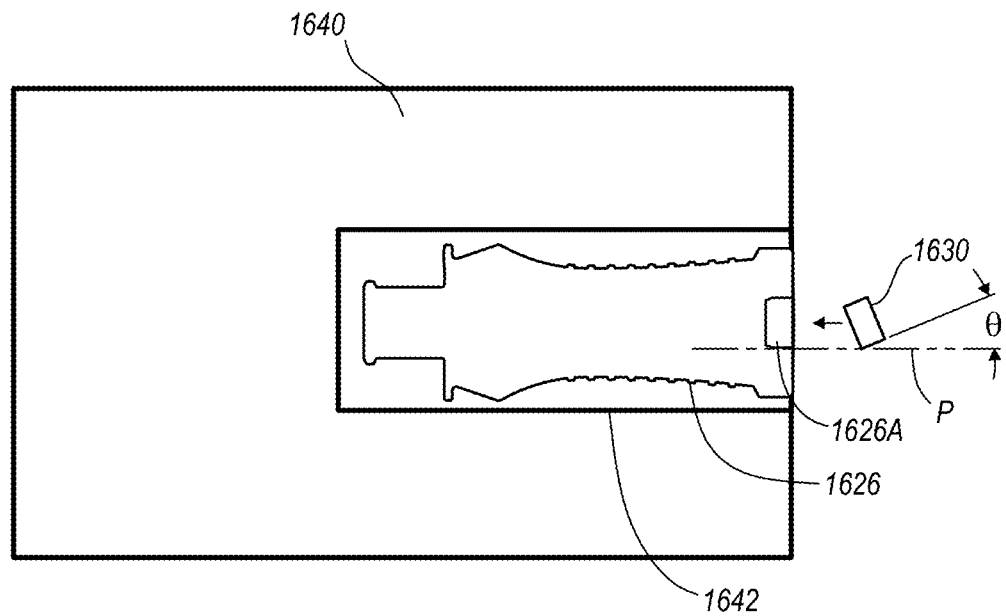
FIG. 45 is a top view of a jig, needle hub, and magnetic element according to one embodiment.

FIGS. 44 and 45 show orientation of the magnetic element 1630 with respect to a portion of a needle assembly according to one embodiment. In particular, FIG. 44 shows a jig 1640 that includes a cavity 1642 that is angularly offset at an angle θ from parallel P, as shown. The magnitude of the offset angle θ corresponds with the deviation of the magnetic axis of the magnetic element from its physical axis. The needle assembly hub 1626, including a recess 1626A, is disposed in the angled cavity 1642. The magnetic element 1630 is then inserted into the hub recess 1626A in a direction parallel to P such that it seats within the hub recess in an angled orientation. The magnetic element 1630 is affixed within the hub recess 1626A in this orientation. Later, when the proximal end of the cannula is received into the hub recess 1626A and the hole of the magnetic element 1630, its longitudinal axis will be substantially coaxially aligned with the magnetic axis of the magnetic element, as desired.

The configuration of the jig 1640 in FIG. 45 differs from that in FIG. 44 in that the cavity 1642 is parallel to P while the magnetic element 1630 is inserted into the hub recess 1626A at the offset angle θ that corresponds to its angle of magnetic axis deviation from its physical axis. The magnetic axis 1630 can be affixed within the hub recess 1626A in this orientation. Note that, though shown in FIGS. 44 and 45 as being inserted into a recess directly defined in the needle assembly hub, the magnetic element can be inserted in this manner into a safety can or other component of the needle assembly or suitable medical device.

Figure 46:
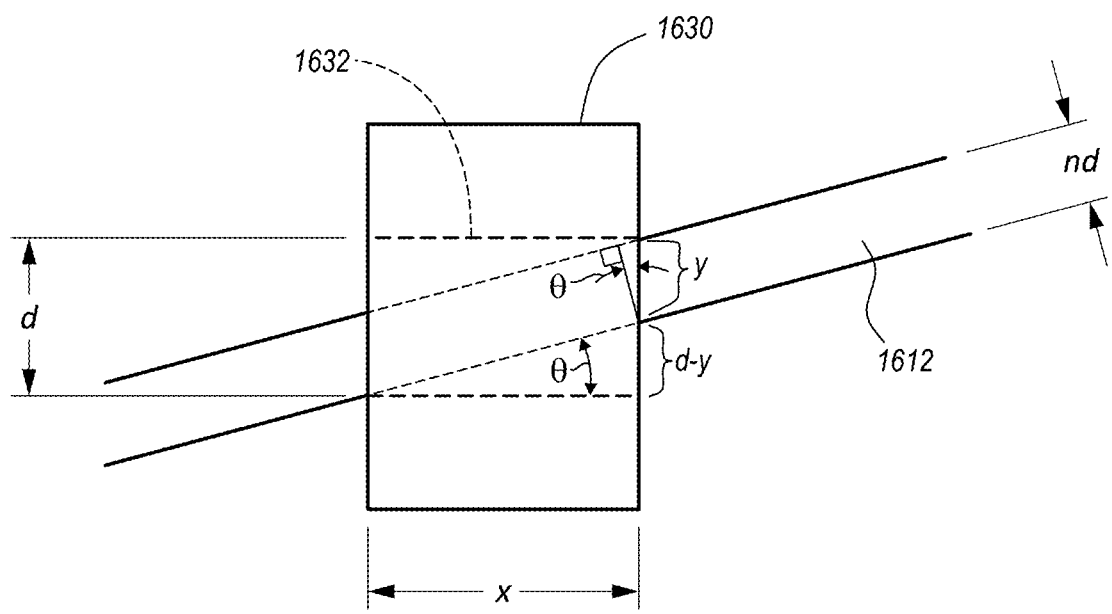
FIG. 46 is a simplified view of a magnetic element and cannula according to one embodiment.

FIG. 46 geometrically shows the extent of possible angular deviation between the magnetic element 1630 and the needle cannula 1612 when the cannula is received through the magnetic element hole 1632. In particular, the offset angle θ of deviation between the cannula 1612 and the magnetic element 1630 is shown, together with the diameter d of the hole 1632. The needle cannula diameter, nd, is also shown. A right triangle is formed, including the offset angle θ, the adjacent side length x, hypotenuse h, and opposite side d−y, where y is measured at an angle across the cannula 1612, as shown.

The following trigonometric functions can be used to find the maximum offset angle the magnetic element of a given dimension can be deviated while still allowing a sized needle cannula to be suitably received therethrough:

$$\sin \theta = d-y/h \quad (1)$$

$$\cos \theta = nd/y \quad (2)$$

$$\tan \theta = \sin \theta / \cos \theta = d-y/x \quad (3)$$

$$h = x^2 + [(d-y)^2]^{1/2} \quad (4)$$

$$\theta = \cos^{-1} * nd/y \quad (5)$$

In one embodiment, the offset angle θ can be determined by using the known values for d, nd, and x to solve for y, then substitute y back into the equations to determine θ. Knowledge of the maximum offset angle θ for a given size of magnetic element enables a specification for the magnetic element to be made, which specification details the maximum variance possible between the physical axis and the magnetic axis of the magnetic element.

Figure 47A:
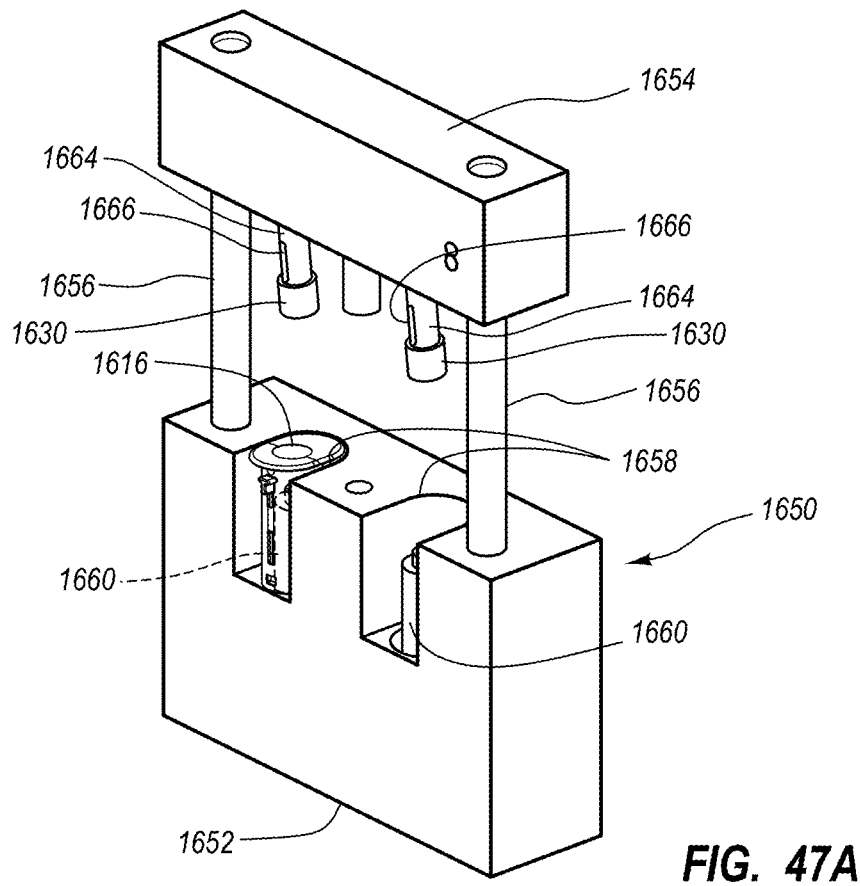
FIGS. 47A-48B are various views of a fixture for mating a magnetic element to a portion of a needle assembly according to one embodiment.
Figure 47B:
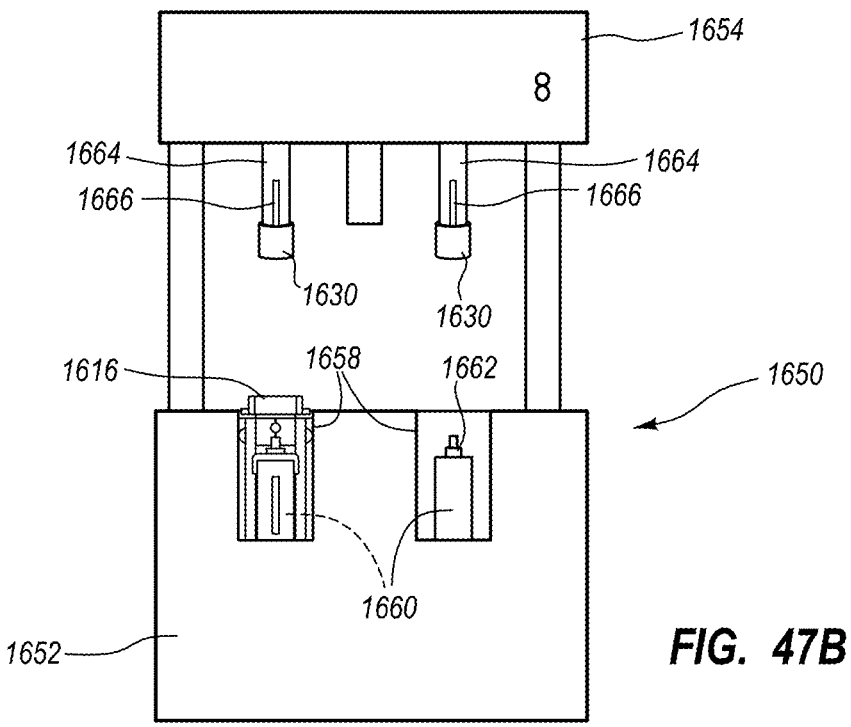

FIGS. 47A-47B show details of a magnetic element insertion fixture 1650 for inserting magnetic elements into the safety can 1616 (FIGS. 41A-41C), according to one embodiment. The fixture 1650 includes a base 1652 that has a slide portion 1654 slidably attached thereto via two slide posts 1656. Two cavities 1658 are defined in the base 1652. A post 1660 is included in each cavity 1658 that is sized to accept thereon the safety can 1616. A guide pin 1662 upwardly extends from each post 1660.

The slide portion 1654 includes two downwardly extending, angled insertion posts 1664 that are each configured to releasably hold a corresponding one of the magnetic elements 1630. Notches 1666 are included on each angled insertion post 1664 to enable orientation of the magnetic elements. The insertion posts 1664 are angled to match the angle of deviation of the magnetic axis of the magnetic element placed thereon from its physical axis. In one embodiment, the deviation between the physical axis and the magnetic axis of the magnetic element 1630 is known so as to enable it to be matched with a properly angled insertion post 1664. Indeed, in a batch of magnetic elements, initial sorting of the magnetic elements according to the magnitude of deviation between the physical and magnetic axes can be performed in one embodiment. In one embodiment, the angle of the insertion posts 1664 can be adjusted to suit the magnetic axis deviation in the magnetic elements. If needed, the notches 1666 can be used as reference features to properly orient the magnetic elements on the angled insertion posts 1664.

Figure 48A:
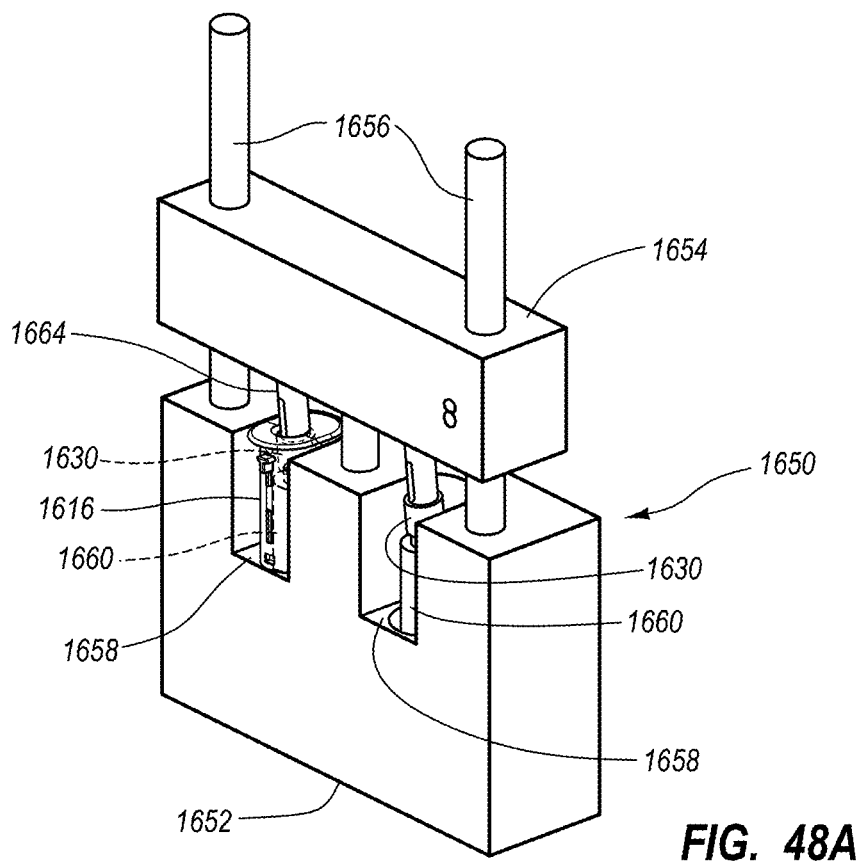
Figure 48B:
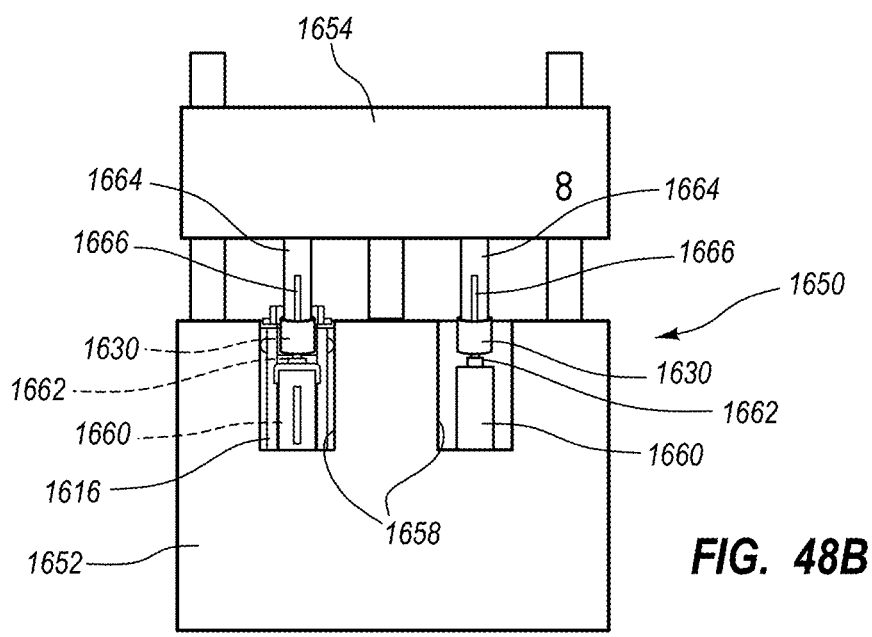

FIGS. 48A and 48B show use of the insertion fixture 1650 in inserting magnetic elements 1630 into corresponding safety cans 1616. As shown, with the magnetic elements 1630 included on each angled insertion post 1664, the slide portion 1654 is lowered via the slide posts 1656 until the magnetic element is received into a recess of the safety can 1616. As the safety can is held by the posts 1660 at an upwardly erect orientation, the magnetic element is inserted into the safety can recess at the desired angled orientation so that its magnetic axis is properly aligned with the safety can and the longitudinal axis of a cannula that will be subsequently attached with the safety can. Adhesive or other fixation medium can be used to affix the magnetic element 1630 in place at its angled orientation. The slide portion 1654 can then be raised so as to release the angled insertion post 1664 from engagement with the magnetic element 1630 and safety can 1616. Note that the number of insertion posts and cavities on the insertion fixture can be varied in one embodiment so as to simultaneously perform a desired number of magnetic element insertion procedures.

Figure 49:
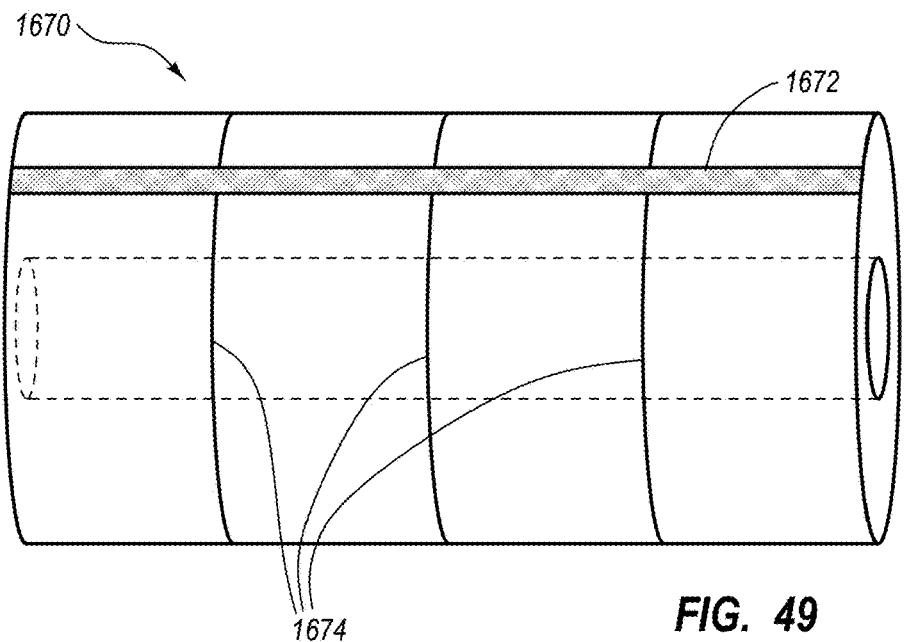
FIG. 49 is a side view of a bar of magnetic material used in forming a magnetic element according to one embodiment.
Figure 50:
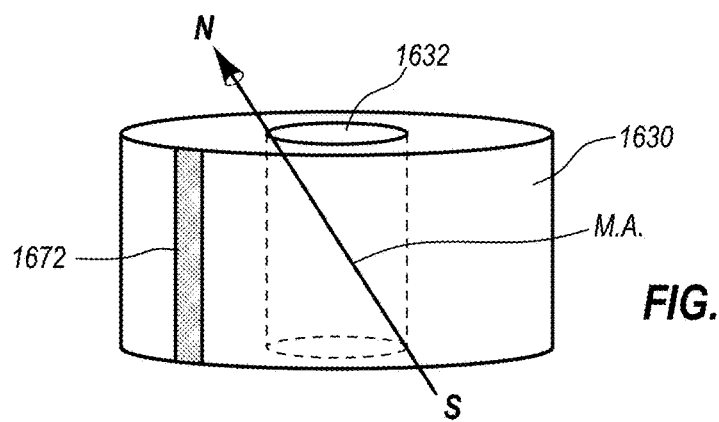
FIG. 50 shows a portion of the bar of magnetic material of FIG. 49.
Figure 51:
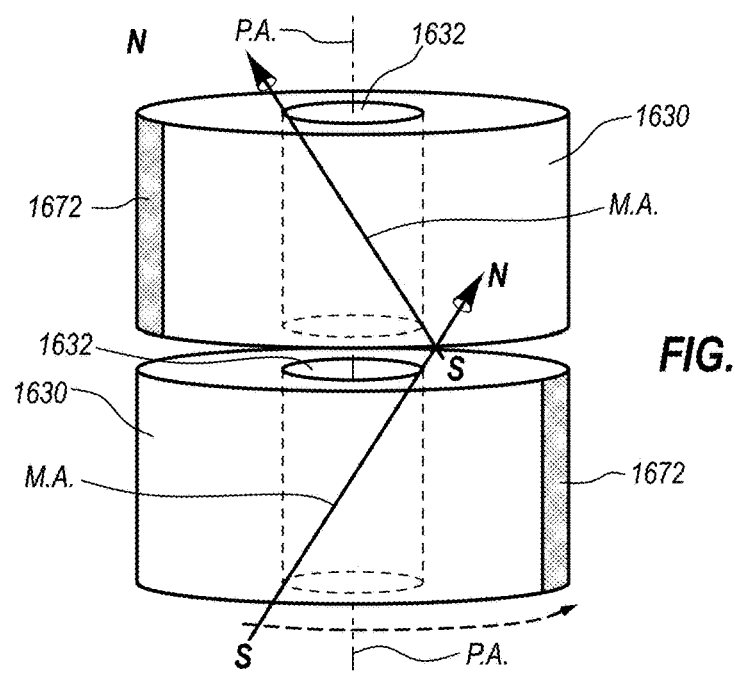
FIG. 51 shows formation of a magnetic element according to one embodiment.

FIGS. 49-51 depict a manner for substantially aligning a magnetic axis of a magnetic element with its physical axis, according to one embodiment. FIG. 49 shows a bored cylindrical magnetic rod 1670 including a magnetic material. An orientation mark 1672 is included along the length of the rod 1670. The rod 1670 is sliced orthogonally to its central axis along cut lines 1674 to yield a plurality of magnetic elements 1630 including a hole 1632, one of which is shown in FIG. 50. The magnetic axis M.A. of the magnetic element 1630 is shown.

As shown in FIG. 51, two magnetic elements 1630 cut from the rod 1670 are rotated 180 degrees with respect to one another such that their respective orientation marks 1672 are opposed to one another. The two magnetic elements are mated to one another, such as via adhesive. This rotation results in placing the magnetic axes M.A. of the magnetic elements 1630 opposite one another such that the opposing components of their magnetic axes cancel out one another. This results in a net magnetic axis for the joined magnetic elements 1630 that is substantially coaxially aligned with the central physical axis P.A. of the joined magnetic elements, as desired. Note that more than two magnetic elements can be joined, and that other symmetrically shaped rods/masses could be used to achieve the results described here. Also, discrete magnetic elements that are not cut from the same bar of magnetic material but have similar magnetic axis-to-physical axis deviations can be grouped together to be joined in the manner just described, in one embodiment.

Figure 52A:
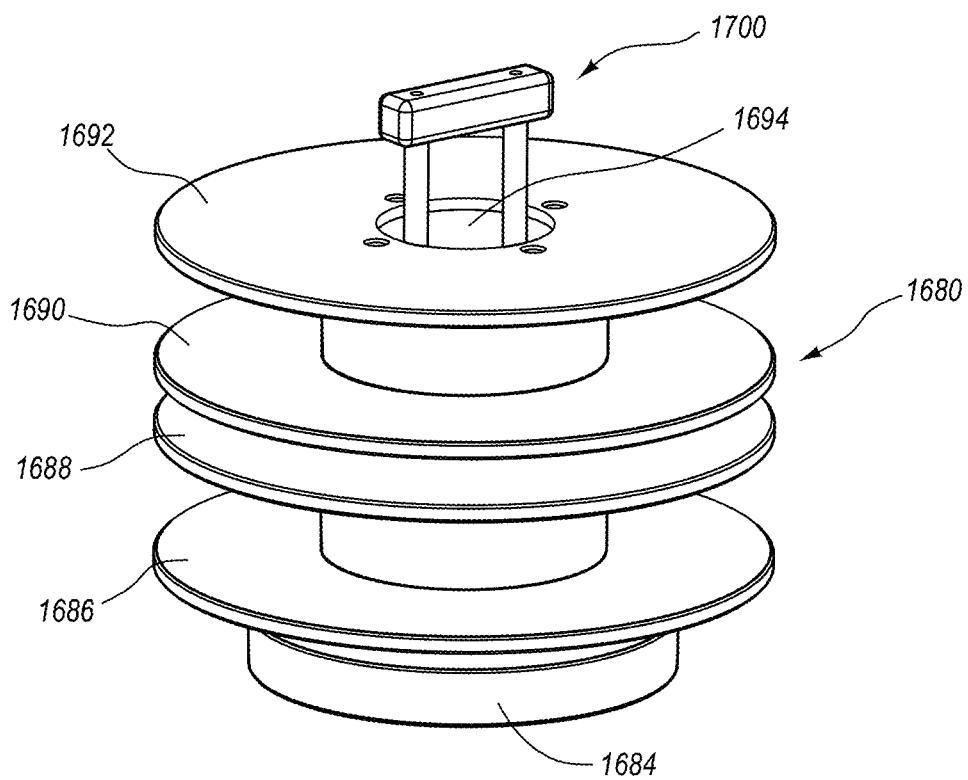
FIGS. 52A and 52B shows various views of an alignment coil assembly according to one embodiment.

FIGS. 52A-54C depict various details regarding an alignment coil assembly 1680 that can be used in orienting magnetic elements for inclusion with a needle assembly, such as the needle assembly 1610 shown in FIGS. 41A-41C, according to one embodiment. As shown in FIGS. 52A and 52B, the alignment coil assembly 1680 includes a base 1682 (FIG. 52B) on which a plurality of components are attached together in a stacked configuration, including a mount 1684, a lower coil bobbin 1686, a centerplate 1688, an upper coil bobbin 1690, and a top plate 1692. These components in one embodiment include a non-magnetically conductive material, such as aluminum and/or brass, and cooperate to define a central bore 1694 of the assembly 1680.

Each of the lower coil bobbin 1686 and the upper coil bobbin 1690 includes windings 1696 that, when electrically energized, produce an electromagnetic field in an around the alignment coil assembly 1680. The windings 1696 in one embodiment are secured in place with an adhesive, such as epoxy. The electromagnetic field produced by the windings 1696 is substantially parallel to the longitudinal axis of the central bore 1694 within the volume of the central bore. Operation of the alignment coil assembly 1680 is thus similar in some respects to a single-axis Helmholtz coil. The upper coil bobbin 1690 further defines a plurality of access holes 1698 for providing access to the central bore 1694 from outside the alignment coil assembly 1680.

Figure 53A:
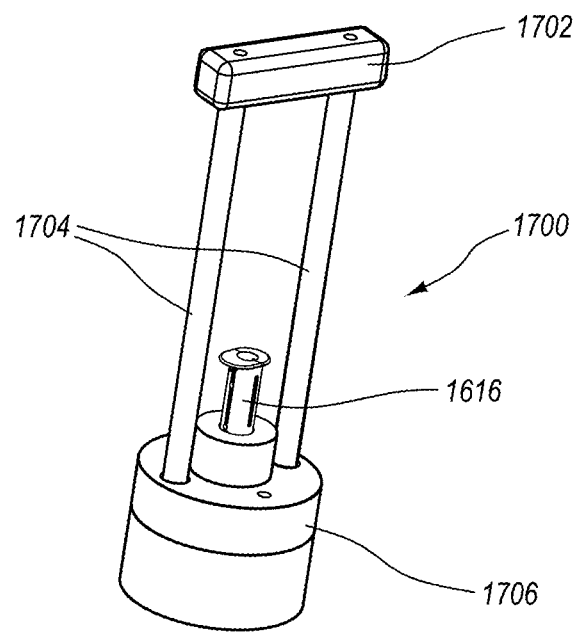
FIGS. 53A and 53B shows a fixture of the alignment coil assembly of FIGS. 52A and 52B.
Figure 53B:
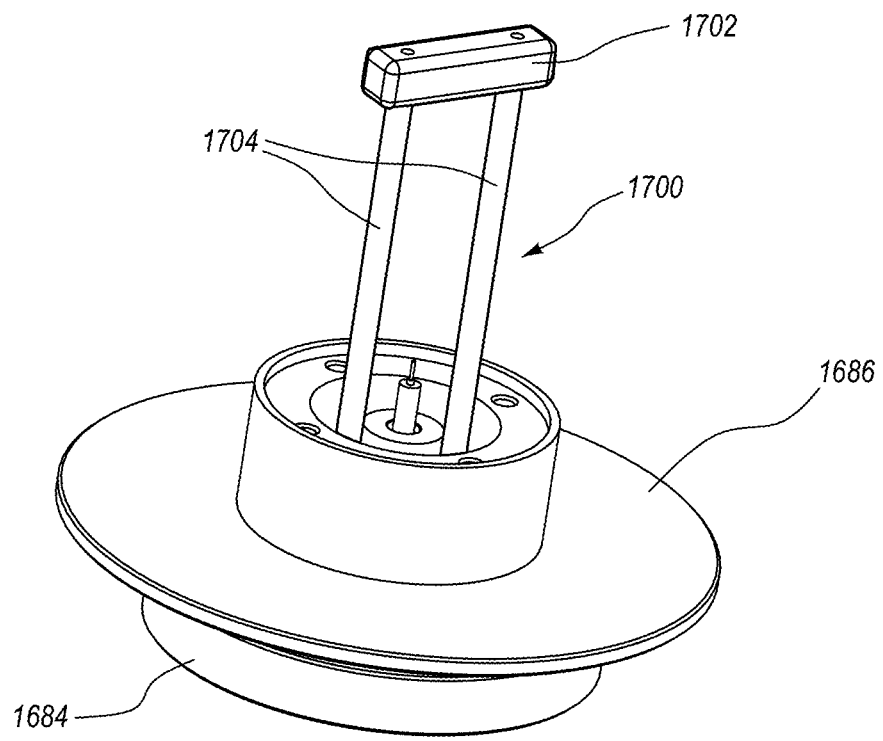
Figure 54A:
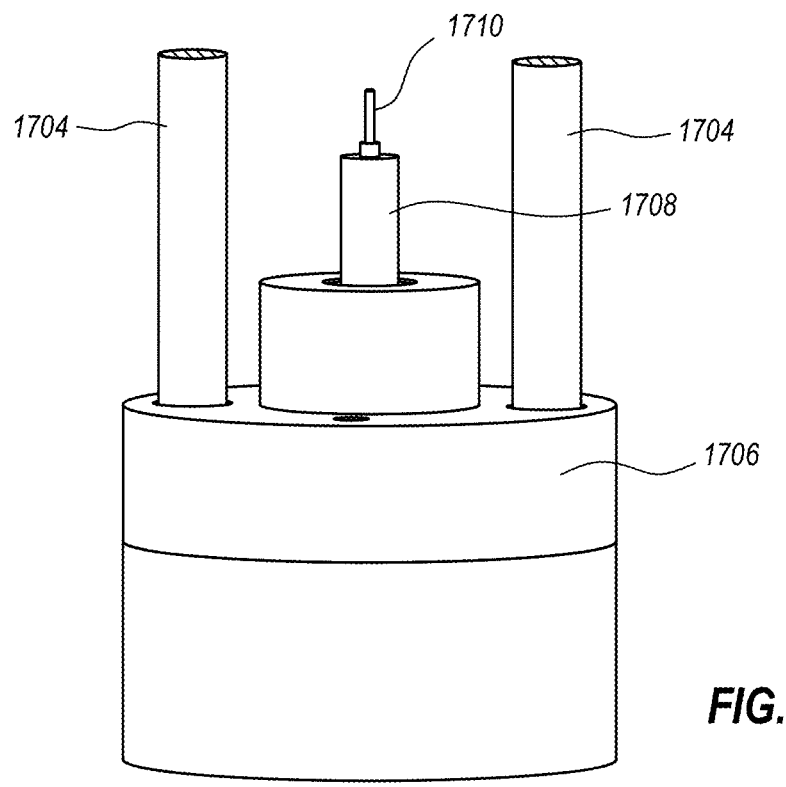
FIGS. 54A-54C shows various details of the fixture of FIGS. 53A and 53B according to one embodiment.

FIGS. 52A, 53A, and 53B show that the alignment coil assembly 1680 further includes a fixture 1700 for holding the safety can 1616 from the needle assembly 1610 (FIGS. 41A-41C) and for inserting the safety can into and withdrawing it from the central bore 1694 of the assembly via manual handling of the fixture, though an automated process is also contemplated. As shown, the fixture 1700 includes a handle 1702 and two extension posts that extend from the handle to a base 1706. FIG. 54A shows that the base 1706 in turn includes a post 1708 for releasably holding the safety can 1616, as seen in FIG. 53A, and a guide pin 1710 upwardly extending from the post. FIG. 53B shows the manner in which the fixture 1700 is seated within the central bore 1694 of the alignment coil assembly 1680, where the centerplate 1688 and the upper coil bobbin 1690 have been removed for clarity. Note that the particular configuration of the alignment coil assembly 1680 and the fixture 1700 can be modified to accommodate needle assembly components of different sizes, designs, etc. In one embodiment, the fixture 1700 includes a suitable non-magnetically conductive material, such as aluminum or brass.

Figure 54B:
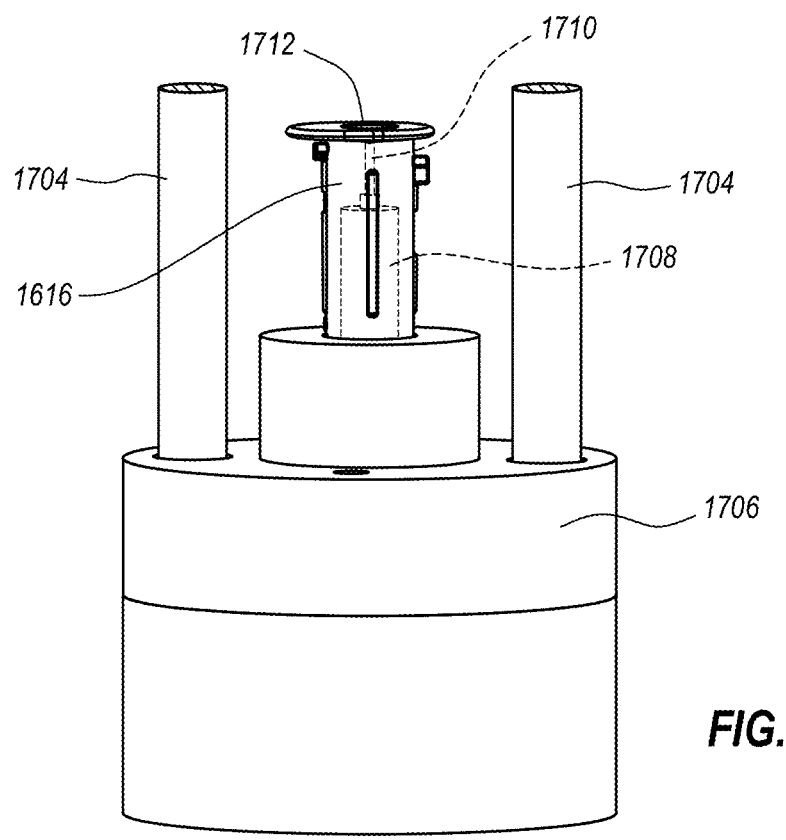
Figure 54C:
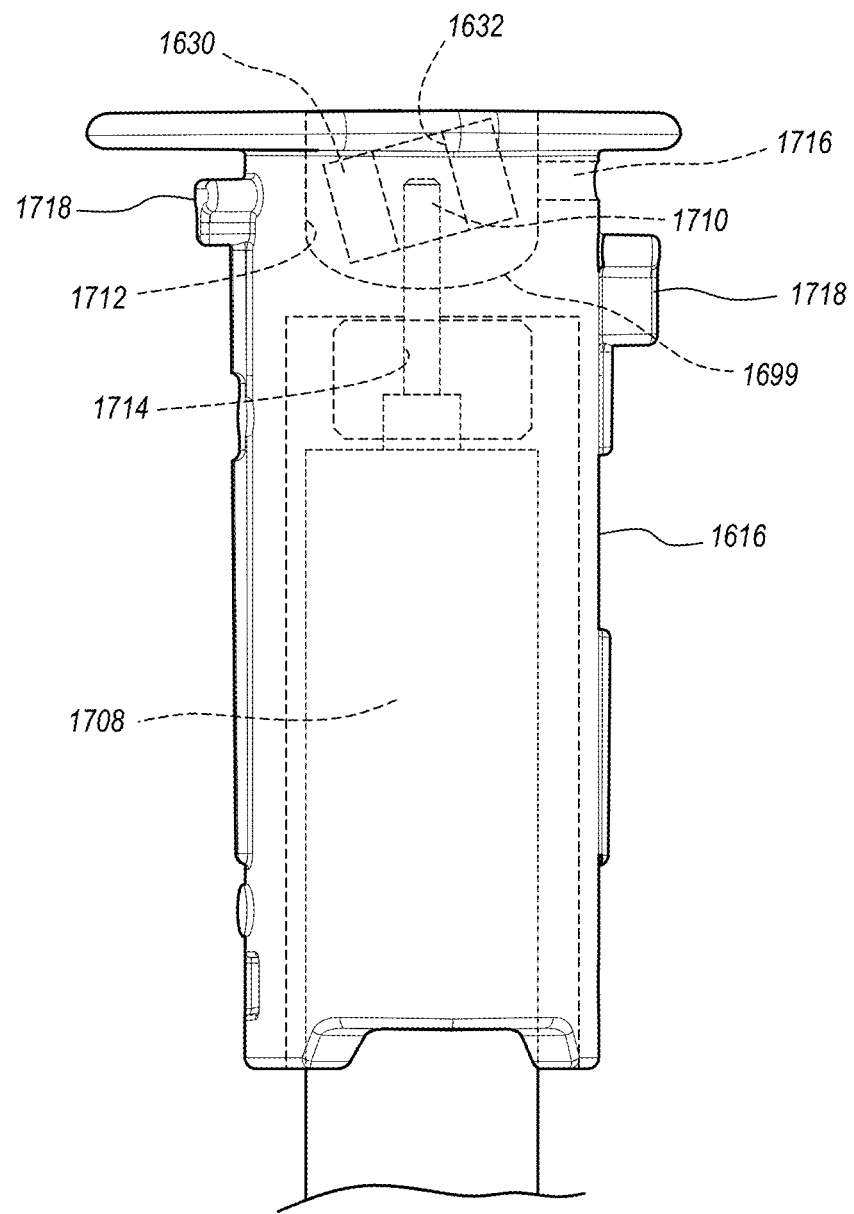

FIG. 54B shows the manner of placement of the safety can 1616 on the post 1708 of the base 1706. So positioned, the guide pin 1710 extends through a cannula conduit 1714 (FIG. 54C) and into a recess 1712 defined by the safety can 1616 to assist in eventual placement of a magnetic element in the recess. Note that the safety can 1616 includes additional features, including orientation features 1718 for enabling the safety can to be oriented as desired in the alignment coil assembly and/or needle assembly, and an adhesive insertion hole for enabling adhesive to be injected into the safety can recess 1712 either before or after the magnetic axis of the magnetic element has been aligned.

During a procedure to place a magnetic element, such as the magnetic element 1630 shown in FIGS. 41A and 41B, into the safety can 1616 via use of the alignment coil assembly 1680, the safety can is first placed on the post 1708 of the fixture 1700, as shown in FIG. 54B. The magnetic element 1630 is placed in the safety can recess 1712 and is left unsecured therein. Note that the safety can recess 1712 includes a concavely rounded feature 1699 on the bottom surface of the recess to facilitate movement/orientation of the magnetic element 1630 during the alignment procedure described here.

With the safety can in place on the post 1708 of the fixture base 1706, the fixture 1700 is then manually inserted into the central bore 1694 of the alignment coil assembly 1680, similar to that shown in FIG. 53B. The windings 1696 of the alignment coil assembly 1680 are then energized, which produces a uniform magnetic field within the central bore 1694 of the alignment coil assembly 1680. The direction of the uniform magnetic field runs parallel to the longitudinal axis of the central bore 1694, which direction is the same as the longitudinal axis of the needle cannula 1612 (FIGS. 41A and 41B) that will be passed through the safety can when assembly is complete, and which direction is the desired direction for the magnetic axis of the magnetic element to be aligned with. This field causes the magnetic element 1630 to orient itself such that its magnetic axis aligns itself with the uniform magnetic field present in the central bore 1694. Such alignment may cause the magnetic element to skew with respect to the guide pin 1710, which guide pin is present to preserve the ability of the needle cannula 1612 (FIGS. 41A and 41B) to pass through the hole 1632 of the magnetic element when needle assembly is complete. Note the skewing of the magnetic element 1630 within the safety can recess 1712 in FIG. 54C. Again, the rounded feature 1699 within the recess 1712 assists with orientation of the magnetic element 1630 by the uniform magnetic field present in the central bore 1694.

Figure 52B:
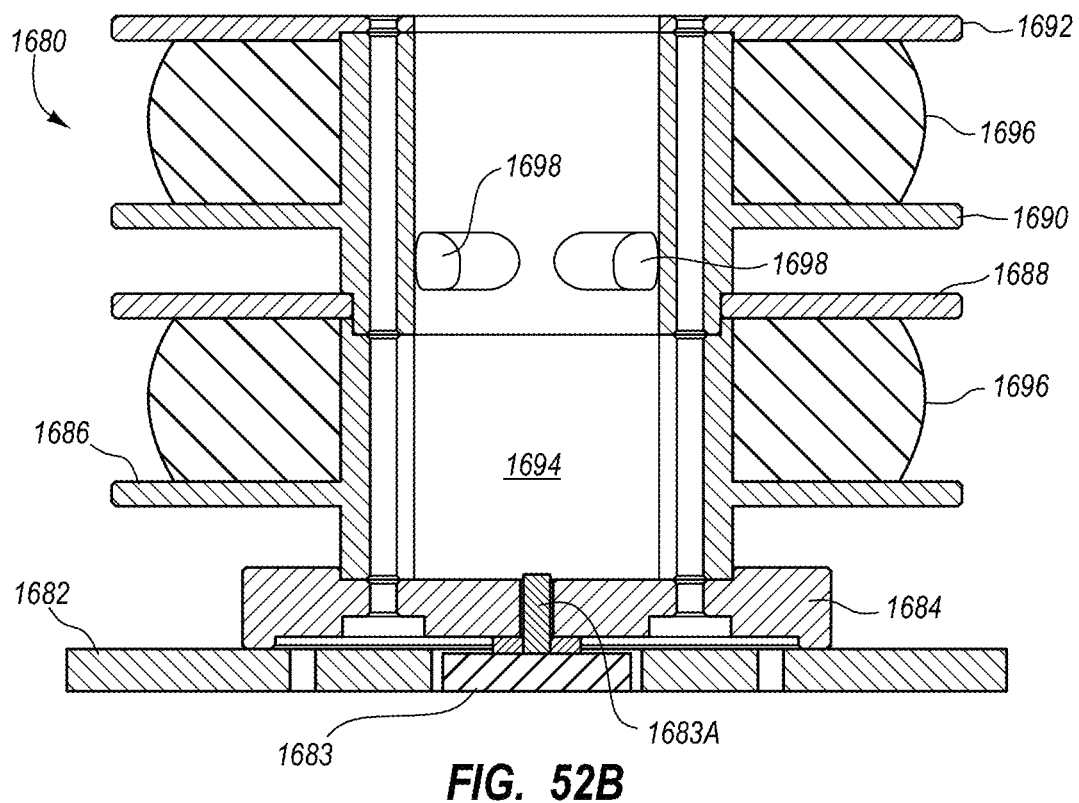

Also, in the present embodiment a vibrating component, such as a vibratory motor 1683 that includes a projection 1683A to contact a portion of the fixture base 1706, is included with the alignment coil assembly 1680 as shown in FIG. 52B to provide vibration to the fixture 1700 and safety can 1616 disposed thereon. This enables the magnetic element 1630 to more freely orient itself to the uniform magnetic field while disposed within the recess 1712 and prevent the magnetic element from physically binding up within the recess.

Once the magnetic axis of the magnetic element 1630 has been properly aligned, a quick-set, UV light-activated epoxy—which was previously introduced into the safety can recess 1712 via the adhesive insertion hole 1716 defined in the housing of the safety can 1616 can be set by exposure to a UV light source introduced into the safety can region within the central bore 1694. Note that access to the adhesive insertion hole 1716 of the safety can 1616 can be made via the access holes 1698 of the upper coil bobbin 1690 of the alignment coil assembly 1680. The use of such a light-cured epoxy enables relatively quick fixation of the magnetic element 1630 within the safety can 1616 in the magnetically aligned orientation.

After or during securement of the magnetic element 1630 within the recess 1712 of the safety can 1616, the cannula 1612 can be passed through the safety can, which can be joined to the needle hub 1626, and the rest of the elements can be incorporated to define the needle assembly 1610 as shown in FIGS. 41A-41C. As a result of the above alignment process, the magnetic axis of the magnetic element 1630 will be substantially coaxially aligned with the longitudinal axis of the needle cannula 1612, as desired. Note that the configuration of the safety can, needle, hub, magnetic element, etc. can vary from what is shown and described herein while still residing within the principles of the present disclosure. For instance, the magnetic element can be incorporated directly into the needle hub or cannula without the presence of a safety can. Note also that other winding configurations are also possible, including square windings and windings of other shapes, three or more windings instead of two, and other configurations that can produce a uniform magnetic field in the central bore of the alignment coil assembly.

Figure 55A:
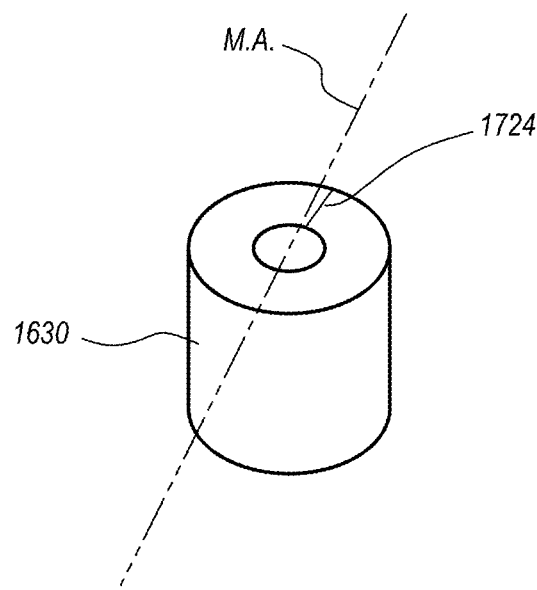
FIGS. 55A-55C shows various views of a magnetic element and cap according to one embodiment.
Figure 55B:
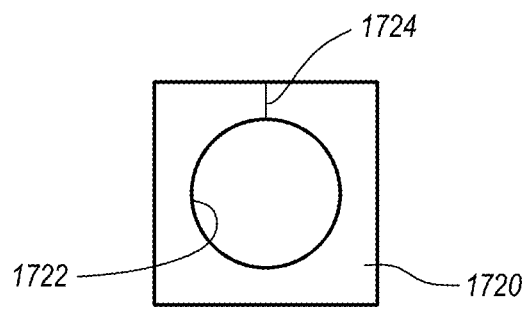
Figure 55C:
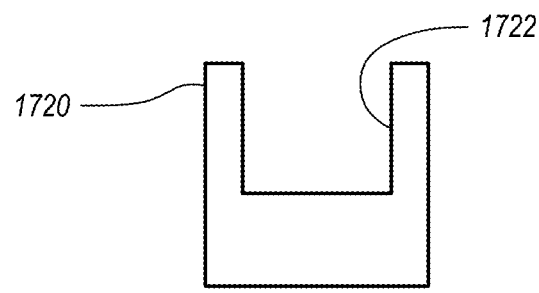

FIGS. 55A-55C show alignment of the magnetic element 1630 according to one embodiment, wherein an orientation mark 1724 is placed on the magnetic element to indicate the orientation of its magnetic axis M.A. A cap 1720 also includes an orientation mark 1724, and further defines a recess 1722 into which the magnetic element 1630 is to be secured. Alignment of the two orientation marks 1724 can enable an observer to suitably manipulate the magnetic element 1630 within the recess 1722 before affixation of the element into place such that the magnetic axis thereof is directed in the desired direction.

Figure 56:
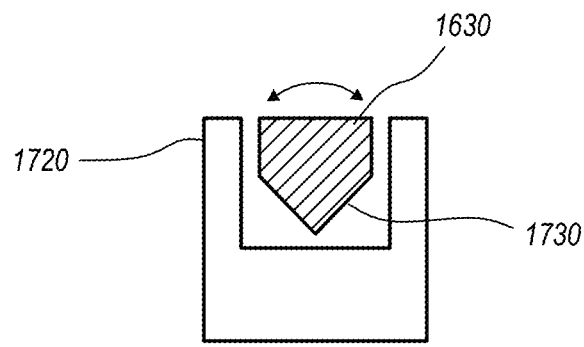
FIG. 56 shows a cap and magnetic element configuration according to one embodiment.
Figure 57:
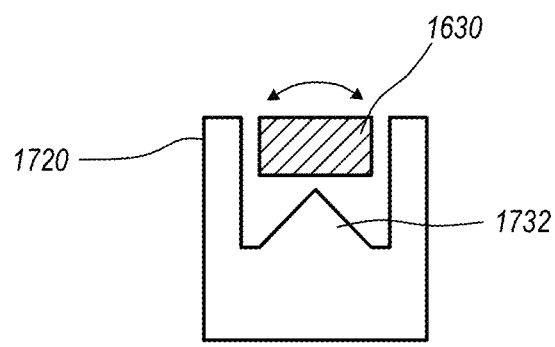
FIG. 57 shows a cap and magnetic element configuration according to one embodiment.
Figure 58:
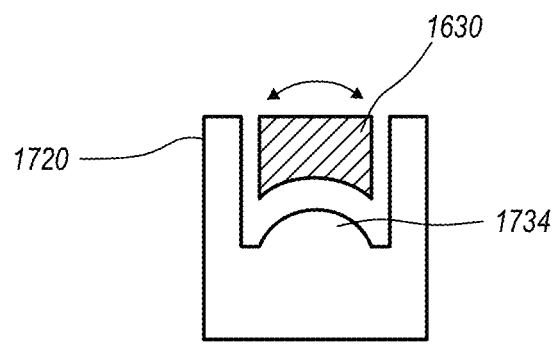
FIG. 58 shows a cap and magnetic element configuration according to one embodiment.

FIGS. 56-58 show additional features for enabling manipulation of the magnetic element 1630 within a recess of the cap 1720, which cap is representative of a variety of recesses for receiving the magnetic element in a needle assembly or other suitable medical device, for use with a needle tracking system such as is described further above. In FIG. 56, the magnetic element 1630 includes a pointed end that enables the element to be more easily manipulated during procedures to orient its magnetic axis. Similarly, FIG. 57 shows the cap 1720 including a pointed feature on the base of the recess 1732 to ease manipulation of the magnetic element. Further, FIG. 58 includes a convexly-rounded feature on the base of the recess to ease magnetic element manipulation. In another embodiment, a concavely-rounded feature can be employed. These and other features can be included in the recess in which the magnetic element is disposed to ease its manipulation during magnetic axis orienting procedures.

Figure 59:
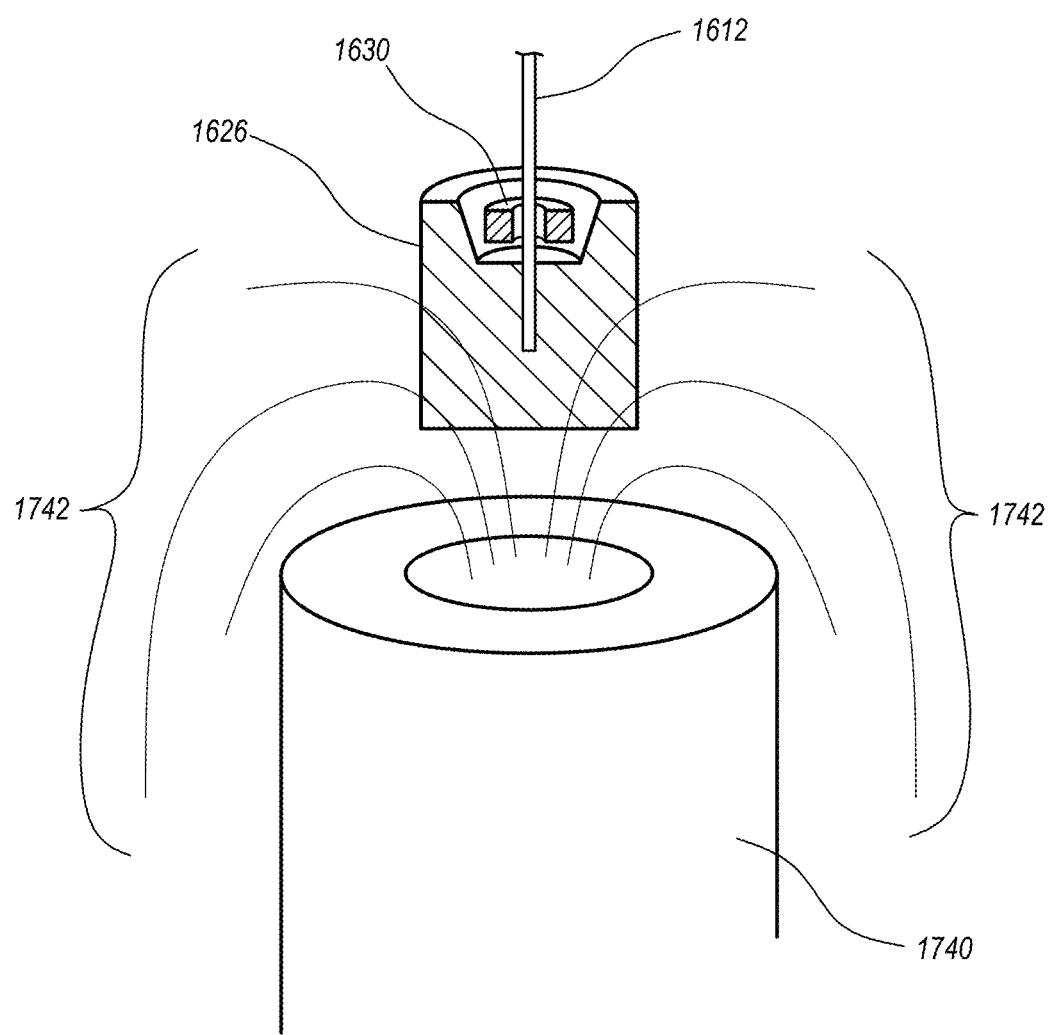
FIG. 59 shows details of a method for aligning a magnetic element in accordance with one embodiment.

FIG. 59 shows alignment of a magnetic axis of the magnetic element 1630 according to another embodiment, wherein the magnetic element 1630 the needle hub 1626 or other suitable component is positioned directly above an electromagnetic or other suitable magnetic coil 1740 such that the magnetic element is positioned within a symmetrical magnetic field as represented by magnetic field lines 1742 of FIG. 59. Such positioning enables the magnetic element to align its magnetic axis with the magnetic field of the coil 1740, thus enabling the magnetic axis of the magnetic element to substantially and coaxially align with the longitudinal axis of the needle cannula 1612, as desired. This process does not require placement of the magnetic element 1630 into an internal magnetic field such as is found in the bore of the alignment coil assembly 1680 described in connection with FIGS. 52A-54C, but rather utilizes a potentially more convenient external magnetic field.

Note that, in addition to coaxially aligning the magnetic axis of the magnetic element with the longitudinal axis of the needle cannula, it is possible in other embodiments to align the magnetic axis along other desired directions, such as perpendicular to the cannula longitudinal axis, for instance. These and other variations are therefore contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of attaching a magnetic element to a needle assembly, the needle assembly including a cannula extending along a longitudinal axis, the method comprising:
   placing the magnetic element in a magnetic field causing a magnetic axis of the magnetic element to align with the magnetic field; and
   subsequent to placement of the magnetic element in the magnetic field and alignment of the magnetic axis of the magnetic element with the magnetic field, securing the magnetic element to a portion of the needle assembly while the magnetic element is aligned with the magnetic field, wherein securing the magnetic element to the portion of the needle assembly includes securing the magnetic element to be physically oriented at an angle with respect to the cannula such that the magnetic axis of the magnetic element is in coaxial alignment with the longitudinal axis of the cannula when the cannula is disposed through a center opening of the magnetic element.

2. The method of attaching according to claim 1, wherein securing the magnetic element to the portion of the needle assembly includes securing the magnetic element via adhesive to a portion of a hub of the needle assembly.

3. The method of attaching according to claim 1, wherein securing the magnetic element further includes securing the magnetic element in place within a safety can of a hub of the needle assembly with a light-curing adhesive.

4. The method of attaching according to claim 1, wherein placing the magnetic element within the magnetic field includes placing the magnetic element within at least one electromagnetic winding, wherein the magnetic field is generated by the at least one electromagnetic winding.

5. The method of attaching according to claim 4, wherein the magnetic element is disposed within the portion of the needle assembly, and wherein the portion of the needle assembly is disposed in a fixture that is placed within the at least one electromagnetic winding.

6. The method of attaching according to claim 5, wherein the at least one electromagnetic winding is included in an alignment coil assembly that includes at least an upper bobbin that includes a first electromagnetic winding and a lower coil bobbin that includes a second electromagnetic winding, wherein the at least one electromagnetic winding includes at least one of the first electromagnetic winding or the second electromagnetic winding.

7. The method of attaching according to claim 1, wherein the magnetic field in which the magnetic element is placed is external to at least one electromagnetic winding.

8. The method of attaching according to claim 1, wherein placing the magnetic element includes positioning the magnetic element in a recess within one of a hub and a safety can of the needle assembly such that the magnetic element is free to move and orient within the recess.

9. The method of attaching according to claim 8, wherein placing the magnetic element in the magnetic field further comprises vibrating the magnetic element while within the recess so as to enable free orientation of the magnetic element to the magnetic field.

10. A method for attaching a magnetic element to a needle holding component, comprising:
    determining an orientation of a magnetic axis of the magnetic element;
    marking the magnetic element with a first orientation mark that indicates the orientation of the magnetic axis;
    inserting the magnetic element into the needle holding component such that (i) the first orientation mark aligns with a second orientation mark included with the needle holding component, and (ii) the magnetic axis extends from the needle holding component in a desired direction; and
    securing the magnetic element to a portion of the needle holding component to be physically oriented at an angle with respect to a needle coupled to the needle holding component such that the magnetic axis of the magnetic element is in coaxial alignment with a longitudinal axis of the needle when the needle is disposed through a center opening of the magnetic element.

* * * * *